(12) United States Patent
Brown

(10) Patent No.: US 9,320,798 B2
(45) Date of Patent: Apr. 26, 2016

(54) LIPID DELIVERY FORMULATIONS

(75) Inventor: Bob D. Brown, Millington, NJ (US)

(73) Assignee: Dicerna Pharmaceuticals, Inc., Cambridge, MA (US)

( * ) Notice: Subject to any disclaimer, the term of this patent is extended or adjusted under 35 U.S.C. 154(b) by 164 days.

(21) Appl. No.: 13/595,360

(22) Filed: Aug. 27, 2012

(65) Prior Publication Data

US 2013/0225663 A1      Aug. 29, 2013

Related U.S. Application Data

(63) Continuation of application No. PCT/US2011/026478, filed on Feb. 28, 2011.

(60) Provisional application No. 61/309,266, filed on Mar. 1, 2010.

(51) Int. Cl.
| | |
|---|---|
| *C07H 21/04* | (2006.01) |
| *A61K 47/28* | (2006.01) |
| *A61K 9/127* | (2006.01) |
| *A61K 31/20* | (2006.01) |
| *A61K 31/713* | (2006.01) |
| *A61K 45/06* | (2006.01) |
| *A61K 47/48* | (2006.01) |
| *A61K 47/18* | (2006.01) |
| *A61K 47/24* | (2006.01) |
| *A61K 39/00* | (2006.01) |

(52) U.S. Cl.
CPC .............. *A61K 47/28* (2013.01); *A61K 9/1272* (2013.01); *A61K 31/20* (2013.01); *A61K 31/713* (2013.01); *A61K 45/06* (2013.01); *A61K 47/18* (2013.01); *A61K 47/183* (2013.01); *A61K 47/24* (2013.01); *A61K 47/48215* (2013.01); *A61K 39/00* (2013.01)

(58) Field of Classification Search
None
See application file for complete search history.

(56) References Cited

U.S. PATENT DOCUMENTS

| | | |
|---|---|---|
| 6,395,771 B1 | 5/2002 | Ramadoss et al. |
| 2002/0156237 A1 | 10/2002 | Schwartz et al. |
| 2003/0113368 A1 | 6/2003 | Nomoto et al. |
| 2004/0229793 A1 | 11/2004 | Balasubramanian et al. |
| 2005/0244858 A1 * | 11/2005 | Rossi et al. ..................... 435/6 |
| 2006/0083780 A1 * | 4/2006 | Heyes et al. ................. 424/450 |
| 2007/0135372 A1 * | 6/2007 | MacLachlan et al. .......... 514/44 |
| 2008/0194806 A1 | 8/2008 | Yedgar |
| 2008/0317839 A1 | 12/2008 | Quay et al. |
| 2009/0041668 A1 | 2/2009 | Contag et al. |
| 2009/0220587 A1 | 9/2009 | Allon et al. |
| 2010/0204305 A1 * | 8/2010 | Young et al. ................ 514/44 A |
| 2011/0110972 A1 * | 5/2011 | Vasievich et al. ........ 424/196.11 |

OTHER PUBLICATIONS

Ma et al (Biochem and Biophys Res. Comm 2005 (330): 755-759).*
Numata et al. "Pulmonary surfactant phosphatidylglycerol inhibits respiratory syncytial virus-induced inflammation and infection" PNAS vol. 107 p. 320-325; Jan. 5, 2010.
Judge et al. Hypersensitivity and Loss of Disease Site Targeting Caused by Antibody Responses to PEGylated Liposomes'; Mol. Ther.; Feb. 2006; vol. 13, No. 2; p. 328-337;.

* cited by examiner

*Primary Examiner* — Kimberly Chong
(74) *Attorney, Agent, or Firm* — Sunstein Kann Murphy & Timbers LLP

(57) ABSTRACT

The invention provides formulations that contain an immunogenic or immunostimulatory cargo, delivery moiety and/or lipid, and a lipid that functions to reduce or prevent induction in a subject of an immune response which would otherwise occur when the immunogenic or immunostimulatory cargo, delivery moiety and/or lipid is administered to a subject as a component of an appropriate control formulation lacking the immune response reducing lipid. Specific immune response reducing lipids and uses thereof are further provided.

36 Claims, 14 Drawing Sheets

DPPC

DPC-033

DPC-036

FIGURE 7

TLR4 Inhibitor, Generic Rendition

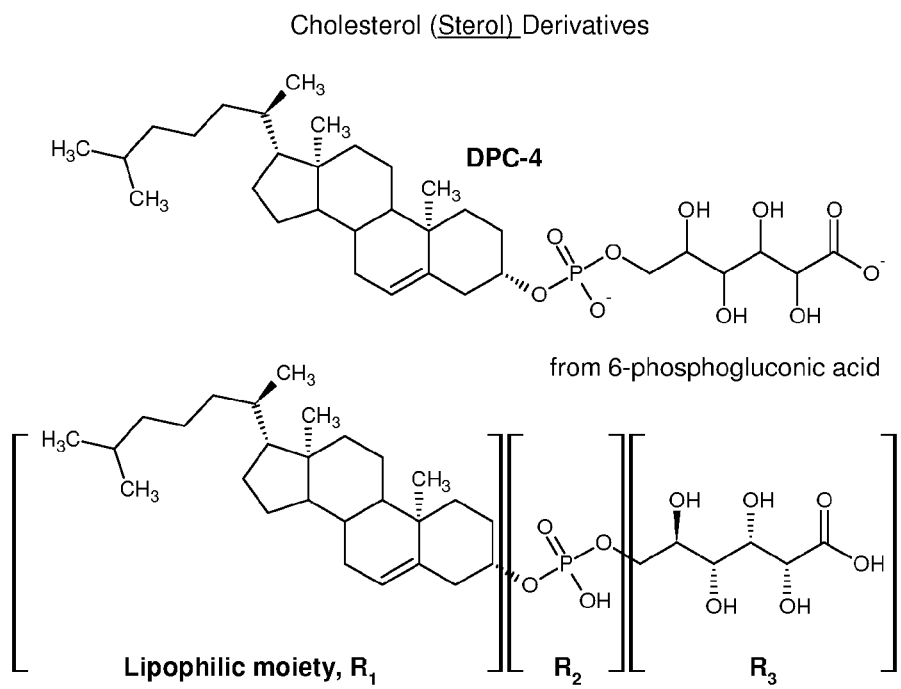

$R_1$ = comprises lipophilic moieties including but not limited to single sterols, dimeric sterols, and multimeric sterols; single alkyl chains from 5 to 24 carbon atoms, multiple alkyl chains from 5 to 24 carbon atoms each, single or multiple symmetric branched alkyl moieties from 10 to 50 carbon atoms each, or single or multiple asymmetric branched alkyl chains ranging from 10 to 50 carbons each; single alkenyl chains containing one or more unsaturations from 5 to 24 carbon atoms, multiple alkyl chains containing one or more unsaturations from 5 to 24 carbon atoms each, single or multiple symmetric branched alkyl moieties containing one or more unsaturations from 10 to 50 carbon atoms each, or single or multiple asymmetric branched alkyl chains containing one or more unsaturations ranging from 10 to 50 carbons each; or mixed alkyl chains from 5 to 24 carbon atoms and alkenyl chains containing one or more unsaturations from 5 to 24 carbon atoms.

$R_2$ = a negatively charged or neutral moiety linking R1 and R3, a comprising negatively charged phosphate ester, neutral phosphonate, carbamate, amide, one or more neutral or negatively charged amino acids, an ether, ketone, or ester; or an alkyl chain from one to 10 carbons; or a disulfide linked moiety.

$R_3$ = a negatively charged or neutral moiety comprising two or more hydroxyls, carbonates, ethers, or carboxylates; or two or more alkyl esters from 1 to 6 carbons; or two or more alkyl esters from 2 to 6 carbons.

TLR4 Inhibitor Head Groups

D- and L-forms separated and mixed stereoisomers where applicable

Compound DPC-1

Compound DPC-2

Compound DPC-3

R₁ as previously described

LIPID DELIVERY FORMULATIONS

CROSS-REFERENCE TO RELATED APPLICATIONS

This application is a Continuation of PCT international application Ser. No. PCT/US2011/026478, filed Feb. 28, 2011, designating the United States, which claims the benefit of U.S. provisional patent application No. 61/309,266, filed Mar. 1, 2010. The entire contents of the aforementioned patent applications are incorporated herein by this reference.

BACKGROUND OF THE INVENTION

A significant complication of using a lipid nanoparticle formulation to deliver an immunogenic or immunostimulatory cargo to a mammalian subject is the propensity of such formulations to induce an immune response (e.g., acting as an immunologic adjuvant) within the subject administered such a formulation. In addition to any immunogenic or immunostimulatory role of a formulation cargo, certain lipids have been identified as capable of activating an innate immune response within a subject—cationic lipids, and lipopolysaccharides in particular, have been identified as activators of TLR4-mediated immune responses. Cationic lipids have also been identified as helping to activate TLR3-, TLR7-, TLR8-, and TLR9-mediated immune responses when formulated with nucleic acid cargoes/payloads (e.g., single- and double-stranded nucleic acids and nucleic acid analogs, including RNA and analogs, DNA and analogs, and nucleic acid mimics or other modifications of oligonucleotides (NAs), and peptides, proteins and analogs, and other formulation components, such as PEG, PEG-linked moieties and other polymers, and lipidic components (excipients).

Immunogenic or immunostimulatory properties of lipid formulations have been identified for a number of cargo classes, including peptides, proteins and nucleic acids. For example, dsRNAs have been described to trigger immune responses via at least two mechanisms: (1) dsRNAs of greater than 30 base pairs in length can trigger immunostimulation (Manche et al. Mol. Cell Biol. 12: 5238-42) by a mechanism dependent upon two or more PKR monomers simultaneously binding such a dsRNA molecule (Lemaire et al. *J. Mol. Biol.* 381: 351-60); and (2) dsRNAs of any length can also trigger immunostimulatory responses in mammalian subjects via MDA5-, TLR3-, OAS1-, RIG-I-, TLR7-, and/or TLR8-mediated interferon activation. Cationic lipids can potentiate these responses (Hagele et al. Nephrology Dialysis Transplantation 2009 24(11):3312-3318). ssDNAs and dsDNAs and analogs, especially those including base modifications necessary for other pharmacological activities (Kandimala et al. Proc Natl Acad Sci USA. 2005 May 10; 102(19):6925-30), can trigger immunostimuluation via TLR9 (Krieg et al. *Nature.* 374: 546-9; Kreig, *Trends Microbiol.* 9: 249-52). Such immunologic responses can produce serious side effects in a subject, including fever, chills, hypotension, arrhythmia, liver damage and other harmful or potentially fatal effects, and can be triggered by formulation components, payloads, or both.

Thus, discovery of a means for reducing or blocking the immunostimulatory (e.g., immunologic adjuvant) properties of a formulation comprising an immunogenic or immunostimulatory cargo or pharmacologically necessary component (e.g., a nucleic acid, protein, small drug molecule and/or excipient) while retaining or improving the desired pharmacological activity of the formulation/cargo (e.g., where the cargo is a nucleic acid, protein, active drug molecule or vehicle component, retaining robust target gene inhibitory and/or other pharmacological efficacy and potency of such formulations) would allow for improved use of such immune response reducing formulations in mammalian subjects, including humans.

BRIEF SUMMARY OF THE INVENTION

The invention is based, at least in part, upon the discovery that certain lipids can be employed within lipid-based formulations, e.g., formulations comprising immunogenic or immunostimulatory cargoes, lipids and/or delivery moieties, to reduce or eliminate the immune response of a subject to such a formulation. Exemplary immunogenic or immunostimulatory cargoes of the formulations of the invention include peptides, proteins and nucleic acids (e.g., dsRNAs, including siRNAs and Dicer-substrate siRNAs ("DsiRNAs")) and functional excipients (e.g., PEGylated lipids, other polymer-conjugated components and polyethoxylated castor oil (Cremophor EL™, BASF, Parsippany, N.J.) and other solvents or excipients). In certain embodiments, the inclusion of specific lipids, e.g., non-cationic lipids, within the cargo delivery formulations described herein provides particular advantage in masking, dampening, reducing and/or eliminating (antagonizing or suppressing) the immune response of a subject to such immunogenic or immunostimulatory cargoes.

In certain aspects, the present invention is directed to formulations containing an immunogenic or immunostimulatory cargo and a lipid (e.g., a non-cationic lipid or a lipid-antagonist conjugate (e.g., mianserin, imiquimod or other small molecule; Sacre et al. *J Immunol.* 181: 8002-9) that reduces or prevents induction in a mammalian subject of an immune response that would otherwise occur, were the immunogenic or immunostimulatory formulation/cargo administered to a mammalian subject as a component of an appropriate control formulation that lacks the immune response reducing lipid. Methods for preparing such formulations and the chemical structures of such immune response reducing lipids and lipid-conjugates are also provided. Such immune response reducing formulations are not only expected to exhibit surprisingly reduced levels of immune response and/or prevent immunostimulation when administered to a mammalian subject, but are further expected to allow for inclusion of an immunogenic delivery moiety (e.g., functional excipient, e.g., a peptide, carbohydrate, etc.)) within an immune response reduced formulation, by reducing the immune response of a subject to the immunogenic delivery moiety and/or by averting formation of an immunostimulatory formulation within which the immunogenic or immunostimulatory cargo or an immunostimulatory lipid of the formulation acts as an adjuvant with respect to the immunogenic delivery moiety.

Within certain immune response reduced formulations of the invention that comprise both an immunogenic moiety (e.g., immunologic adjuvant) and an immune response reducing lipid or lipid-conjugate (e.g., a non-cationic lipid), the immune response reducing lipid or lipid-conjugate of such formulations can mask (e.g., reduce or entirely block) the immunogenicity of an associated immunogenic moiety (e.g., an immunogenic delivery moiety comprising a peptide, carbohydrate, lipid, lipopolysaccharide, etc., or other immunogenic modification).

In additional aspects, the immune response reduced formulations of the invention can comprise PEG and/or PEGylated molecules, wherein the immune response reducing lipid (e.g., non-cationic lipid or lipid-conjugate) of the formulation reduces or prevents an immune response to PEG (e.g., induction and/or appearance of antibodies reactive against PEG) in a subject administered the formulation of the invention, as compared to an appropriate control formulation lacking the immune response reducing lipid. Thus, in some embodiments, a PEG moiety is a component of a lipidic formulation of the invention. In certain embodiments, a PEG moiety is directly attached to a cargo of the formulation (e.g., a formulation in which a cargo peptide is a PEGylated protein or a formulation in which a cargo nucleic acid is a PEGylated nucleic acid, including single- or double-stranded RNA or DNA, and nucleic acid analogs) or to a lipid of the formulation (e.g., the formulation contains PEGylated lipids).

In certain aspects, the present invention is directed to formulations containing a double stranded RNA ("dsRNA") and a non-cationic lipid or lipid-conjugate that reduces or prevents induction in a mammalian subject of an immune response that would otherwise occur when a dsRNA is administered to a mammal subject as a component of an appropriate control formulation lacking the immune response reducing non-cationic lipid. Methods for preparing such immune response reduced dsRNA formulations and the chemical structures of such immune response reducing non-cationic lipids are also provided. Such immune response reduced dsRNA formulations are expected to exhibit surprisingly reduced levels of immune response and/or prevent immunostimulation when administered to a mammalian subject, but are also expected to allow for inclusion of an immunogenic delivery moiety (e.g., a peptide, carbohydrate, etc.) within a dsRNA formulation without thereby forming an immunostimulatory dsRNA formulation within which the dsRNA or an immunogenic or immunostimulatory lipid of the formulation acts as an adjuvant.

Exemplary immune response reducing lipids of the formulations of the instant invention include palmitoyl-oleoyl-phosphatidylglycerol (POPG), dipalmitoylphosphatidylcholine (DPPC), the lipids of FIGS. 1-14, isolated chiral forms of DOTAP (R-DOTAP or S-DOTAP), isolated chiral forms of DSPC (R-DSPC or S-DSPC), and derivatives thereof.

In one aspect, the invention provides a formulation that includes an agent capable of inducing an immune response in a mammalian subject when the agent is administered to the mammalian subject; and a first lipid capable of reducing or preventing the immune response to the agent in the mammalian subject when the formulation is administered to the mammalian subject, as compared to an appropriate control formulation lacking the first lipid.

In one embodiment, the first lipid is a cationic lipid. Optionally, the first lipid is DPC-25 shown in FIG. 14.

In another embodiment, the first lipid is a non-cationic lipid. Optionally, the first lipid is an anionic lipid. In an additional embodiment, the first lipid is POPG, DPPC, a lipid of FIGS. 1-14, or a derivative thereof.

In one embodiment, the agent is a cargo of the formulation. In another embodiment, the agent is a nucleic acid (optionally, the nucleic acid is a dsRNA), an active drug molecule or a vehicle component. In a related embodiment, the agent is an excipient of the formulation, e.g., polyethoxylated castor oil (e.g., Cremophor EL™, BASF, Parsippany, N.J.).

In another embodiment, the formulation also includes a second lipid. In one embodiment, the second lipid is a cationic lipid. Optionally, the cationic lipid is N,N-dioleyl-N, N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxypropylamine (DODMA), 1,2-DiLinoleyloxy-N,N-dimethylaminopropane (DLinDMA) or 1,2-Dilinolenyloxy-N, N-dimethylaminopropane (DLendMA). In a related embodiment, the second lipid activates TLR4 in the absence of the first lipid.

In a further embodiment, the first lipid includes between 1 mol % and 80 mol % of the total lipid of the formulation; optionally, between 20 mol % and 50 mol % of the total lipid of the formulation.

In one embodiment, the immune response is a TNF-alpha-mediated immune response or an interferon-mediated immune response. Optionally, the interferon is IL-1β.

In another embodiment, the immune response in a subject is measured by detecting elevated interferon levels in the subject and/or detecting elevated TNF-alpha levels in the subject. In an additional embodiment, the immune response in a subject is measured by detecting a symptom or combination of symptoms of immune response, including fatigue, flu-like symptoms, diarrhea, reduced bone marrow function, infection, rash, hypotension, arrhythmia, elevated liver enzymes, complement activation, splenomegaly, enlarged lymph nodes, erythema, fainting, anemia and/or bleeding problems.

In one embodiment, the formulation also includes a delivery moiety. Optionally, the delivery moiety is capable of inducing an immune response in a mammalian subject when the delivery moiety is not present in the formulation. In a related embodiment, the immune response capable of being induced in the mammalian subject by the delivery moiety when the delivery moiety is not present in the formulation is an innate immune response. In certain embodiments, the delivery moiety is a polypeptide, a carbohydrate or a lipid. Optionally, the delivery moiety is somatostatin (sst2), bombesin/GRP, luteinizing hormone-releasing hormone (LHRH), neuropeptide Y (NPY/Y1), neurotensin (NT1), vasoactive intestinal polypeptide (VIP/VPAC1) or cholecystokinin (CCK/CCK2).

In an additional embodiment, the formulation induces less of an immune response when administered to a subject than the immune response observed in a subject when the delivery moiety is administered to the subject in the absence of the first lipid of the formulation. Optionally, the formulation induces no detectable immune response in a subject when administered to the subject.

In another embodiment, the formulation further includes PEG. Optionally, the agent is PEGylated. In a related embodiment, the first lipid reduces or prevents formation of antibodies specific for PEG in the subject.

In another aspect, the invention provides a formulation having a dsRNA possessing a sequence sufficiently complementary to a target gene along at least 19 nucleotides of the dsRNA sequence length to reduce target gene expression when the dsRNA is introduced into a mammalian cell; a first lipid; and a second lipid, where the first lipid is capable of reducing or preventing an immune response to the dsRNA and/or to the second lipid in a mammalian subject when the dsRNA is administered to the mammalian subject, as compared to an appropriate control dsRNA lacking the first lipid.

In one embodiment, the dsRNA is an isolated double stranded ribonucleic acid (dsRNA) having a first oligonucleotide strand possessing a 5' terminus and a 3' terminus and a second oligonucleotide strand possessing a 5' terminus and a 3' terminus, where the dsRNA includes a duplex region of at least 25 base pairs; the first strand has a length which is at least 25 nucleotides and the second strand has a length which is at least 26 nucleotides; the second strand is 1-5 nucleotides longer at its 3' terminus than the 5' terminus of the first strand; and the second oligonucleotide strand is sufficiently complementary to the target gene along at least 19 nucleotides of the second oligonucleotide strand length to reduce target gene expression when the dsRNA is introduced into a mammalian cell.

In certain embodiments, the first strand of the dsRNA is 25-30 nucleotides in length. Optionally, second strand of the dsRNA is two nucleotides longer at its 3' terminus than the 5' terminus of the first strand. Alternatively, the 3' terminus of the first strand of the dsRNA and the 5' terminus of the second strand form a blunt end.

In one embodiment, the dsRNA possesses first strand and second strand lengths of any of the following: 25 nucleotide first strand and second strand length 26, 27, 28 or 29 nucleotides; 26 nucleotide first strand and second strand length 27, 28, 29 or 30 nucleotides; 27 nucleotide first strand and second strand length 28, 29 or 30 nucleotides; 28 nucleotide first strand and second strand length 29 or 30 nucleotides; or 29 nucleotide first strand and 30 nucleotide second strand. In certain embodiments, the first strand of the dsRNA is 25 nucleotides in length and the second strand is 27 nucleotides in length.

In another embodiment, the dsRNA is present in an amount effective to reduce target RNA levels by an amount (expressed by %) of at least 10%, at least 50% or at least 80-90% when the formulation contacts a mammalian cell in vitro.

In a further embodiment, the effective amount of the dsRNA cargo is 1 nanomolar or less, 200 picomolar or less, 100 picomolar or less, 50 picomolar or less, 20 picomolar or less, 10 picomolar or less, 5 picomolar or less, 2, picomolar or less and 1 picomolar or less in the environment of the cell.

In an additional embodiment, the dsRNA is present in an amount effective to reduce target RNA levels when the formulation contacts a cell of a mammalian subject by an amount (expressed by %) of at least 10%; optionally, at least 50%, or at least 80-90%.

In one embodiment, the effective amount of the formulation or of the dsRNA is a dosage of 1 microgram to 5 milligrams per kilogram of the subject per day, 100 micrograms to 0.5 milligrams per kilogram, 0.001 to 0.25 milligrams per kilogram, 0.01 to 20 micrograms per kilogram, 0.01 to 10 micrograms per kilogram, 0.10 to 5 micrograms per kilogram, or 0.1 to 2.5 micrograms per kilogram.

In another aspect, the invention provides a pharmaceutical composition that includes a formulation as described herein and a pharmaceutically acceptable carrier.

An additional aspect of the invention provides a kit that includes a formulation as described herein, and instructions for its use.

A further aspect of the invention provides a method for reducing expression of a target gene in a mammal involving administering a formulation as described herein to a mammal in an amount sufficient to reduce expression of a target gene in the mammal.

Optionally, the formulation is administered at a dosage 1 microgram to 5 milligrams per kilogram of the mammal per day, 100 micrograms to 0.5 milligrams per kilogram, 0.001 to 0.25 milligrams per kilogram, 0.01 to 20 micrograms per kilogram, 0.01 to 10 micrograms per kilogram, 0.10 to 5 micrograms per kilogram, and 0.1 to 2.5 micrograms per kilogram. In certain embodiments, the route of administration is by intravenous injection, intramuscular injection, intraperitoneal injection, infusion, subcutaneous injection, transdermal, aerosol, rectal, vaginal, topical, oral or by inhalation.

In another aspect, the invention provides a compound of formula (I): $R_1$—$R_2$—$R_3$ (I) where $R_1$ includes a lipophilic moiety that is a single sterol, a dimeric sterol, a multimeric sterol, a single alkyl chain from 5 to 24 carbon atoms, a multiple alkyl chain from 5 to 24 carbon atoms each, a single symmetric branched alkyl moiety from 10 to 50 carbon atoms each, a multiple symmetric branched alkyl moiety from 10 to 50 carbon atoms each, a single asymmetric branched alkyl chain ranging from 10 to 50 carbons each, a multiple asymmetric branched alkyl chain ranging from 10 to 50 carbons each, a single alkenyl chain containing one or more unsaturations from 5 to 24 carbon atoms, a multiple alkyl chain containing one or more unsaturations from 5 to 24 carbon atoms each, a single symmetric branched alkyl moiety containing one or more unsaturations from 10 to 50 carbon atoms each, a multiple symmetric branched alkyl moiety containing one or more unsaturations from 10 to 50 carbon atoms each, a single asymmetric branched alkyl chain containing one or more unsaturations ranging from 10 to 50 carbons each, a multiple asymmetric branched alkyl chain containing one or more unsaturations ranging from 10 to 50 carbons each, a mixed alkyl chain from 5 to 24 carbon atoms, or an alkenyl chain containing one or more unsaturations from 5 to 24 carbon atoms; $R_2$ is a negatively charged or neutral moiety linking $R_1$ and $R_3$ that is a negatively charged phosphate ester, a neutral phosphonate, a carbamate, an amide, one or more neutral or negatively charged amino acids, an ether, a ketone, an ester, an alkyl chain from one to 10 carbons, or a disulfide linked moiety; and $R_3$ is a negatively charged or neutral moiety having two or more hydroxyls, carbonates, ethers, or carboxylates; or two or more alkyl esters from 1 to 6 carbons; or two or more alkyl esters from 2 to 6 carbons.

In one embodiment, $R_3$ is citrate, isocitrate, aconitate, hydroxycitrate, methylisocitrate, homocitrate, 2-(2,2-dihydroxyethyl)-2-hydroxy-butanedioic acid, 3-ethyl-3-hydroxy-pentanedioic acid, 3-(dihydroxymethyl)-3-hydroxy-pentanedioic acid, 2-hydroxy-2-(ethoxycarbonylmethyl) butanedioic acid, 2-hydroxy-2-(methoxycarbonylmethyl) butanedioic acid, malate, fumarate, tartarate, ethyl citrate, butyl citrate, methyl citrate, 2,3,4-trihydroxy-pentanedioic acid, arabic acid, 2,5-diketogluconate, 5-ketogluconate, oxalomalic acid, fructuronic acid, L,S-citramalic acid, 3-ethylmalate, 3-propylmalate, a moiety shown in FIG. 8, or equivalents thereof.

In another embodiment, the compound is (2S,3S)-2-(((3S, 10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)carbonylamino)ethyl 2,3,4,4-tetrahydroxybutanoate, DPC-1 shown in FIG. 9, or

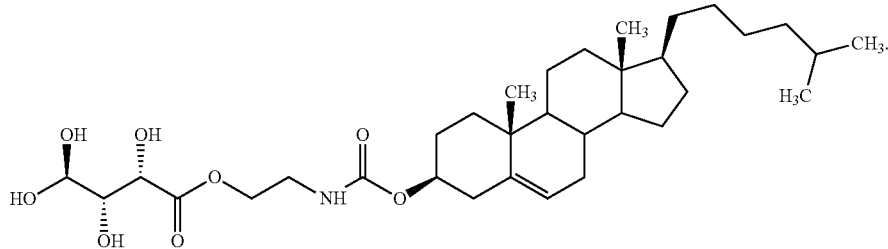

In a further embodiment, the compound is (2S,3S)-((3S, 10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl) 2,3,4,4-tetrahydroxybutanoate, DPC-2 shown in FIG. 10, or

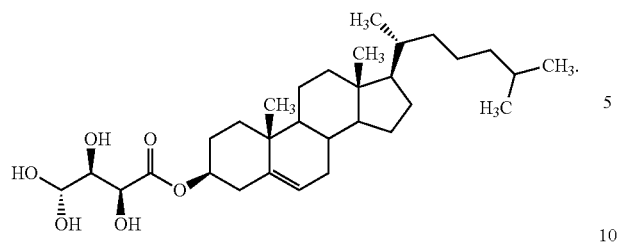
In an additional embodiment, the compound is bis((3S, 10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl) 2,3,4-trihydroxypentanedioate, DPC-3 shown in FIG. 11, or
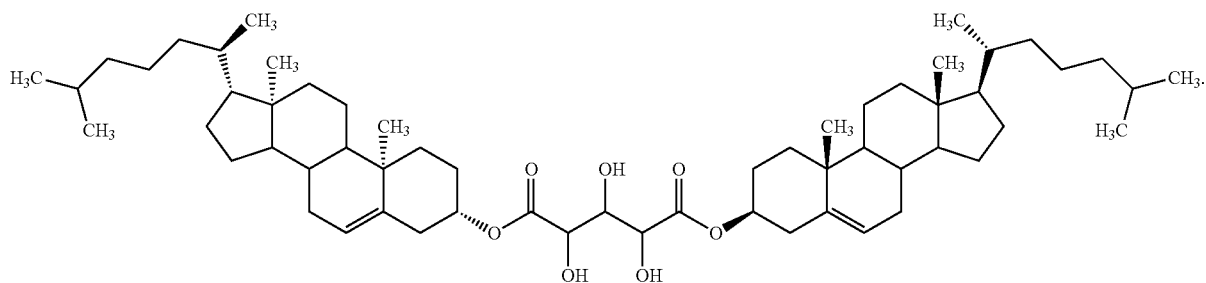 [SMILES: CC(C)CCC[C@@H](C)[C@H]1CCC2C3CC=C4C[C@@H](OC(=O)C(O)C(O)C(O)C(=O)O[C@H]5CC[C@@]6(C)C(=CCC7C6CC[C@@]6(C)C7CC[C@@H]6[C@H](C)CCCC(C)C)C5)CC[C@]4(C)C3CC[C@@]21C]
In certain embodiments, the compound is DPC-12 shown in FIG. 12, or a compound of formula (II):
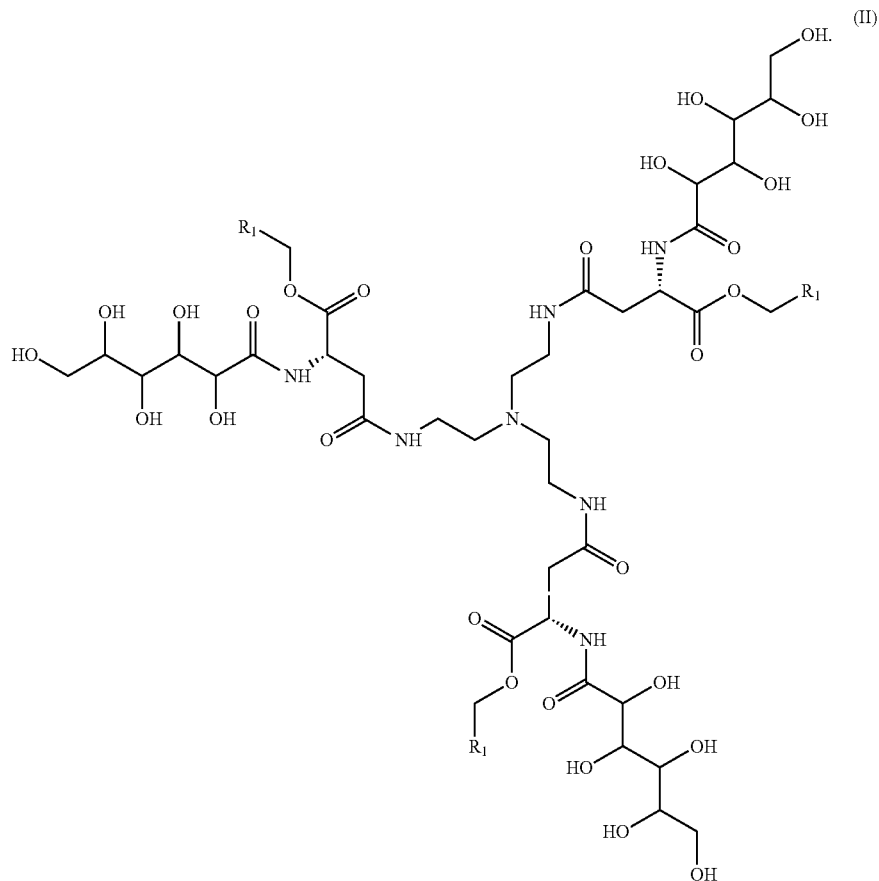

In another embodiment, the compound is (2,4-dihydroxy-6-oxo-6-(pentatriacontan-18-yloxy)hexyloxy)(hydroxy)(oxo)phosphonium, DPC-8 shown in FIG. 13, or

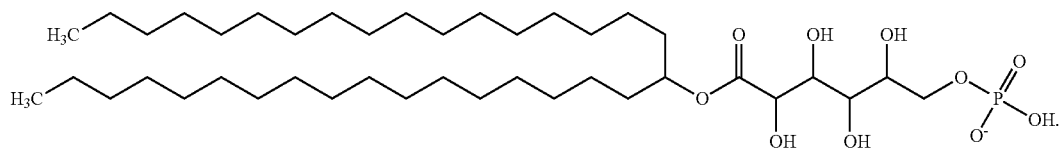 [SMILES: CCCCCCCCCCCCCCCCCC(CCCCCCCCCCCCCCCCC)OC(=O)C(O)C(O)C(O)C(O)COP(=O)([O-])O]

In a further embodiment, the compound is 2,3-bis(oleoyloxy)propyl 2,3,4,5-tetrahydroxy-6-oxidohexyl phosphate, DPC-7 shown in FIG. 13, or

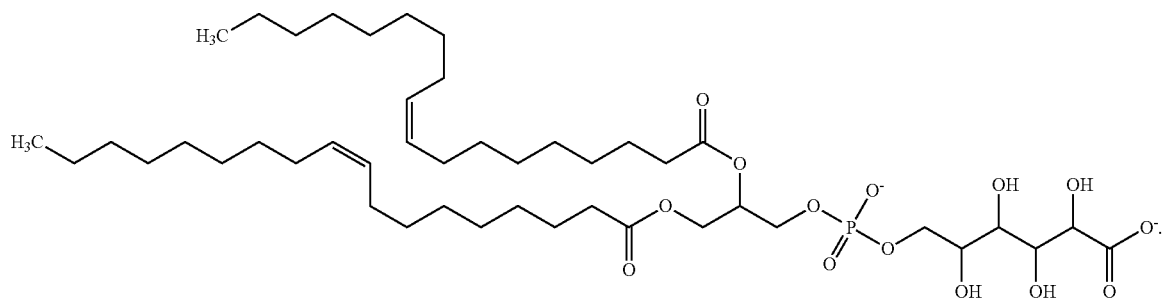

Optionally, the compound is (Z)-2-(oleoyloxy)-3-(palmitoyloxy)propyl 2,3,4,5-tetrahydroxy-6-oxidohexyl phosphate. DPC-6 shown in FIG. 13, or

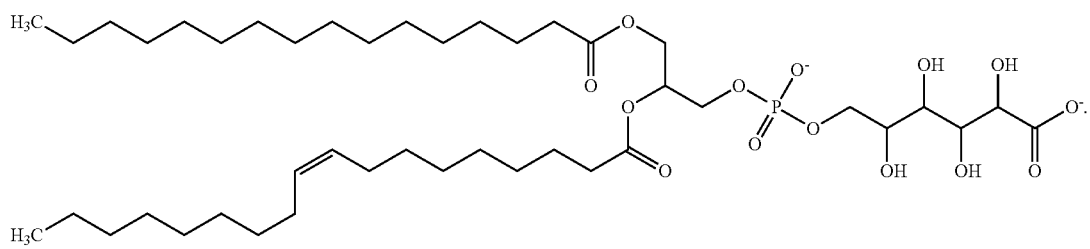

In another embodiment, the compound is 2-(2-(dioctadecylamino)-2-oxoethyl)-2-hydroxysuccinate, DPC-13 shown in FIG. 14, or

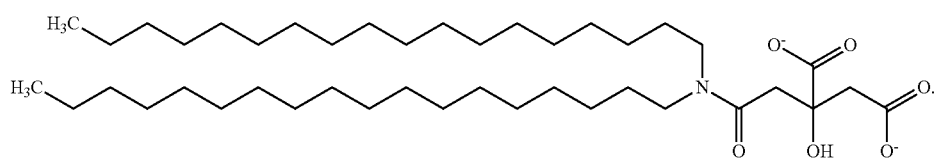 [SMILES: CCCCCCCCCCCCCCCCCCN(CCCCCCCCCCCCCCCCCC)C(=O)CC(O)(CC(=O)[O-])C(=O)[O-]]

In one embodiment, the compound is N,N-(2R,2'R)-3,3'-disulfanediylbis(1-(dioctadecylamino)-1-oxopropane-3,2- diyl)bis(2,3,4,4-tetrahydroxybutanamide), DPC-11 shown in FIG. 14, or

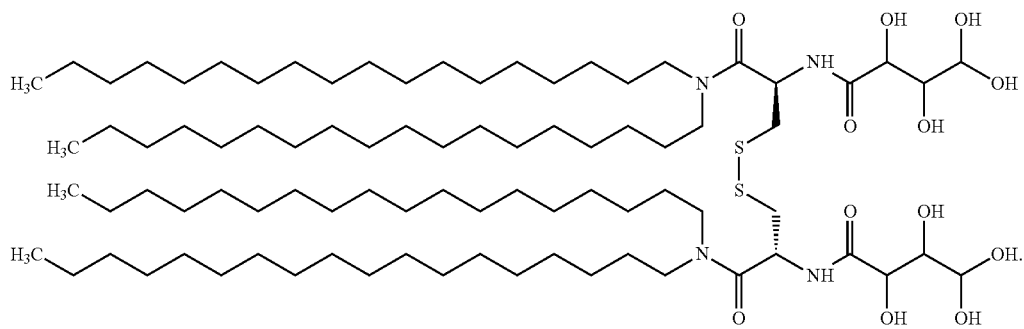 [SMILES: CCCCCCCCCCCCCCCCCCN(CCCCCCCCCCCCCCCCCC)C(=O)[C@H](CSSC[C@H](NC(=O)C(O)C(O)C(O)O)C(=O)N(CCCCCCCCCCCCCCCCCC)CCCCCCCCCCCCCCCCCC)NC(=O)C(O)C(O)C(O)O]

In another embodiment, the compound is (Z)-2-(oleoyloxy)-3-(palmitoyloxy)propyl 2,3,4,5-tetrahydroxy-6-methoxy-6-oxohexyl phosphate, DPC-10 shown in FIG. 14, or

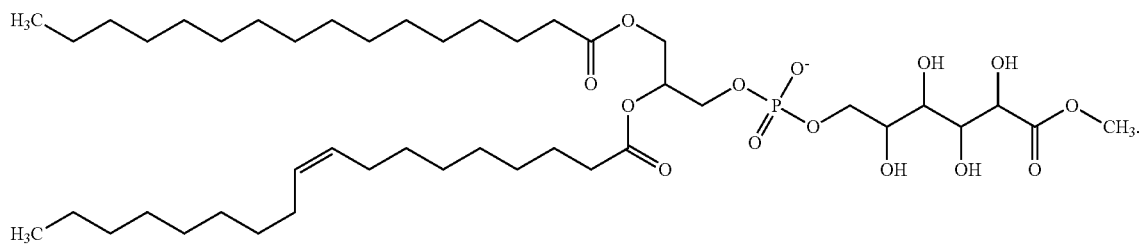 [SMILES: CCCCCCCC/C=C\CCCCCCCC(=O)OC(COC(=O)CCCCCCCCCCCCCCC)COP(=O)([O-])OCC(O)C(O)C(O)C(O)C(=O)OC]

Optionally, the compound is 2,3,4-trihydroxy-N,N-dioctadecyl-5,6-dioxohexanamide, DPC-9 shown in FIG. 14, or

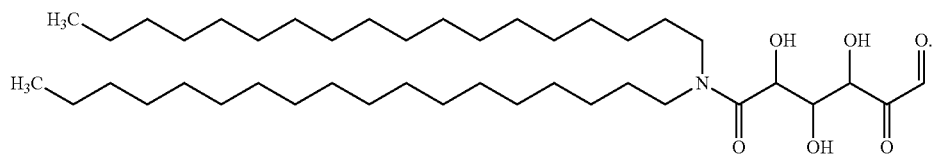 [SMILES: CCCCCCCCCCCCCCCCCCN(CCCCCCCCCCCCCCCCCC)C(=O)C(O)C(O)C(O)C(=O)C=O]

In an additional embodiment, the compound is 2,3,4,4-tetrahydroxy-N,N-dioctadecylbutanamide, DPC-5 shown in FIG. 14 or

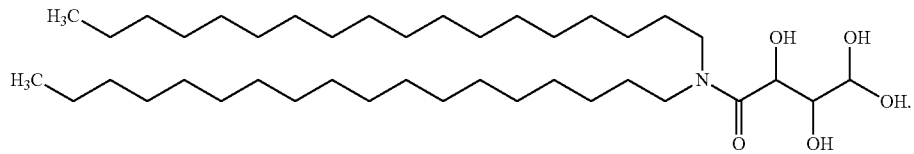 [SMILES: CCCCCCCCCCCCCCCCCCN(CCCCCCCCCCCCCCCCCC)C(=O)C(O)C(O)C(O)O]

In certain embodiments, the compound is 6-(((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)oxidophosphoryloxy)-2,3,4,5-tetrahydroxyhexanoate, DPC-4 shown in FIG. 7, or

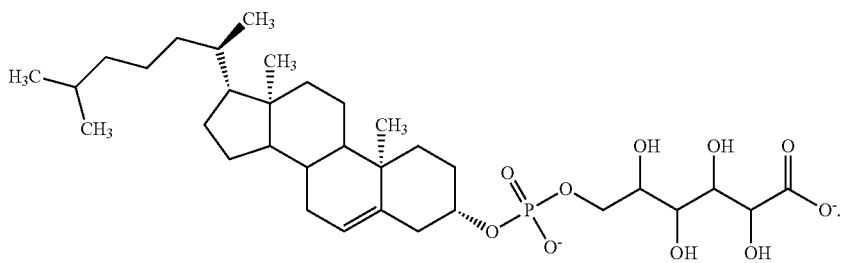

In a further embodiment, the compound is 2,3-bis(stearoyloxy)succinate, DPC-036 shown in FIG. 6, or

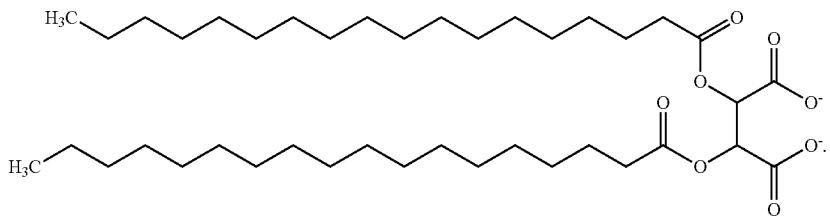

BRIEF DESCRIPTION OF THE DRAWINGS

FIGS. 1-14 show exemplary structures of immune response reducing and/or eliminating lipids for use in formulations of the instant invention.

FIG. 1 shows palmitoyloleyolphosphatidylglycerol (POPG).

FIG. 2 shows dipalmitoylphosphatidylcholine (DPPC).

FIG. 3 shows compound DPC-058 —COOH: 3-((R)-2,5-bis(3-ammoniopropylammonio)pentanamido)-4-(dioctadecylamino)-4-oxobutanoate and compound DPC-056 —COOH: 4-((S)-2,5-bis(3-ammoniopropylammonio)pentanamido)-5-(dioctadecylamino)-5-oxopentanoate.

FIG. 4 shows compound DPC-027: 2-(3-ammoniopropanamido)ethyl 2,3-bis(oleoyloxy)propyl phosphate.

FIG. 5 shows compound DPC-033: 2-(3-ammoniopropanamido)ethyl 2,3-bis(oleoyloxy)propyl phosphate.

FIG. 6 shows compound DPC-036: 2,3-bis(stearoyloxy)succinate.

FIG. 7 shows the generic formula of the immune response reducing lipids of the invention, including compound DPC-4: 6-(((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)oxidophosphoryloxy)-2,3,4,5-tetrahydroxyhexanoate.

FIG. 8 shows exemplary lipid head groups useful in the compounds of the invention. It is contemplated that methoxy-, ethoxy- and propoxy-derivatives of these exemplary lipid head groups can also be useful in the compounds of the invention.

FIG. 9 shows compound DPC-1: (2S,3S)-2-(((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)carbonylamino)ethyl 2,3,4,4-tetrahydroxybutanoate.

FIG. 10 shows compound DPC-2: (2S,3S)-((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl) 2,3,4,4-tetrahydroxybutanoate.

FIG. 11 shows compound DPC-3: bis((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl) 2,3,4-trihydroxypentanedioate.

FIG. 12 shows formula DPC-12.

FIG. 13 shows compound DPC-6: (Z)-2-(oleoyloxy)-3-(palmitoyloxy)propyl 2,3,4,5-tetrahydroxy-6-oxidohexyl phosphate; compound DPC-7: 2,3-bis(oleoyloxy)propyl 2,3,4,5-tetrahydroxy-6-oxidohexyl phosphate; and compound DPC-8: (2,4-dihydroxy-6-oxo-6-(pentatriacontan-18-yloxy)hexyloxy)(hydroxy)(oxo)phosphonium.

FIG. 14 shows compound DPC-5: 2,3,4,4-tetrahydroxy-N,N-dioctadecylbutanamide; DPC-9: 2,3,4-trihydroxy-N,N-dioctadecyl-5,6-dioxohexanamide; compound DPC-10: (Z)-2-(oleoyloxy)-3-(palmitoyloxy)propyl 2,3,4,5-tetrahydroxy-6-methoxy-6-oxohexyl phosphate; compound DPC-11: N,N'-(2R,2'R)-3,3'-disulfanediylbis(1-(dioctadecylamino)-1-oxopropane-3,2-diyl)bis(2,3,4,4-tetrahydroxybutanamide); compound DPC-13: 2-(2-(dioctadecylamino)-2-oxoethyl)-2-hydroxysuccinate; compound DPC-25.

DETAILED DESCRIPTION OF THE INVENTION

Figure 1:
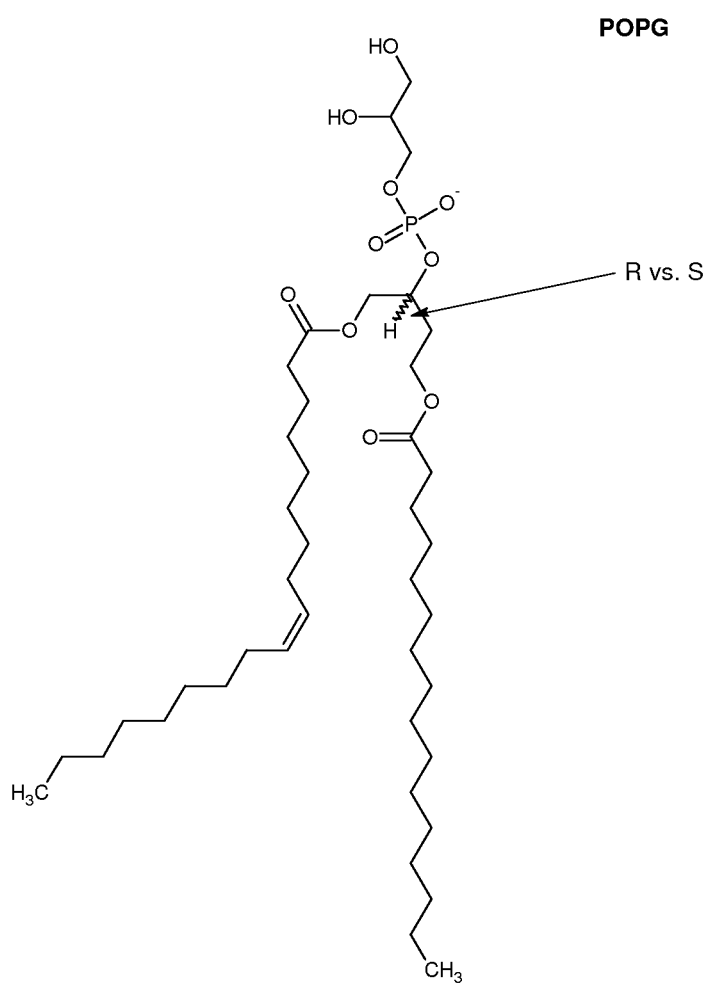
Figure 2:
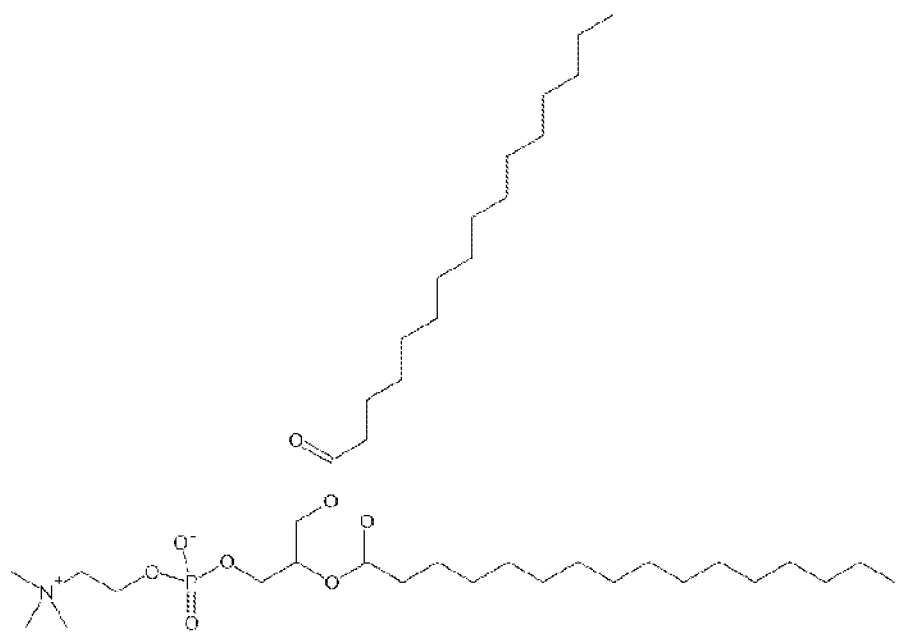
Figure 3:
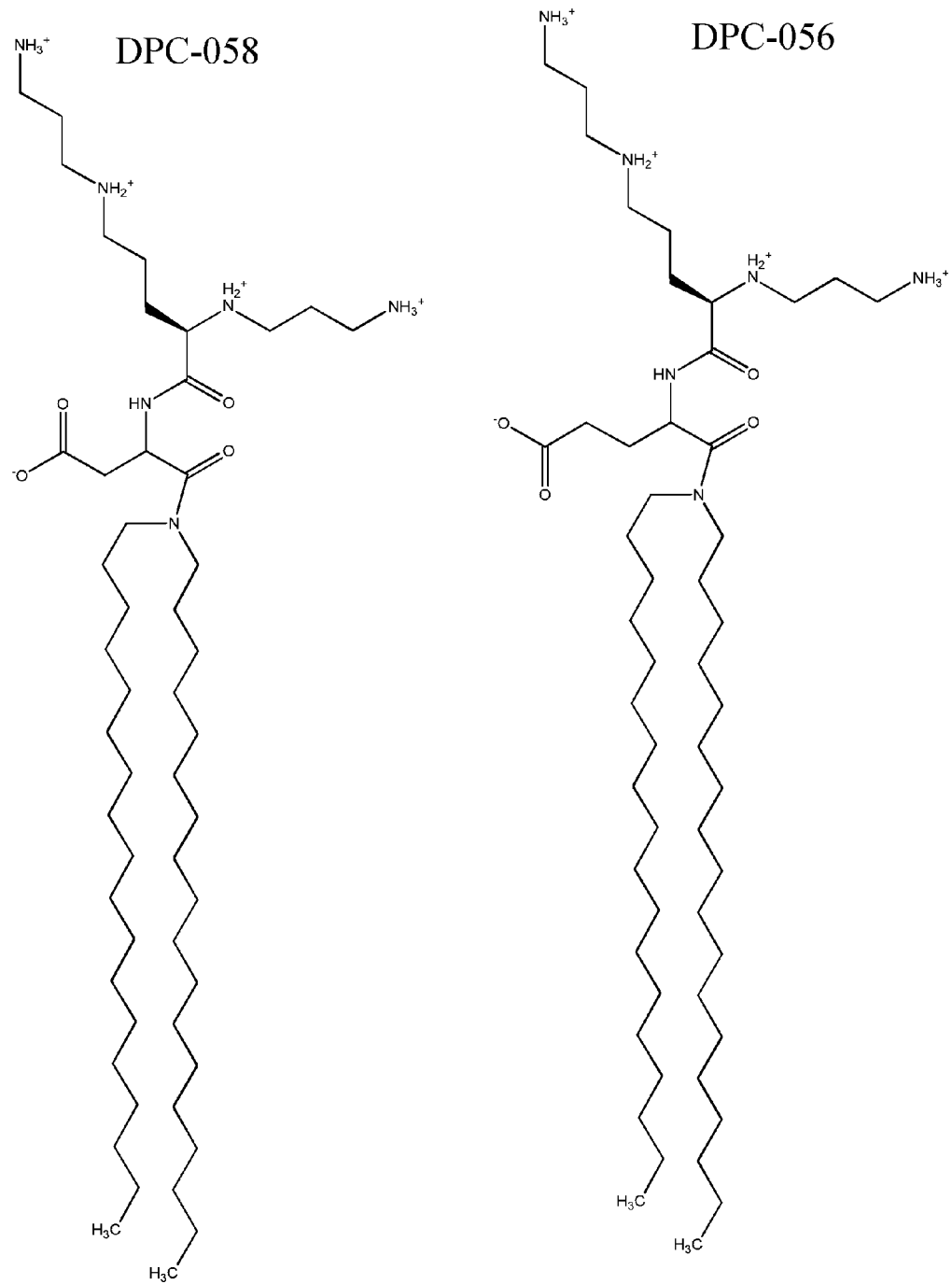
Figure 4:
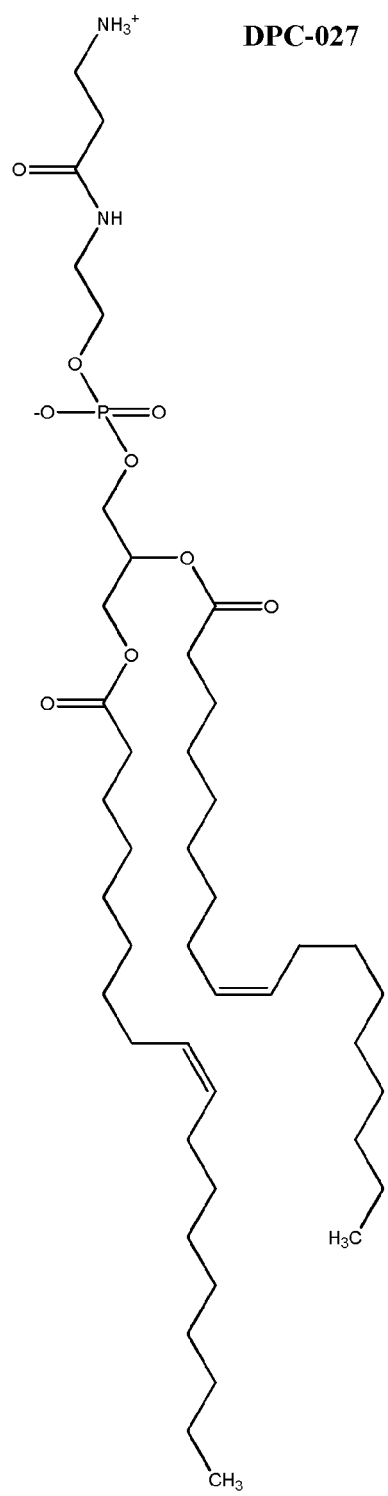
Figure 5:
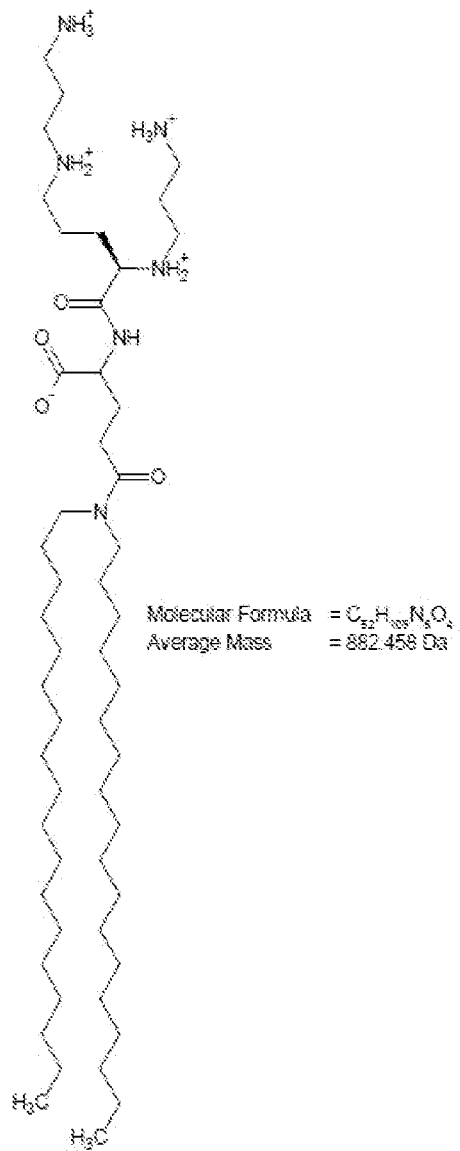

The formulations of the instant invention contain an immunogenic or immunostimulatory cargo, delivery moiety and/or lipid, and a lipidic component (e.g., a non-cationic lipid or lipid-conjugate) that functions to reduce or prevent induction in a mammalian subject of an immune response which would otherwise occur when the immunogenic or immunostimulatory (e.g., immunologic adjuvant) cargo, delivery moiety and/or lipid is administered to a mammal subject as a component of an appropriate control formulation that lacks the immune response reducing lipid.

In one aspect, the immunogenic or immunostimulatory cargo is a nucleic acid (e.g., single- and double-stranded nucleic acids and nucleic acid analogs, including RNA and analogs, DNA and analogs, and nucleic acid mimics or other modifications of oligonucleotides. In certain embodiments, the nucleic acid is a double stranded RNA (dsRNA) with or without modified and/or unnatural modifications or substitutions and/or conjugates. The dsRNAs of the instant invention possess the ability to reduce or inhibit target gene expression via use of the RNA interference (RNAi) pathway. In certain such embodiments, one of the strands of the dsRNA contains a region of nucleotide sequence that has a length that ranges from about 19 to about 35 or more nucleotides that can direct the destruction and/or translational inhibition of the target gene transcript.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "subject" is meant an organism, which is a donor or recipient of explanted cells or the cells themselves. "Subject" also refers to an organism to which the formulations of the invention can be administered. A subject can be a mammal or mammalian cells, including a human or human cells.

The term "mammalian subject" refers to both humans and to warm blooded animals, such as laboratory animals, e.g., rodents (e.g., mice and rats) and non-human primates, domestic animals, e.g., cats and dogs, and farm animals, e.g., cattle, pigs, goats and sheep.

The mechanism by which the immune system controls disease includes the induction of neutralising antibodies via humoral immunity and the generation of T-cell responses via cellular immunity. As used herein, the term "immune response" refers to the reactivity of an organism's immune system in response to an antigen. In vertebrates, this may involve antibody production, induction of cell-mediated immunity, and/or complement activation (e.g., phenomena associated with the vertebrate immune system's prevention and resolution of infection by microorganisms).

Accordingly, in certain embodiments, the term "immune response" in reference to a dsRNA formulation refers to the activation and functioning of an innate immune response within a mammalian subject administered a formulated dsRNA (e.g., a dsRNA formulation of the invention), and to development in a mammalian subject administered a dsRNA formulation of a humoral and/or a cellular (cell mediated) immune response against that dsRNA formulation.

The term "immune response reducing" or "reducing an immune response" as used herein includes lowering and/or preventing the activation of the molecular machinery and cell types that participate in immune reactions and enhancement of an immune response to a specific antigenic substance—in certain aspects of the instant invention, the antigenic substance is a peptide, protein, nucleic acid, carbohydrate, lipid or other excipient; in certain embodiments of the instant invention, the antigenic substance is a dsRNA molecule or associated antigenic agent of a dsRNA formulation (e.g., a cationic lipid or a delivery moiety), including any derivatives therefrom (e.g., ssRNAs derived from the formulated dsRNAs). As such, an immune response reduced dsRNA formulation of the invention is one that possesses a reduced or ablated capacity for activating the molecular machinery and/or cell types that participate in immune reactions and enhancement of an immune response to the dsRNA formulation (specifically, as compared to an appropriate control dsRNA formulation that lacks immune response reducing lipids in accordance with the dsRNA formulations of the instant invention). While not wishing to be bound by theory, an immune response that is stimulated by an immunostimulatory nucleic acid formulation (e.g., dsRNA formulations not possessing the immune response reducing lipids of the instant invention) is generally a "Th1-type" immune response, as opposed to a "Th2-type" immune response. Th1-type immune responses are normally characterized by "delayed-type hypersensitivity" reactions to an antigen and activated macrophage function and can be detected at the biochemical level by increased levels of Th1-associated cytokines such as IFN-γ, IL-2, IL-12, and TNF-β. Th2-type immune responses are generally associated with high levels of antibody production, especially IgE antibody production and enhanced eosinophils numbers and activation, as well as expression of Th2-associated cytokines such as IL-4, IL-5 and IL-13.

The term "innate immune response" or "innate immunity" as used herein includes a variety of innate resistance mechanisms by which a cell or individual recognizes and responds to the presence of a pathogen (e.g., unmethylated and/or unnatural DNA and/or RNA and nucleic acid analogs, peptides, proteins, liposaccharides or other lipids recognized by the immune system as foreign). As used herein, an "innate immune response" includes the intracellular and intercellular events and reactions that occur when the cell recognizes pathogen associated molecular patterns or signals. Cellular receptors active in an innate immune response include a family of cell surface and endosomal Toll-like receptors (TLRs). Ligands derived from pathogenic organisms and intracellular ligands have been identified for several TLRs, as described herein. Innate immune responses can occur in cells that are not identified as being part of the normal immune system (e.g., the PKR response).

As used herein, the term "cell mediated immune (CMI) response" is one mediated by T-lymphocytes and/or other white blood cells. Without wishing to be bound by theory, the CMI immune mechanisms are generally more effective against intracellular infections and disease because the CMI mechanisms prime T cells in a way that, when a target antigen appears at a later date, memory T cells are activated to result in a CMI response that destroys target cells that have the corresponding target antigen or a portion thereof on their cell surfaces, and thereby the infecting pathogen. The CMI response is focused on the destruction of the source of infection mediated by either effecter cells that destroy infected cells of the host by direct cell-to-cell contact and/or by the release of molecules, such as cytokines, that possess anti-viral activity. Thus, the CMI response, which is characterized by a specific T lymphocyte cellular response, is crucial to produce resistance to diseases caused by cancer, viruses, pathogenic and other intracellular microorganisms.

As used herein, the term "humoral immune response" refers to an immune response mediated by antibody molecules. The antibodies generated by humoral immunity are primarily effective against extracellular infectious agents.

The term "cytokine response" refers to antigen-induced cytokine secretion by lymphocytes as measured for instance by assaying culture supernatants for cytokine content; (e.g. IL-2, IFNγ, TNFα, IL-4, etc) by ELISA. The term "antibody response" refers to the production of antibodies (e.g. IgM, IgA, IgG) that bind to an antigen of interest, this response is measured for instance by assaying sera by antigen ELISA or western blot (serum antibody response). Similarly, a mucosal antibody response is measured for instance by assaying mucosal washes or secretions (e, g, bronchial ravage, urine, stool, saliva, tears, etc.) by antigen ELISA.

The terms "immunogenic" and "immunologic" refer to the ability of an agent (e.g., a cargo nucleic acid, peptide or protein, or a delivery moiety) or a substance (e.g., a lipid) to produce at least one element of an immune response. The immune response is the total response of the body of an animal to the introduction of an antigen and comprises multiple elements including antibody formation (humoral response or humoral immunity), cellular immunity, hypersensitivity, or immunological tolerance. Cellular immunity refers to cellular responses elicited by an antigen and include a T-helper cell- and/or CTL-response and/or stimulated cytokine production.

As used herein, the term "immunostimulatory" is used in reference to an agent or substance capable of inducing and/or enhancing an immune response.

The term "adjuvant" as used herein refers to any compound which, when injected together with an antigen, non-specifically enhances the immune response to that antigen.

Without being bound by theory, suppression of the adjuvant properties otherwise possessed by a peptide, protein, nucleic acid (e.g., dsRNA), carbohydrate, cationic lipid, delivery moiety and/or excipient of the formulations of the invention is advantageous because the adjuvant may enhance the CMI or other immunologic response to, e.g., an immunogenic formulation/delivery moiety, by diverting the Th2 response to a Th1 response and/or specific effecter associated mechanisms to the immunogenic delivery moiety with the consequent generation and maintenance of an enhanced CMI response to the immunogenic delivery moiety (see, for example, the teachings in WO 97/02045).

Whether a molecule (e.g., a dsRNA, cationic lipid, peptide, protein, carbohydrate, delivery moiety, excipient, etc.) is acting as an adjuvant can be determined by administering the molecule with an antigenic/immunogenic moiety in parallel with the antigenic/immunogenic moiety alone to animals and comparing antibody and/or cellular-mediated immunity in the two groups using standard assays such as radioimmunoassay, ELISAs, CDS+ T-cell assays, and the like, all well known in the art.

As used herein, the term "nucleic acid adjuvant" refers to an adjuvant comprising a nucleotide sequence and which, when administered with an antigenic/immunogenic moiety enhances the CMI response relative to the CMI response generated upon administration of the antigenic/immunogenic moiety alone.

As used herein, the term "delivery moiety" is a moiety that is capable of enhancing the ability of an associated or attached composition to associate with, bind, or enter a cell, cell of a tissue or subject, cell type, tissue or location within a subject, either in vitro or in vivo. In certain embodiments, delivery moieties are polypeptides, carbohydrates or lipids. Exemplary delivery moieties include tumor targeting moieties, such as somatostatin (sst2), bombesin/GRP, luteinizing hormone-releasing hormone (LHRH), neuropeptide Y (NPY/Y1), neurotensin (NT1), vasoactive intestinal polypeptide (VIP/VPAC1) and cholecystokinin (CCK/CCK2). In certain embodiments, a delivery moiety is non-covalently associated with a formulation of the invention. In other embodiments, a delivery moiety is attached to a lipid of a formulation of the invention, and is optionally covalently attached. In further embodiments, a delivery moiety is attached to an immune response reducing lipid of a formulation of the invention, and is optionally covalently attached. In additional embodiments, a delivery moiety is attached to a cargo (e.g., a dsRNA, small molecule, peptide or other agent) of a formulation of the invention, optionally covalently.

A cargo of a formulation of the invention can be a pharmaceutical, protein, peptide, hormone, cytokine, antigen, small molecule, etc., e.g., a nucleic acid, active drug molecule (e.g., small molecule) or vehicle component. Non-limiting specific examples of such cargoes include siRNA, DsiRNA, antisense oligonucleotides, peptide hormones, steroid hormones, and cytotoxic agents such as camptothecin, SN-38, homo-campotothecin (BN80915), paclitaxel, doxorubicin, and methotrexate.

The term "excipient" refers to a non-therapeutic agent added to a pharmaceutical composition to provide a desired consistency or stabilizing effect. Examples, without limitation, of excipients include polyethoxylated castor oil (Cremophor EL™, BASF, Parsippany, N.J.), calcium carbonate, calcium phosphate, various sugars and types of starch, cellulose derivatives, gelatin, vegetable oils and polyethylene glycols.

The term "amphipathic compound" refers to any suitable material containing both hydrophobic and hydrophilic moieties or regions. A subgroup of such compounds comprises "lipids." Hydrophilic characteristics derive from the presence of phosphato, carboxylic, sulfato, amino, sulfhydryl, nitro, carbohydrate, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group(s). Optional amphipathic compounds are phospholipids such as phosphoglycerides. "Phospholipids" are a group of lipids having both phosphate group and one or more acyl groups. "Phosphoglycerides" are based on glycerol, wherein the three hydroxyl groups are esterified with two acyl groups and a phosphate group, which itself may be bound to one of a variety of simple organic groups. The two acyl groups can be identical, of similar length, or different. Representative examples of which include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds, such as sphingolipids, glycosphingolipids, triglycerides, and sterols are also amphipatic compounds.

The term "cationic lipid" refers to any of a number of lipid species which carry a net positive charge at physiological pH. In certain embodiments, a physiological pH is pH 6.5-7.5. In certain embodiments, a physiological pH includes pH values that range as low as those found in late-stage endosomes. In such embodiments, a physiological pH can include pH values in the range of pH 5.0-8.0, optionally, pH 5.0-7.5 or pH 5.0-7.0, including, e.g., pH 5.5-7.0 or pH 5.5-6.5. A number of cationic lipids and related analogs, which are also useful in the present invention, have been described in U.S. Patent Publication No. 20060083780; U.S. Pat. Nos. 5,208,036; 5,264,618; 5,279,833; 5,283,185; 5,753,613; and 5,785,992; and PCT Publication No. WO 96/10390. Examples of cationic lipids include, but are not limited to, N,N-dioleyl-N,N-dimethylammonium chloride (DODAC), dioctadecyldimethylammonium (DODMA), distearyldimethylammonium (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 1,2-dilinoleyloxy-N,N-dimethylaminopropane (DLinDMA), 1,2-dilinolenyloxy-N,N-dimethylaminopropane (DLenDMA), and mixtures thereof. As a non-limiting example, cationic lipids that have a positive charge below physiological pH include, but are not limited to, DODAP, DODMA, and DSDMA. In some cases, the cationic lipids comprise a protonatable tertiary amine head group, C18 alkyl chains, ether linkages between the head group and alkyl chains, and 0 to 3 double bonds. Such lipids include, e.g., DSDMA, DLinDMA, DLenDMA, and DODMA. The cationic lipids may also comprise ether linkages and pH titratable head groups. Such lipids include, e.g., DODMA.

The term "neutral lipid" refers to any of a number of lipid species that exist either in an uncharged or neutral zwitterionic form at physiological pH. Such lipids include, for example cholesterol, DOPE, DLPE, DLPC, phosphatidylcholines, phosphatidylethanolamines, phosphatidylserines, ceramide, sphingomyelin, cephalin, and cerebrosides.

The term "non-cationic lipid" refers to any neutral lipid as described above as well as anionic lipids.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), dipalmitoylphosphatidylcholine (DPPC), the preponderance of lipids of FIGS. 1-14, and other anionic modifying groups joined to neutral lipids.

The term "liposome" encompasses any compartment enclosed by a lipid bilayer or a lipidic particle. Some liposomes are also referred to as lipid vesicles. In order to form a liposome the lipid molecules comprise elongated non-polar (hydrophobic) portions and polar (hydrophilic) portions. The hydrophobic and hydrophilic portions of the molecule are optionally positioned at two ends of an elongated molecular structure. When such lipids are dispersed in water they may spontaneously form bilayer membranes referred to as lamellae. The lamellae are composed of two monolayer sheets of lipid molecules with their non-polar (hydrophobic) surfaces facing each other and their polar (hydrophilic) surfaces facing the aqueous medium. The membranes formed by the lipids enclose a portion of the aqueous phase in a manner similar to that of a cell membrane enclosing the contents of a cell. Thus, the bilayer of a liposome has similarities to a cell membrane without the protein components present in a cell membrane. As used in connection with the present invention, the term liposome includes multilamellar liposomes, which generally have a diameter in the range of 1 to 10 micrometers and are comprised of anywhere from two to hundreds of concentric lipid bilayers alternating with layers of an aqueous phase, and also includes unilamellar vesicles which are comprised of a single lipid layer and generally have a diameter in the range of about 20 to about 400 nanometers (nm), about 50 to about 300 nm, about 300 to about 400 nm, about 100 to about 200 nm, which vesicles can be produced by subjecting multilamellar liposomes to ultrasound, by extrusion under pressure through membranes having pores of defined size, or by high pressure homogenization.

The term "nanoparticle" as used herein denotes a carrier structure which is biocompatible with and sufficiently resistant to chemical and/or physical destruction by the environment of use such that a sufficient amount of the nanoparticles remain substantially intact after injection into the blood stream, given intraperitoneally or orally or incubated with an in vitro sample so as to be able to reach the cytoplasm of a target cell or some other cellular structure. Biodegradation of the nanoparticle is permissible upon association with a target cell, or upon entry of a cargo (e.g., small molecule drug, nucleic acid, etc.) into a target cell's endocytic, pinocytic and/or phagocytic pathways, or the cell's cytoplasm or other compartments. Nanoparticles can be liposomes, micelles, etc., including, e.g., solid colloidal particles ranging in size from 1 to 1000 nm. Nanoparticles can have any diameter less than or equal to 1000 nm, including 5, 10, 15, 20, 25, 30, 50, 100, 500 and 750 nm. Drugs (e.g., small molecules, nucleic acids, etc.), active agents, bioactive or other relevant materials can be incubated with the nanoparticles, and thereby be adsorbed or attached to the nanoparticle.

The formulations of the instant invention are designed to reduce the immune response of a subject to such formulations, as compared to the immune response observed for such a formulation in the absence of an immune response reducing lipid, while retaining activity, potency and/or duration of effect of the cargo of such formulations. The ability of a formulation of the invention to reduce or prevent the immune response of a subject to such formulation (as compared to an appropriate control formulation lacking a non-cationic immune response reducing lipid) can be evaluated by a number of methods described elsewhere herein. In certain embodiments, such formulations of the invention are deemed to be effective at reducing the immune response of a subject to such a formulation if the formulation comprising a non-cationic lipid or lipid-conjugate capable of reducing or preventing an immune response to an associated formulated agent in a mammalian subject reduces the immune response of a subject by at least 10% (measured by one or more metrics of immune response as described elsewhere herein), as compared to an appropriate control formulation lacking the non-cationic lipid. In certain other embodiments, a formulation of the invention is deemed to be effective if such a formulation reduces the immune response of a subject by at least 20%, at least 30%, at least 40%, at least 50%, at least 60%, at least 70%, at least 80%, at least 90%, at least 95%, at least 96%, at least 97%, at least 98%, at least 99%, at least 99.5%, at least 99.9% (measured by one or more metrics of immune response as described elsewhere herein), or entirely prevents induction of an immune response in a subject to said formulation (including any immunogenic or immunostimulatory component of such formulation), as compared to an appropriate control formulation lacking the non-cationic lipid.

In certain embodiments of the invention, an immune response reducing lipid is a cationic lipid. While many cationic lipids have been identified as capable of triggering an immune response in a subject, it is envisioned that such immune response stimulating effects of cationic lipids may be masked or eliminated by restructuring the cationic lipid to effectively mask and/or prevent the cationic charge of the lipid from coming into contact with components/receptors of the subject's immune system. For example, it is contemplated that the following head group structure, which harbors a cationic charge, is sterically prevented from inducing an immune response in a subject when used as a component of a lipid that remains a cationic lipid:

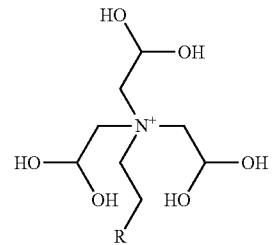

In the above structure, R is optionally selected from alkyl (e.g., an alkyl "tail"), cholesterol, or other such group. In certain embodiments, lipids comprising cation-masking structures (e.g., sterically hindered head groups and/or otherwise buried cations) can function in a manner that is immune response reducing, thereby paralleling the immune response reducing activity described herein for certain non-cationic lipids. Further exemplary masking head groups include trimethyl- and triethyl-citrate head groups, which can optionally be conjugated at a single point to cationic residues and lipidic structures to form cationic lipids in which such cationic charges are effectively masked.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

In certain embodiments, the phrase "consists essentially of" is used in reference to the formulations of the invention. In some such embodiments, "consists essentially of" refers to a composition that comprises a dsRNA formulation of the invention which possesses at least a certain level of target gene inhibitory activity (e.g., at least 50% target gene inhibitory activity) and that also comprises one or more additional components and/or modifications that do not significantly impact the target gene inhibitory activity of the dsRNA formulation. For example, in certain embodiments, a composition "consists essentially of" a dsRNA formulation of the invention where modifications of the dsRNA and/or dsRNA-associated components of the formulation of the invention do not alter the target gene inhibitory activity (optionally including potency or duration of target gene inhibitory activity) by greater than 3%, greater than 5%, greater than 10%, greater than 15%, greater than 20%, greater than 25%, greater than 30%, greater than 35%, greater than 40%, greater than 45%, or greater than 50% relative to the dsRNA formulation of the invention in isolation. In certain embodiments, a composition is deemed to consist essentially of a dsRNA formulation of the invention even if more dramatic reduction of target gene inhibitory activity (e.g., 80% reduction, 90% reduction, etc. in efficacy, duration and/or potency) occurs in the presence of additional components or modifications, yet where target gene inhibitory activity is not significantly elevated (e.g., observed levels of target gene inhibitory activity are within 10% those observed for the isolated dsRNA formulations of the invention) in the presence of additional components and/or modifications.

Therapeutic cargoes/payloads, formulation components and functional excipients may include double-stranded RNA. Double-stranded RNA, such as the dsRNAs of the formulations of the instant invention, has different properties than single-stranded RNA, double-stranded DNA or single-stranded DNA. Each of the species of nucleic acids is bound by mostly non-overlapping sets of binding proteins in the cell and degraded by mostly non-overlapping sets of nucleases. The nuclear genome of all cells is DNA-based and as such is unlikely to produce immune responses except in autoimmune disease (Pisetsky. *Clin Diagn Lab Immunol*. 1998 January; 51:1-6). Single-stranded RNA (ssRNA) is the form endogenously found in eukaryotic cells as the product of DNA transcription. Cellular ssRNA molecules include messenger RNAs (and the progenitor pre-messenger RNAs), miRNAs, small nuclear RNAs, small nucleolar RNAs, transfer RNAs and ribosomal RNAs. Single-stranded RNA can induce interferon and inflammatory immune response via TLR7 and TLR8 receptors (*Proc Natl Acad. Sci.* 2004. 101:5598-603; Science. 2004. 303:1526-9; Science. 2004. 303:1529-3). Double-stranded RNA can induce a size-dependent immune response such that dsRNA larger than 30 bp activates the interferon response, while shorter dsRNAs tend to avoid at least the PKR-mediated pathway of immune response. MicroRNAs (miRNAs), including short temporal RNAs and small modulatory RNAs, are types of cellular dsRNA molecules in mammals that were not discovered until 2001 (Kim. 2005. *Mol. Cells.* 19:1-15). Responses to extracellular RNA in the bloodstream, double- or single-stranded of any length, include rapid excretion by the kidneys and degradation by enzymes (*PLOS Biol.* 2004. 2:18-20).

As used herein, the term "nucleic acid" refers to deoxyribonucleotides, ribonucleotides, or modified nucleotides, and nucleotide analogs and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

As used herein, "nucleotide" is used as recognized in the art to include those with natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, e.g., Usman and McSwiggen, supra; Eckstein, et al., International PCT Publication No. WO 92/07065; Usman et al, International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include, hypoxanthine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine and uracil at 1' position or their equivalents.

As used herein, "modified nucleotide" or "nucleoside analog" refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications of nucleotides include those naturally occurring that result from modification by enzymes that modify nucleotides, such as methyltransferases. Modified nucleotides also include synthetic or non-naturally occurring nucleotides. Synthetic or non-naturally occurring modifications in nucleotides include those with 2' modifications, e.g., 2'-methoxyethoxy, 2'-fluoro, 2'-allyl, 2'-O-[2-(methylamino)-2-oxoethyl], 4'-thio, bridge, 4'-$(CH_2)_2$—O-2'-bridge, 2'-LNA, and 2'-O—(N-methylcarbamate) or those comprising base analogs. In connection with 2'-modified nucleotides as described for the present disclosure, by "amino" is meant 2'-$NH_2$ or 2'-O—$NH_2$, which can be modified or unmodified. Such modified groups are described, e.g., in Eckstein et al., U.S. Pat. No. 5,672,695 and Matulic-Adamic et al., U.S. Pat. No. 6,248,878.

In reference to the nucleic acid molecules of the present disclosure, modifications may exist upon these agents in patterns on one or both strands of the double stranded ribonucleic acid (dsRNA). As used herein, "alternating positions" refers to a pattern where every other nucleotide is a modified nucleotide or there is an unmodified nucleotide (e.g., an unmodified ribonucleotide) between every modified nucleotide over a defined length of a strand of the dsRNA (e.g., 5'-MNMNMN-3'; 3'-MNMNMN-5'; where M is a modified nucleotide and N is an unmodified nucleotide). The modification pattern starts from the first nucleotide position at either the 5' or 3' terminus according to a position numbering convention, e.g., as described herein (in certain embodiments, position 1 is designated in reference to the terminal residue of a strand following a projected Dicer cleavage event of a dsRNA agent of a formulation of the invention; thus, position 1 does not always constitute a 3' terminal or 5' terminal residue of a pre-processed agent of a formulation of the invention). The pattern of modified nucleotides at alternating positions may run the full length of the strand, but in certain embodiments includes at least 4, 6, 8, 10, 12, 14 nucleotides containing at least 2, 3, 4, 5, 6 or 7 modified nucleotides, respectively. As used herein, "alternating pairs of positions" refers to a pattern where two consecutive modified nucleotides are separated by two consecutive unmodified nucleotides over a defined length of a strand of the dsRNA (e.g., 5'-MMNNMMNNMMNN-3'; 3'-MMNNMMNNMMNN-5'; where M is a modified nucleotide and N is an unmodified nucleotide). The modification pattern starts from the first nucleotide position at either the 5' or 3' terminus according to a position numbering convention such as those described herein. The pattern of modified nucleotides at alternating positions may run the full length of the strand, but optionally includes at least 8, 12, 16, 20, 24, 28 nucleotides containing at least 4, 6, 8, 10, 12 or 14 modified nucleotides, respectively. It is emphasized that the above modification patterns are exemplary and are not intended as limitations on the scope of the invention.

As used herein, "base analog" refers to a heterocyclic moiety which is located at the 1' position of a nucleotide sugar moiety in a modified nucleotide that can be incorporated into a nucleic acid duplex (or the equivalent position in a nucleotide sugar moiety substitution that can be incorporated into a nucleic acid duplex). In dsRNAs of the formulations of the invention, a base analog is generally either a purine or pyrimidine base excluding the common bases guanine (G), cytosine (C), adenine (A), thymine (T), and uracil (U). Base analogs can duplex with other bases or base analogs in dsRNAs. Base analogs include those useful in the formulations, compounds and methods of the invention, e.g., those disclosed in U.S. Pat. Nos. 5,432,272 and 6,001,983 to Benner and US Patent Publication No. 20080213891 to Manoharan, which are herein incorporated by reference. Non-limiting examples of bases include hypoxanthine (I), xanthine (X), 3β-D-ribofuranosyl-(2,6-diaminopyrimidine) (K), 3β-D-ribofuranosyl-(1-methyl-pyrazolo[4,3-d]pyrimidine-5,7(4H,6H)-dione) (P), iso-cytosine (iso-C), iso-guanine (iso-G), 1β-D-ribofuranosyl-(5-nitroindole), 1-β-D-ribofuranosyl-(3-nitropyrrole), 5-bromouracil, 2-aminopurine, 4-thio-dT, 7-(2-thienyl)-imidazo[4,5-b]pyridine (Ds) and pyrrole-2-carbaldehyde (Pa), 2-amino-6-(2-thienyl)purine (S), 2-oxopyridine (Y), difluorotolyl, 4-fluoro-6-methylbenzimidazole, 4-methylbenzimidazole, 3-methyl isocarbostyrilyl, 5-methyl isocarbostyrilyl, and 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenzyl, tetracenyl, pentacenyl, and structural derivates thereof (Schweitzer et al., J. Org. Chem., 59:7238-7242 (1994); Berger et al., Nucleic Acids Research, 28(15):2911-2914 (2000); Moran et al., J. Am. Chem. Soc., 119:2056-2057 (1997); Morales et al., J. Am. Chem. Soc., 121:2323-2324 (1999); Guckian et al., J. Am. Chem. Soc., 118:8182-8183 (1996); Morales et al., J. Am. Chem. Soc., 122(6):1001-1007 (2000); McMinn et al., J. Am. Chem. Soc., 121:11585-11586 (1999); Guckian et al., J. Org. Chem., 63:9652-9656 (1998); Moran et al., Proc. Natl. Acad. Sci., 94:10506-10511 (1997); Das et al., J. Chem. Soc., Perkin Trans., 1:197-206 (2002); Shibata et al., J. Chem. Soc., Perkin Trans., 1: 1605-1611 (2001); Wu et al., J. Am. Chem. Soc., 122(32):7621-7632 (2000); O'Neill et al., J. Org. Chem., 67:5869-5875 (2002); Chaudhuri et al., J. Am. Chem. Soc., 117:10434-10442 (1995); and U.S. Pat. No. 6,218,108). Base analogs may also be a universal base.

As used herein, "universal base" refers to a heterocyclic moiety located at the 1' position of a nucleotide sugar moiety in a modified nucleotide, or the equivalent position in a nucleotide sugar moiety substitution, that, when present in a nucleic acid duplex, can be positioned opposite more than one type of base without altering the double helical structure (e.g., the structure of the phosphate backbone). Additionally, the universal base does not destroy the ability of the single stranded nucleic acid in which it resides to duplex to a target nucleic acid. The ability of a single stranded nucleic acid containing a universal base to duplex a target nucleic can be assayed by methods apparent to one in the art (e.g., UV absorbance, circular dichroism, gel shift, single stranded nuclease sensitivity, etc.). Additionally, conditions under which duplex formation is observed may be varied to determine duplex stability or formation, e.g., temperature, as melting temperature (Tm) correlates with the stability of nucleic acid duplexes. Compared to a reference single stranded nucleic acid that is exactly complementary to a target nucleic acid, the single stranded nucleic acid containing a universal base forms a duplex with the target nucleic acid that has a lower Tm than a duplex formed with the complementary nucleic acid. However, compared to a reference single stranded nucleic acid in which the universal base has been replaced with a base to generate a single mismatch, the single stranded nucleic acid containing the universal base forms a duplex with the target nucleic acid that has a higher Tm than a duplex formed with the nucleic acid having the mismatched base.

Some universal bases are capable of base pairing by forming hydrogen bonds between the universal base and all of the bases guanine (G), cytosine (C), adenine (A), thymine (T), and uracil (U) under base pair forming conditions. A universal base is not a base that forms a base pair with only one single complementary base. In a duplex, a universal base may form no hydrogen bonds, one hydrogen bond, or more than one hydrogen bond with each of G, C, A, T, and U opposite to it on the opposite strand of a duplex. Optionally, the universal base does not interact with the base opposite to it on the opposite strand of a duplex. In a duplex, base pairing between a universal base occurs without altering the double helical structure of the phosphate backbone. A universal base may also interact with bases in adjacent nucleotides on the same nucleic acid strand by stacking interactions. Such stacking interactions stabilize the duplex, especially in situations where the universal base does not form any hydrogen bonds with the base positioned opposite to it on the opposite strand of the duplex. Non-limiting examples of universal-binding nucleotides include inosine, 1-β-D-ribofuranosyl-5-nitroindole, and/or 1-β-D-ribofuranosyl-3-nitropyrrole (US Pat. Appl. Publ. No. 20070254362 to Quay et al.; Van Aerschot et al., An acyclic 5-nitroindazole nucleoside analogue as ambiguous nucleoside. Nucleic Acids Res. 1995 Nov. 11; 23(21):4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as an universal base analogue. Nucleic Acids Res. 1994 Oct. 11; 22(20):4039-43).

In certain embodiments, dsRNA-mediated inhibition of a target gene is assessed. In such embodiments, target gene RNA levels can be assessed by art-recognized methods (e.g., RT-PCR, Northern blot, expression array, etc.), optionally via comparison of target gene levels in the presence of a dsRNA formulation of the invention relative to the absence of such a dsRNA formulation. In certain embodiments, target gene levels in the presence of a dsRNA formulation are compared to those observed in the presence of vehicle alone, an unformulated dsRNA, in the presence of a dsRNA and/or dsRNA formulation directed against an unrelated target RNA, or in the absence of any treatment. It is also recognized that levels of target protein can be assessed as indicative of target gene RNA levels and/or the extent to which a dsRNA formulation inhibits target gene expression, thus art-recognized methods of assessing target gene protein levels (e.g., Western blot, immunoprecipitation, other antibody-based methods, etc.) can also be employed to examine the inhibitory effect of a dsRNA formulation of the invention. A dsRNA formulation of the invention is deemed to possess "target gene inhibitory activity" if a statistically significant reduction in target gene RNA or protein levels is seen when a dsRNA formulation of the invention is administered to a system (e.g., cell-free in vitro system), cell, tissue or organism, as compared to an appropriate control. The distribution of experimental values and the number of replicate assays performed will tend to dictate the parameters of what levels of reduction in target gene RNA or protein (either as a % or in absolute terms) is deemed statistically significant (as assessed by standard methods of determining statistical significance known in the art). However, in certain embodiments, "target gene inhibitory activity" is defined based upon a % or absolute level of reduction in the level of target gene in a system, cell, tissue or organism. For example, in certain embodiments, a dsRNA formulation of the invention is deemed to possess target gene inhibitory activity if at least a 5% reduction or at least a 10% reduction in target gene RNA is observed in the presence of a dsRNA formulation of the invention relative to target gene levels seen for a suitable control. (For example, in vivo target gene levels in a tissue and/or subject can, in certain embodiments, be deemed to be inhibited by a dsRNA formulation of the invention if e.g., a 5% or 10% reduction in target gene levels is observed relative to a control.) In certain other embodiments, a dsRNA formulation of the invention is deemed to possess target gene inhibitory activity if target gene RNA levels are observed to be reduced by at least 15% relative to an appropriate control, by at least 20% relative to an appropriate control, by at least 25% relative to an appropriate control, by at least 30% relative to an appropriate control, by at least 35% relative to an appropriate control, by at least 40% relative to an appropriate control, by at least 45% relative to an appropriate control, by at least 50% relative to an appropriate control, by at least 55% relative to an appropriate control, by at least 60% relative to an appropriate control, by at least 65% relative to an appropriate control, by at least 70% relative to an appropriate control, by at least 75% relative to an appropriate control, by at least 80% relative to an appropriate control, by at least 85% relative to an appropriate control, by at least 90% relative to an appropriate control, by at least 95% relative to an appropriate control, by at least 96% relative to an appropriate control, by at least 97% relative to an appropriate control, by at least 98% relative to an appropriate control or by at least 99% relative to an appropriate control. In some embodiments, complete inhibition of target gene is required for a dsRNA formulation to be deemed to possess target gene inhibitory activity. In certain models (e.g., cell culture), a dsRNA formulation is deemed to possess target gene inhibitory activity if at least a 50% reduction in target gene levels is observed relative to a suitable control. In certain other embodiments, a dsRNA formulation is deemed to possess target gene inhibitory activity if at least an 80% reduction in target gene levels is observed relative to a suitable control.

Target gene inhibitory activity can also be evaluated over time (duration) and over concentration ranges (potency), with assessment of what constitutes a dsRNA formulation possessing target gene inhibitory activity adjusted in accordance with concentrations administered and duration of time following administration. Thus, in certain embodiments, a dsRNA formulation of the invention is deemed to possess target gene inhibitory activity if at least a 50% reduction in target gene activity is observed at a duration of time of 2 hours, 5 hours, 10 hours, 1 day, 2 days, 3 days, 4 days, 5 days, 6 days, 7 days, 8 days, 9 days, 10 days or more after administration is observed/persists. In additional embodiments, a dsRNA formulation of the invention is deemed to be a potent target gene inhibitory agent if target gene inhibitory activity (e.g., in certain embodiments, at least 50% inhibition of target gene) is observed at a concentration of 1 nM or less, 500 pM or less, 200 pM or less, 100 pM or less, 50 pM or less, 20 pM or less, 10 pM or less, 5 pM or less, 2 pM or less or even 1 pM or less in the environment of a cell.

As used herein, the term "siRNA" refers to a double stranded nucleic acid in which each strand comprises RNA, RNA analog(s) or RNA and DNA. The siRNA comprises between 19 and 23 nucleotides or comprises 21 nucleotides. The siRNA typically has 2 bp overhangs on the 3' ends of each strand such that the duplex region in the siRNA comprises 17-21 nucleotides, or 19 nucleotides. Typically, the antisense strand of the siRNA is sufficiently complementary with the target sequence of the target gene and/or RNA.

In certain embodiments, a dsRNA cargo of the formulations of the instant invention can be an siRNA, e.g., having strand lengths comprising 17-23 nucleotides in length, or even 17-25 nucleotides in length (e.g., strand lengths of 17, 18, 19, 20, 21, 22, 23, 24 and/or 25 nucleotides in length. Such siRNA cargoes may possess overhangs on one or both ends of such dsRNA structures (e.g., one or two 3' overhangs), and can also possess modifications, such as those described herein and elsewhere in the art.

In other embodiments, a dsRNA of the dsRNA formulations of the instant invention possesses strand lengths of at least 25 nucleotides. Accordingly, a dsRNA contains one oligonucleotide sequence, a first sequence, that is at least 25 nucleotides in length. In certain embodiments, strand lengths of the dsRNA cargo of the invention are no longer than about 100 nucleotides in length, no longer than about 95 nucleotides in length, no longer than about 90 nucleotides in length, no longer than about 85 nucleotides in length, no longer than about 80 nucleotides in length, no longer than about 75 nucleotides in length, no longer than about 70 nucleotides in length, no longer than about 65 nucleotides in length or no longer than about 60 nucleotides in length. In further embodiments, a dsRNA cargo of the formulations of the invention contains a first sequence that is at least 25 nucleotides in length, and that is no longer than about 55 nucleotides, about 45 nucleotides, about 40 nucleotides, about 35 nucleotides, or about 30 nucleotides. The sequence of RNA can, for example, be between about 25 and 55, 25 and 50, 25 and 45, 25 and 40, 25 and 35, 25 and 34, 25 and 33, 25 and 32, 25 and 31, 25 and 30, 25 and 29, 25 and 28, 25 and 27, 25 and 26, 26 and 55, 26 and 50, 26 and 45, 26 and 40, 26 and 35, 26 and 34, 26 and 33, 26 and 32, 26 and 31, 26 and 30, 26 and 29, 26 and 28, and 26 and 27 nucleotides in length. This sequence can be about 27 or 28 nucleotides in length or 27 nucleotides in length. The second sequence of the dsRNA agent can be a sequence that anneals to the first sequence under biological conditions, such as within the cytoplasm of a eukaryotic cell. Generally, the second oligonucleotide sequence will have at least 19 complementary base pairs with the first oligonucleotide sequence, more typically the second oligonucleotide sequence will have about 21 or more complementary base pairs, or about 25 or more complementary base pairs with the first oligonucleotide sequence. In one embodiment, the second sequence is the same length as the first sequence, and the dsRNA agent is blunt ended. In another embodiment, the ends of the dsRNA agent have one or more overhangs.

In certain embodiments, the first and second oligonucleotide sequences of the dsRNA agent exist on separate oligonucleotide strands that can be and typically are chemically synthesized. In some embodiments, both strands are between 26 and 55 nucleotides in length. In other embodiments, both strands are between 25 and 45 or 26 and 45, between 25 and 35 or 26 and 35, or between 25 and 30 or 26 and 30 nucleotides in length. In one embodiment, both strands are 27 nucleotides in length, are completely complementary and have blunt ends. In certain embodiments of the instant invention, the first and second sequences of a dsRNA exist on separate RNA oligonucleotides (strands). In one embodiment, one or both oligonucleotide strands are capable of serving as a substrate for Dicer. In other embodiments, at least one modification is present that promotes Dicer to bind to the double-stranded RNA structure in an orientation that maximizes the double-stranded RNA structure's effectiveness in inhibiting gene expression. In certain embodiments of the instant invention, the dsRNA agent is comprised of two oligonucleotide strands of differing lengths, with the dsRNA possessing a blunt end at the 3' terminus of a first strand (sense strand) and a 3' overhang at the 3' terminus of a second strand (antisense strand). The dsRNA can also contain one or more deoxyribonucleic acid (DNA) base substitutions.

Suitable dsRNA compositions that contain two separate oligonucleotides can be chemically linked outside their annealing region (or through an annealed region) by chemical linking groups. Many suitable chemical linking groups are known in the art and can be used. Suitable groups will not block Dicer activity on the dsRNA and will not interfere with the directed destruction of the RNA transcribed from the target gene. Alternatively, the two separate oligonucleotides can be linked by a third oligonucleotide such that a hairpin structure is produced upon annealing of the two oligonucleotides making up the dsRNA composition. The hairpin structure will not block Dicer activity on the dsRNA and will not interfere with the directed destruction of the target RNA.

As used herein, a dsRNA, e.g., DsiRNA or siRNA, having a sequence "sufficiently complementary" to a target RNA or cDNA sequence (e.g., target gene mRNA) means that the dsRNA has a sequence sufficient to trigger the destruction of the target RNA (where a cDNA sequence is recited, the RNA sequence corresponding to the recited cDNA sequence) by the RNAi machinery (e.g., the RISC complex) or process. The dsRNA molecule can be designed such that every residue of the antisense strand is complementary to a residue in the target molecule. Alternatively, substitutions can be made within the molecule to increase stability and/or enhance processing activity of said molecule. Substitutions can be made within the strand or can be made to residues at the ends of the strand. In certain embodiments, substitutions and/or modifications are made at specific residues within a dsRNA agent. Such substitutions and/or modifications can include, e.g., deoxy-modifications at one or more residues of positions 1, 2 and 3 when numbering from the 3' terminal position of the sense strand of a dsRNA agent; and introduction of 2'-O-alkyl (e.g., 2'-O-methyl) modifications at the 3' terminal residue of the antisense strand of dsRNA agents, with such modifications also being performed at overhang positions of the 3' portion of the antisense strand and at alternating residues of the antisense strand of the dsRNA that are included within the region of a dsRNA agent that is processed to form an active siRNA agent. The preceding modifications are offered as exemplary, and are not intended to be limiting in any manner. Further consideration of the structure of dsRNA agents, including further description of the modifications and substitutions that can be performed upon the dsRNA agents of the instant invention, can be found elsewhere herein.

The phrase "duplex region" refers to the region in two complementary or substantially complementary oligonucleotides that form base pairs with one another, either by Watson-Crick base pairing or other manner that allows for a duplex between oligonucleotide strands that are complementary or substantially complementary. For example, an oligonucleotide strand having 21 nucleotide units can base pair with another oligonucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well know in the art. Alternatively, two strands can be synthesized and added together under biological conditions to determine if they anneal to one another.

Single-stranded nucleic acids that base pair over a number of bases are said to "hybridize." Hybridization is typically determined under physiological or biologically relevant conditions (e.g., intracellular: pH 7.2, 140 mM potassium ion; extracellular pH 7.4, 145 mM sodium ion). Hybridization conditions generally contain a monovalent cation and biologically acceptable buffer and may or may not contain a divalent cation, complex anions, e.g. gluconate from potassium gluconate, uncharged species such as sucrose, and inert polymers to reduce the activity of water in the sample, e.g. PEG. Such conditions include conditions under which base pairs can form.

Hybridization is measured by the temperature required to dissociate single stranded nucleic acids forming a duplex, i.e., (the melting temperature; Tm). Hybridization conditions are also conditions under which base pairs can form. Various conditions of stringency can be used to determine hybridization (see, e.g., Wahl, G. M. and S. L. Berger (1987) Methods Enzymol. 152:399; Kimmel, A. R. (1987) Methods Enzymol. 152:507). Stringent temperature conditions will ordinarily include temperatures of at least about 30° C., optionally of at least about 37° C., and in certain embodiments of at least about 42° C. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6 (log 10[Na+])+0.41 (% G+C)−(600/N), where N is the number of bases in the hybrid, and [Na+] is the concentration of sodium ions in the hybridization buffer ([Na+] for 1×SSC=0.165 M). For example, a hybridization determination buffer is shown in Table 1.

TABLE 1

| | final conc. | Vender | Cat# | Lot# | m.w./Stock | To make 50 mL solution |
|---|---|---|---|---|---|---|
| NaCl | 100 mM | Sigma | S-5150 | 41K8934 | 5M | 1 mL |
| KCl | 80 mM | Sigma | P-9541 | 70K0002 | 74.55 | 0.298 g |
| MgCl$_2$ | 8 mM | Sigma | M-1028 | 120K8933 | 1M | 0.4 mL |
| sucrose | 2% w/v | Fisher | BP220-212 | 907105 | 342.3 | 1 g |
| Tris-HCl | 16 mM | Fisher | BP1757-500 | 12419 | 1M | 0.8 mL |
| NaH$_2$PO$_4$ | 1 mM | Sigma | S-3193 | 52H-029515 | 120.0 | 0.006 g |
| EDTA | 0.02 mM | Sigma | E-7889 | 110K89271 | 0.5M | 2 μL |
| H$_2$O | | Sigma | W-4502 | 51K2359 adjust with HCl | | to 50 mL |
| pH = 7.0 at 20° C. | | | | | | |

Useful variations on hybridization conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Antisense to Molecular Cloning Techniques, 1987, Academic Press, New York); and Sambrook et al., Molecular Cloning: A Laboratory Manual, Cold Spring Harbor Laboratory Press, New York.

As used herein, "oligonucleotide strand" is a single stranded nucleic acid molecule. An oligonucleotide may comprise ribonucleotides, deoxyribonucleotides, modified nucleotides (e.g., nucleotides with 2' modifications, synthetic base analogs, etc.) or combinations thereof. Such modified oligonucleotides can be selected over native forms because of properties such as, for example, enhanced cellular uptake and increased stability in the presence of nucleases.

As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide. As used herein, the term "ribonucleotide" specifically excludes a deoxyribonucleotide, which is a nucleotide possessing a single proton group at the 2' ribose ring position. As used herein, the term "unmodified ribonucleotide" refers to a ribonucleotide containing only adenosine monophosphate, guanosine monophosphate, uridine monophosphate, or cytidine monophosphate, without further chemical modification.

As used herein, the term "deoxyribonucleotide" encompasses natural and synthetic, unmodified and modified deoxyribonucleotides. Modifications include changes to the sugar moiety, to the base moiety and/or to the linkages between deoxyribonucleotide in the oligonucleotide.

As used herein, "Dicer" refers to an endoribonuclease in the RNase III family that cleaves a dsRNA or dsRNA-containing molecule, e.g., double-stranded RNA (dsRNA) or pre-microRNA (miRNA), into double-stranded nucleic acid fragments about 19-25 nucleotides long, usually with a two-base overhang on the 3' end. With respect to the dsRNA formulations of the invention, the duplex formed by a dsRNA region of a formulation cargo of the invention is recognized by Dicer and is a Dicer substrate on at least one strand of the duplex. Dicer catalyzes the first step in the RNA interference pathway, which consequently results in the degradation of a target RNA. The protein sequence of human Dicer is provided at the NCBI database under accession number NP 085124, hereby incorporated by reference.

Dicer "cleavage" is determined as follows (e.g., see Collingwood et al., Oligonucleotides 18:187-200 (2008)). In a Dicer cleavage assay, RNA duplexes (100 pmol) are incubated in 20 μL of 20 mM Tris pH 8.0, 200 mM NaCl, 2.5 mM MgCl2 with or without 1 unit of recombinant human Dicer (Stratagene, La Jolla, Calif.) at 37° C. for 18-24 hours. Samples are desalted using a Performa SR 96-well plate (Edge Biosystems, Gaithersburg, Md.). Electrospray-ionization liquid chromatography mass spectroscopy (ESI-LCMS) of duplex RNAs pre- and post-treatment with Dicer is done using an Oligo HTCS system (Novatia, Princeton, N.J.; Hail et al., 2004), which consists of a ThermoFinnigan TSQ7000, Xcalibur data system, ProMass data processing software and Paradigm MS4 HPLC (Michrom BioResources, Auburn, Calif.). In this assay, Dicer cleavage occurs where at least 5%, 10%, 20%, 30%, 40%, 50%, 60%, 70%, 80%, 90%, 95%, or even 100% of the Dicer substrate dsRNA, (i.e., 25-30 bp, dsRNA, optionally 26-30 bp dsRNA) is cleaved to a shorter dsRNA (e.g., 19-23 bp dsRNA, optionally, 21-23 bp dsRNA).

As used herein, "Dicer cleavage site" refers to the sites at which Dicer cleaves a dsRNA (e.g., the dsRNA region of a DsiRNA agent of a formulation of the invention). Dicer contains two RNase III domains which typically cleave both the sense and antisense strands of a dsRNA. The average distance between the RNase III domains and the PAZ domain determines the length of the short double-stranded nucleic acid fragments it produces and this distance can vary (Macrae I, et al. (2006). "*Structural basis for double-stranded RNA processing by Dicer*". Science 311 (5758): 195-8). Dicer is projected to cleave certain double-stranded ribonucleic acids of the instant invention that possess an antisense strand having a 2 nucleotide 3' overhang at a site between the $21^{st}$ and $22^{nd}$ nucleotides removed from the 3' terminus of the antisense strand, and at a corresponding site between the $21^{st}$ and $22^{nd}$ nucleotides removed from the 5' terminus of the sense strand. The projected and/or prevalent Dicer cleavage site(s) for dsRNA molecules may be similarly identified via art-recognized methods, including those described in Macrae et al. While the Dicer cleavage events depicted in FIG. 1 generate 21 nucleotide siRNAs, it is noted that Dicer cleavage of a dsRNA (e.g., DsiRNA) can result in generation of Dicer-processed siRNA lengths of 19 to 23 nucleotides in length. Indeed, in certain embodiments, a double-stranded DNA region may be included within a dsRNA for purpose of directing prevalent Dicer excision of a typically non-preferred 19mer or 20mer siRNA, rather than a 21mer.

As used herein, "overhang" refers to unpaired nucleotides, in the context of a duplex having one or more free ends at the 5' terminus or 3' terminus of a dsRNA. In certain embodiments, the overhang is a 3' or 5' overhang on the antisense strand or sense strand. In some embodiments, the overhang is a 3' overhang having a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides.

As used herein, the term "RNA processing" refers to processing activities performed by components of the siRNA, miRNA or RNase H pathways (e.g., Drosha, Dicer, Argonaute2 or other RISC endoribonucleases, and RNaseH), which are described in greater detail below (see "RNA Processing" section below). The term is explicitly distinguished from the post-transcriptional processes of 5' capping of RNA and degradation of RNA via non-RISC- or non-RNase H-mediated processes. Such "degradation" of an RNA can take several forms, e.g. deadenylation (removal of a 3' poly(A) tail), and/or nuclease digestion of part or all of the body of the RNA by one or more of several endo- or exo-nucleases (e.g., RNase III, RNase P, RNase T1, RNase A (1, 2, 3, 4/5), oligonucleotidase, etc.).

By "homologous sequence" is meant, a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes, such as a cytokine and its corresponding receptors. A homologous sequence can be a nucleotide sequence that is shared by two or more non-coding polynucleotides, such as noncoding DNA or RNA, regulatory sequences, introns, and sites of transcriptional control or regulation. Homologous sequences can also include conserved sequence regions shared by more than one polynucleotide sequence. Homology does not need to be perfect homology (e.g., 100%), as partially homologous sequences are also contemplated by the instant invention (e.g., 99%, 98%, 97%, 96%, 95%, 94%, 93%, 92%, 91%, 90%, 89%, 88%, 87%, 86%, 85%, 84%, 83%, 82%, 81%, 80% etc.). Indeed, design and use of the dsRNA agents of the instant invention contemplates the possibility of using such dsRNA agents not only against target RNAs of target gene possessing perfect complementarity with the presently described dsRNA agents, but also against target RNAs possessing sequences that are, e.g., only 99%, 98%, 97%, 96%, 95%, 94%, 93%, 92%, 91%, 90%, 89%, 88%, 87%, 86%, 85%, 84%, 83%, 82%, 81%, 80% etc. complementary to said dsRNA agents. Similarly, it is contemplated that the presently described dsRNA agents of the instant invention might be readily altered by the skilled artisan to enhance the extent of complementarity between said dsRNA agents and a target RNA, e.g., of a specific allelic variant of target gene (e.g., an allele of enhanced therapeutic interest). Indeed, dsRNA agent sequences with insertions, deletions, and single point mutations relative to the target sequence can also be effective for inhibition. Alternatively, dsRNA agent sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions ×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the dsRNA antisense strand and the portion of the target gene RNA sequence is preferred. Alternatively, the dsRNA may be defined functionally as a nucleotide sequence (or oligonucleotide sequence) that is capable of hybridizing with a portion of the target gene RNA (e.g., 400 mM NaCl, 40 mM PIPES pH 6.4, 1 mM EDTA, 50°

C. or 70° C. hybridization for 12-16 hours; followed by washing). Additional hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, $Tm(° C.)=2(\text{\# of A+T bases})+4(\text{\# of G+C bases})$. For hybrids between 18 and 49 base pairs in length, $Tm(° C.)=81.5+16.6(\log 10[Na+])+0.41 (\% G+C)-(600/N)$, where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4. The length of the identical nucleotide sequences may be at least about 10, 12, 15, 17, 20, 22, 25, 27 or 30 bases.

By "conserved sequence region" is meant, a nucleotide sequence of one or more regions in a polynucleotide does not vary significantly between generations or from one biological system, subject, or organism to another biological system, subject, or organism. The polynucleotide can include both coding and non-coding DNA and RNA.

By "sense region" is meant a nucleotide sequence of a dsRNA molecule having complementarity to an antisense region of the dsRNA molecule. In addition, the sense region of a dsRNA molecule can comprise a nucleic acid sequence having homology with a target nucleic acid sequence.

By "antisense region" is meant a nucleotide sequence of a dsRNA molecule having complementarity to a target nucleic acid sequence. In addition, the antisense region of a dsRNA molecule comprises a nucleic acid sequence having complementarity to a sense region of the dsRNA molecule.

As used herein, "antisense strand" refers to a single stranded nucleic acid molecule which has a sequence complementary to that of a target RNA. When the antisense strand contains modified nucleotides with base analogs, it is not necessarily complementary over its entire length, but must at least hybridize with a target RNA.

As used herein, "sense strand" refers to a single stranded nucleic acid molecule which has a sequence complementary to that of an antisense strand. When the antisense strand contains modified nucleotides with base analogs, the sense strand need not be complementary over the entire length of the antisense strand, but must at least duplex with the antisense strand.

As used herein, "guide strand" refers to a single stranded nucleic acid molecule of a dsRNA or dsRNA-containing molecule, which has a sequence sufficiently complementary to that of a target RNA to result in RNA interference. After cleavage of the dsRNA or dsRNA-containing molecule by Dicer, a fragment of the guide strand remains associated with RISC, binds a target RNA as a component of the RISC complex, and promotes cleavage of a target RNA by RISC. As used herein, the guide strand does not necessarily refer to a continuous single stranded nucleic acid and may comprise a discontinuity, optionally at a site that is cleaved by Dicer. A guide strand is an antisense strand.

As used herein, "passenger strand" refers to an oligonucleotide strand of a dsRNA or dsRNA-containing molecule, which has a sequence that is complementary to that of the guide strand. As used herein, the passenger strand does not necessarily refer to a continuous single stranded nucleic acid and may comprise a discontinuity, optionally at a site that is cleaved by Dicer. A passenger strand is a sense strand.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Perfectly complementary" means that all the contiguous residues of a nucleic acid sequence will hydrogen bond with the same number of contiguous residues in a second nucleic acid sequence. In one embodiment, a dsRNA molecule of a formulation of the invention comprises about 19 to about 30 (e.g., about 19, 20, 21, 22, 23, 24, 25, 26, 27, 28, 29, or 30 or more) nucleotides that are complementary to one or more target nucleic acid molecules or a portion thereof.

In one embodiment of the present invention, each sequence of a dsRNA molecule of a formulation of the invention is independently about 25 to about 55 nucleotides in length, in specific embodiments about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 nucleotides in length. In another embodiment, the dsRNA duplexes of a formulation of the invention independently comprise about 25 to about 40 base pairs (e.g., about 25, 26, 27, 28, 29, 30, 31, 32, 33, 34, 35, 36, 37, 38, 39, or 40), or in certain embodiments, about 25 to about 30 base pairs (e.g., about 25, 26, 27, 28, 29 or 30). In another embodiment, one or more strands of the dsRNA molecule of a formulation of the invention independently comprises about 19 to about 35 nucleotides (e.g., about 19, 20, 21, 22, 23, 24, 25, 26, 27, 28, 29, 30, 31, 32, 33, 34 or 35) that are complementary to a target (target gene) nucleic acid molecule. In certain embodiments, a dsRNA molecule of a formulation of the invention possesses a length of duplexed nucleotides between 25 and 55 nucleotides in length (e.g., 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides in length; optionally, all such nucleotides base pair with cognate nucleotides of the opposite strand). (Exemplary dsRNA molecules of a formulation of the invention are shown below.)

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

Within certain aspects, the term "cell" refers specifically to mammalian cells, such as human cells, that contain one or more isolated dsRNA molecules of the present disclosure. In particular aspects, a cell processes dsRNAs or dsRNA-containing molecules resulting in RNA interference of target nucleic acids, and contains proteins and protein complexes required for RNAi, e.g., Dicer and RISC.

The dsRNA molecules of certain formulations of the invention are added directly, or can be complexed with cationic lipids, packaged within liposomes, or otherwise delivered to target cells or tissues. Such nucleic acid formulations can be locally administered to relevant tissues ex vivo, or in vivo through direct dermal application, transdermal application, or injection, with or without their incorporation in biopolymers. In particular embodiments, the nucleic acid molecules of certain formulations of the invention are structures as shown below. Examples of such nucleic acid formulations consist essentially of structures defined in these exemplary structures.

In another aspect, the invention provides one or more formulations containing one or more dsRNAs as described herein. The one or more formulations and/or dsRNA molecules can independently be targeted to the same or different sites.

By "RNA" is meant a molecule comprising at least one ribonucleotide residue. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the dsRNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The pharmaceutically acceptable carrier of the disclosed dsRNA compositions may be micellar structures, such as a liposomes, capsids, capsoids, polymeric nanocapsules, or polymeric microcapsules.

Polymeric nanocapsules or microcapsules facilitate transport and release of the encapsulated or bound cargo (e.g., dsRNA) into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Compounds according to the invention are the compounds of the formula (I) and the salts, solvates and solvates of the salts thereof, as well as the compounds encompassed by the formula (I) and mentioned below as exemplary embodiment(s), and the salts, solvates and solvates of the salts thereof, insofar as the compounds encompassed by formula (I) and mentioned below are not already salts, solvates and solvates of the salts.

The compounds of the invention may, depending on their structure, exist in stereoisomeric forms (enantiomers, diastereomers). The invention therefore encompasses the enantiomers or diastereomers and respective mixtures thereof. The stereoisomerically pure constituents can be isolated in a known manner from such mixtures of enantiomers and/or diastereomers.

Where the compounds of the invention can occur in tautomeric forms, the present invention encompasses all tautomeric forms.

Salts preferred for the purposes of the present invention are physiologically acceptable salts of the compounds of the invention. However, salts which are themselves unsuitable for pharmaceutical applications but can be used for example for isolating or purifying the compounds of the invention are also encompassed.

Physiologically acceptable salts of the compounds of the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Solvates refer for the purposes of the invention to those forms of the compounds of the invention which form a complex in the solid or liquid state through coordination with solvent molecules. Hydrates are a specific form of solvates in which the coordination takes place with water.

The term "sterol" includes natural and synthetic sterols including cholesterol and other animal-derived sterols, phytosterols, phytosterol esters, phytostanols, and phytostanol esters.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

For the purposes of the present invention, the substituents have, unless specified otherwise, the following meaning:

Alkyl per se and "alk" and "alkyl" in alkoxy, alkylamino, alkylcarbonyl, alkoxycarbonyl, alkylaminocarbonyl, alkylcarbonylamino, alkylsulphonyl, alkylsulphonylamino and alkylaminosulphonyl stand for a linear or branched alkyl radical having 1 to 30 carbon atoms; in certain embodiments, an alkyl can have 1 to 20 carbon atoms, 1 to 10 carbon atoms, 1 to 6 carbon atoms, or 1 to 4 carbon atoms, by way of example. In certain embodiments, an alkyl is, e.g., and preferably for methyl, ethyl, n-propyl, isopropyl, n-butyl and tert-butyl. In certain embodiments, the term "alkyl" can also refers to long alkyl "tails" of the lipid compounds of the invention, e.g., those possessing as many as 14, 16, 18, 20 or more carbon atoms, including saturated and unsaturated forms of such alkyl "tails".

Alkoxy stands by way of example and preferably for methoxy, ethoxy, n-propoxy, isopropoxy, n-butoxy and tert-butoxy.

Alkylamino stands for an alkylamino radical having one to four alkyl substitutions (chosen independently of one another), by way of example and preferably for methylamino, ethylamino, n-propylamino, isopropylamino, tert-butylamino, N,N-dimethylamino, N,N-diethylamino, N-ethyl-N-methylamino, N-methyl-N-n-propylamino, N-isopropyl-N-n-propylamino and N-tert-butyl-N-methylamino. $C_1$-$C_4$-alkylamino stands for example for a monoalkylamino radical having 1 to 4 carbon atoms or for a dialkylamino radical having 1 to 4 carbon atoms in each alkyl substituent in each case.

Monoalkylamino stands for an alkylamino radical having a linear or branched alkyl substituent, by way of example and preferably for methylamino, ethylamino, n-propylamino, isopropylamino and tert-butylamino.

Monocycloalkylamino stands for a cycloalkylamino radical having a cycloalkyl substituent, where the other substituent at the amino radical is hydrogen, by way of example and preferably for cyclopropylamino and cyclobutylamino.

Alkylcarbonyl stands by way of example and preferably for methylcarbonyl, ethylcarbonyl, n-propylcarbonyl, isopropylcarbonyl, n-butylcarbonyl and tert-butylcarbonyl.

Alkoxycarbonyl stands by way of example and preferably for methoxycarbonyl, ethoxycarbonyl, n-propoxycarbonyl, isopropoxycarbonyl, n-butoxycarbonyl and tert-butoxycarbonyl.

Alkylaminocarbonyl stands for an alkylaminocarbonyl radical having one or two alkyl substituents (chosen independently of one another), by way of example and preferably for methylaminocarbonyl, ethylaminocarbonyl, n-propylaminocarbonyl, isopropylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl and N-tert-butyl-N-methylaminocarbonyl. $C_1$-$C_4$-Alkylaminocarbonyl stands for example for a monoalkylaminocarbonyl radical having 1 to 4 carbon atoms or for a dialkylaminocarbonyl radical having 1 to 4 carbon atoms in each alkyl substituent in each case.

Alkylcarbonylamino stands by way of example and preferably for methylcarbonylamino, ethyl carbonyl amino, n-propylcarbonylamino, isopropylcarbonylamino, n-butylcarbonylamino and tert-butylcarbonylamino.

Alkylsulphonyl stands by way of example and preferably for methylsulphonyl, ethylsulphonyl, n-propylsulphonyl, isopropylsulphonyl, n-butylsulphonyl and tert-butylsulphonyl.

Alkylaminosulphonyl stands for an alkylaminosulphonyl radical having one or two alkyl substituents (chosen independently of one another), by way of example and preferably for methylaminosulphonyl, ethylaminosulphonyl, n-propylaminosulphonyl, isopropylaminosulphonyl, tert-butylaminosulphonyl, N,N-dimethylaminosulphonyl, N,N-diethylaminosulphonyl, N-ethyl-N-methylaminosulphonyl, N-methyl-N-n-propylaminosulphonyl, N-isopropyl-N-n-propylaminosulphonyl and N-tert-butyl-N-methylaminosulphonyl. $C_1$-$C_4$-Alkylaminosulphonyl stands for example for a monoalkylaminosulphonyl radical having 1 to 4 carbon atoms or for a dialkylaminosulphonyl radical having 1 to 4 carbon atoms in each alkyl substituent in each case.

Alkylsulphonylamino stands by way of example and preferably for methylsulphonylamino, ethylsulphonylamino, n-propylsulphonylamino, isopropylsulphonylamino, n-butylsulphonylamino and tert-butylsulphonylamino.

Cycloalkyl stands for a monocyclic cycloalkyl group usually having 3 to 6 carbon atoms, and mention may be made by way of example and preferably of cyclopropyl, cyclobutyl, cyclopentyl and cyclohexyl for cycloalkyl.

Heterocyclyl stands for a monocyclic, heterocyclic radical having 5 or 6 ring atoms and up to 3, preferably up to 2 heteroatoms and/or heterogroups from the series N, O, S, SO, $SO_2$, where a nitrogen atom may also form an N-oxide. The heterocyclyl radicals may be saturated or partly unsaturated. 5- or 6-membered, monocyclic saturated heterocyclyl radicals having up to 2 heteroatoms from the series O, N and S are preferred, by way of example and preferably for pyrrolidin-2-yl, pyrrolidin-3-yl, pyrrolinyl, tetrahydrofuranyl, tetrahydrothienyl, pyranyl, piperidin-1-yl, piperidin-2-yl, piperidin-3-yl, piperidin-4-yl, thiopyranyl, morpholin-1-yl, morpholin-2-yl, morpholin-3-yl, piperazin-1-yl, piperazin-2-yl.

Heteroaryl stands for an aromatic, mono- or bicyclic radical usually having 5 to 10, preferably 5 or 6 ring atoms and up to 5, preferably up to 4 heteroatoms from the series S, O and N, where a nitrogen atom may also form an N-oxide, by way of example and preferably for thienyl, furyl, pyrrolyl, thiazolyl, oxazolyl, oxadiazolyl, pyrazolyl, imidazolyl, triazolyl, pyridyl, pyrimidyl, pyridazinyl, pyrazinyl, indolyl, indazolyl, benzofuranyl, benzothiophenyl, quinolinyl, isoquinolinyl, benzoxazolyl, benzimidazolyl.

Halogen stands for fluorine, chlorine, bromine and iodine, preferably for fluorine and chlorine.

Various methodologies of the instant invention include a step that involves comparing a value, level, feature, characteristic, property, etc. to a "suitable control", referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent formulation (e.g., DsiRNA formulation) of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

"Treatment", or "treating" as used herein, is defined as the application or administration of a therapeutic agent (e.g., a dsRNA formulation, dsRNA agent or a vector or transgene encoding same) to a patient, or application or administration of a therapeutic agent to an isolated tissue or cell line from a patient, who has a disorder with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. The term "patient" includes human and other mammalian subjects that receive either prophylactic or therapeutic treatment.

The term "target gene" refers to nucleic acid sequences (e.g., genomic DNAs or mRNAs) encoding a target protein, peptide, or polypeptide, or that encode for or are regulatory nucleic acids (e.g., a "target gene" for purpose of the instant invention can also be a miRNA or miRNA-encoding gene sequence). In certain embodiments, the term "target gene" is also meant to include isoforms, mutants, polymorphisms and splice variants of target genes. In certain embodiments of the instant invention, a dsRNA of a formulation of the invention targets a sequence within the 5'-UTR, coding sequence and/or 3'-UTR of a target gene mRNA.

Immune Responses to Formulations Comprising Immunogenic or Immunostimulatory Cargoes, Lipids or Delivery Moieties Lipid formulations of the invention that comprise an immunogenic or immunostimulatory cargo, lipid and/or delivery moiety can trigger an immune response in a mammalian subject to which such a formulation is administered. Specifically, in addition to the immunogenic effects of certain cargoes (e.g., dsRNAs) and delivery moieties, cationic lipids of a lipid formulation can activate TLR4 directly, resulting in a TLR4-mediated immune response in a subject to which the lipid formulation is administered. Cationic lipids can also help activate TLR3-, TLR7-, TLR8-, TLR9- and other TLR-mediated and intracellular sensor immune responses (Hagele et al. *Nephrology Dialysis Transplantation* 24: 3312-3318) in a subject when associated with nucleic acid cargoes (e.g., dsRNAs).

TLR4 is a toll-like receptor. It detects lipopolysaccharide (LPS; e.g., of Gram-negative bacteria) and is thus important in the activation of the innate immune system (including, e.g., activation of interferon type I). TLR4 has also been designated as CD284 (cluster of differentiation 284).

The protein encoded by the TLR4 gene is a member of the Toll-like receptor (TLR) family, which plays a fundamental role in pathogen recognition and activation of innate immunity. TLRs are highly conserved from *Drosophila* to humans and share structural and functional similarities. They recognize pathogen-associated molecular patterns (PAMPs) that are expressed on infectious agents, and mediate the production of cytokines necessary for the development of effective immunity. The various TLRs exhibit different patterns of expression. This receptor is most abundantly expressed in placenta, and in myelomonocytic subpopulation of the leukocytes. It has been implicated in signal transduction events induced by lipopolysaccharide (LPS) found in most gram-negative bacteria. Mutations in this gene have been associated with differences in LPS responsiveness. Several transcript variants of this gene have also been identified, but the protein coding potential of most of them is uncertain (www.ncbi.nlm.nih.gov/sites/entrez?Db=gene&Cmd=ShowDetailView &TermToSearch=7099).

Lipopolysaccharide (LPS) activates monocytes and macrophages to produce cytokines such as TNF-α and IL-1β that act as endogenous inflammatory mediators (Beutler, B, et al. J Leukoc Biol 74, 479-85 (2003)).

Cytokines that regulate innate immunity are produced primarily by mononuclear phagocytes such as macrophages and dendritic cells. "Dendritic cells" are derived from monocytes and are located throughout the epithelium of the skin, the respiratory tract, and the gastrointestinal tract. Without being bound by theory, the primary function of dendritic cells is to capture and present protein antigens to naive T-lymphocytes. Dendritic cells can also be produced by T-lymphocytes, NK cells, endothelial cells, and mucosal epithelial cells. They are produced primarily in response to pathogen-associated molecular patterns (PAMPs) such as lipopolysaccharide (LPS), peptidoglycan monomers, teichoic acids, unmethylated cytosine-guanine dinucleotide or CpG sequences in bacterial and viral genomes, and double-stranded RNA (of exogenous, e.g., viral, origin). Cytokines produced in response to pattern recognition receptors (PRRs) on cell surfaces, such as the inflammatory cytokines IL-1, IL-6, IL-8, and TNF-alpha, mainly act on leukocytes and the endothelial cells that form blood vessels in order to promote and control early inflammatory responses.

Toll-like receptors bind and become activated by different ligands, which, in turn are located on different types of organisms or structures. They also have different adapters to respond to activation and are located sometimes at the cell surface and sometimes to internal cell compartments. Furthermore, they are expressed by different types of leucocytes or other cell types:

| Receptor | Ligand(s)[1] | Ligand location[1] | Adapter(s) | Location | Cell types[1] |
|---|---|---|---|---|---|
| TLR 1 | multiple triacyl lipopeptides | Bacteria | MyD88/MAL | cell surface | monocytes/ macrophages a subset of dendritic cells B lymphocytes |
| TLR 2 | multiple glycolipids | Bacteria | MyD88/MAL | cell surface | monocytes/ macrophages |
| | multiple lipopeptides | Bacteria | | | Myeloid dendritic cells[2] |
| | multiple lipoproteins | Bacteria | | | Mast cells |
| | lipoteichoic | Bacteria | | | |

-continued

| Receptor | Ligand(s)[1] | Ligand location[1] | Adapter(s) | Location | Cell types[1] |
|---|---|---|---|---|---|
| | acid<br>HSP70<br>zymosan<br>(Beta-glucan)<br>Numerous others | Host cells<br>Fungi | | | |
| TLR 3 | double-stranded RNA, poly I: C | viruses | TRIF | cell compartment | Dendritic cells<br>B lymphocytes |
| TLR 4 | lipopoly-saccharide<br>several heat shock proteins<br>fibrinogen<br>heparan sulfate fragments<br>hyaluronic acid fragments<br>Numerous others | Gram-negative bacteria<br>Bacteria and host cells<br>host cells<br>host cells<br>host cells | MyD88/MAL/<br>TRIF/TRAM | cell surface | monocytes/macrophages<br>Myeloid dendritic cells[2]<br>Mast cells<br>Intestinal epithelium |
| TLR 5 | flagellin | Bacteria | MyD88 | cell surface | monocyte/macrophages<br>a subset of dendritic cells<br>Intestinal epithelium |
| TLR 6 | multiple diacyl lipopeptides | Mycoplasma | MyD88/MAL | cell surface | monocytes/macrophages<br>Mast cells<br>B lymphocytes |
| TLR 7 | imidazoquinoline<br>loxoribine (a guanosine analogue)<br>bropirimine<br>single-stranded RNA | small synthetic compounds | MyD88 | cell compartment | monocytes/macrophages<br>Plasmacytoid dendritic cells[2]<br>B lymphocytes |
| TLR 8 | small synthetic compounds;<br>single-stranded RNA | | MyD88 | cell compartment | monocytes/macrophages<br>a subset of dendritic cells<br>Mast cells |
| TLR 9 | unmethylated CpG Oligodeoxy-nucleotide DNA | Bacteria | MyD88 | cell compartment | monocytes/macrophages<br>Plasmacytoid dendritic cells[2]<br>B lymphocytes |
| TLR 10 | unknown | unknown | unknown | cell surface | monocytes/macrophages<br>B lymphocytes |
| TLR 11 | Profilin | *Toxoplasma gondii* | MyD88 | cell surface | monocytes/macrophages<br>liver cells<br>kidney<br>bladder epithelium |

[1]Waltenbaugh C, Doan T, Melvold R, Viselli S (2008). *Immunology*. Lippincott's Illustrated reviews. Philadelphia: Wolters Kluwer Health/Lippincott Williams & Wilkins. pp. 17.
[2]Sallusto F, Lanzavecchia A (2002). "The instructive role of dendritic cells on T-cell responses". *Arthritis Res*. 4 Suppl 3: S127-32.

Cytokines produced in response to PRRs that recognize nucleic acids, such as type I interferons, primarily block viral replication within infected host cells.

Type I Interferons

Interferons modulate the activity of virtually every component of the immune system. Type I interferons include 13 subtypes of interferon-alpha, interferon-beta, interferon omega, interferon-kappa, and interferon tau. (There is only one type II interferon, interferon-gamma, which is involved in the inflammatory response.)

A strong stimulus for type I interferons is the binding of viral/exogenous DNA or RNA (e.g., dsRNA) to toll-like receptors TLR-3, TLR-7, TLR-8 and TLR-9 in endosomal membranes.

a. TLR-3-binds double-stranded viral/exogenous RNA;
b. TLR-7 and TLR-8-bind single-stranded viral/exogenous RNA, such as in HIV, rich in guanine/uracil nucleotide pairs; (Handbook of Experimental Pharmacology, Toll-Like Receptors (TLRs) and Innate Immunity 10.1007/978-3-540-72167-3 4, S. Bauer and G. Hartmann).
c. TLR-9-binds unmethylated cytosine-guanine dinucleotide sequences (CpG DNA) found in bacterial and viral genomes but uncommom or masked in human DNA and RNA.

Signaling pattern recognition receptors located in the cytoplasm of cells such as RIG-1 (RIG-I) and MDA-5 also signal synthesis and secretion of type-I interferons. Type I interferons, produced by virtually any virus-infected cell, provides an early innate immune response against viruses. Interferons induce uninfected cells to produce enzymes capable of degrading mRNA. These enzymes remain inactive until the uninfected cell becomes infected with a virus (or is administered a dsRNA, thereby mimicking viral infection). At this point, the enzymes are activated and begin to degrade both viral/exogenous and cellular mRNA. This not only blocks viral protein synthesis, it also eventually kills the infected cell. In addition, type I interferons also cause infected cells to produce enzymes that interfere with transcription of viral RNA or DNA. They also promote body defenses by enhancing the activities of CTLs, macrophages, dendritic cells, NK cells, and antibody-producing cells.

Type I interferons also induce MHC-I antigen expression needed for recognition of antigens by cytotoxic T-lymphocytes; augment macrophage, NK cell, cytotoxic T-lymphocytes, and B-lymphocyte activity; and induce fever. Interferon-alpha is produced by T-lymphocytes, B-lymphocytes, NK cells, monocytes/macrophages; interferon-beta by virus-infected cells, fibroblasts, macrophages, epithelial cells, and endothelial cells.

"Macrophages" are cells derived from monocytes, which are located throughout the body. Without wishing to be bound by theory, macrophages are important phagocytes, produce proinflammatory cytokines, and can capture and present protein antigens to naïve T-lymphocytes.

Immune Response Reducing Lipids

The pulmonary surfactant phospholipids palmitoyl-oleoyl-phosphatidylglycerol (POPG) and dipalmitoylphosphatidylcholine (DPPC) were recently identified as capable of disrupting TLR4 activation (Numata et al. PNAS USA 107: 320-325; Abate et al., J Lipid Res 51: 334-344). In the case of POPG, such disruption appears to occur via interaction with CD14 and MD-2 (Numata et al. PNAS USA 107: 320-325).

The instant invention is based, at least in part, upon exploiting the immune response silencing (e.g., TLR4 inhibiting) attributes of specific lipids, e.g., anionic lipids such as POPG, DPPC and the lipids of FIGS. 1-14, to allow for generation of formulations that exhibit reduced levels of immune response induction following administration of such formulations to a subject, as compared to an appropriate control formulation that lacks such an immune response reducing lipid. Indeed, one advantage of a formulation of the instant invention is that the formulation, by virtue of including the immune response reducing lipid, can reduce or even prevent an immune response that would otherwise occur in a subject in reaction to an immunogenic or immunostimulatory cargo, second lipid (e.g., one or more cationic lipids of the formulation) and/or associated delivery moiety of the formulation.

Exemplary immune response reducing lipids of the instant invention include palmitoyl-oleoyl-phosphatidylglycerol (POPG), dipalmitoylphosphatidylcholine (DPPC), the lipids of FIGS. 1-14, isolated chiral forms of DOTAP (R-DOTAP or S-DOTAP), isolated chiral forms of DSPC (R-DSPC or S-DSPC), and derivatives thereof. In addition, the instant invention contemplates that anionic lipids as a class may possess immune response silencing properties similar to those of the exemplary immune response reducing anionic lipids recited above. The immune response reducing lipid typically comprises from about 10 mol % to about 85 mol %, from about 20 mol % to about 80 mol %, or about 30 mol % of the total lipid present in the formulation. Optionally, the immune response reducing lipid may comprise from about 5 mol % to about 100 mol % or about 15 mol % to about 75 mol % or about 20 mol % to about 50 mol % or about 40 mol % of the total lipid present in the formulation. In specific embodiments, the immune response reducing lipid may comprise about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, about 21 mol %, about 22 mol %, about 23 mol %, about 24 mol %, about 25 mol %, about 30 mol %, about 35 mol %, about 40 mol %, about 45 mol %, about 50 mol %, about 55 mol %, about 60 mol %, about 65 mol %, about 70 mol %, about 75 mol %, about 80 mol %, about 85 mol %, or about 90 mol % of the total lipid present in the formulation.

In certain embodiments, the immune response reducing lipids of the instant invention include a compound of formula (I):

$$R_1\text{—}R_2\text{—}R_3 \qquad (I)$$

where $R_1$ is a lipophilic moiety including a single sterol, a dimeric sterol, a multimeric sterol, a single alkyl chain from 5 to 24 carbon atoms, a multiple alkyl chain from 5 to 24 carbon atoms each, a single symmetric branched alkyl moiety from 10 to 50 carbon atoms each, a multiple symmetric branched alkyl moiety from 10 to 50 carbon atoms each, a single asymmetric branched alkyl chain ranging from 10 to 50 carbons each, a multiple asymmetric branched alkyl chain ranging from 10 to 50 carbons each, a single alkenyl chain containing one or more unsaturations from 5 to 24 carbon atoms, a multiple alkyl chain containing one or more unsaturations from 5 to 24 carbon atoms each, a single symmetric branched alkyl moiety containing one or more unsaturations from 10 to 50 carbon atoms each, a multiple symmetric branched alkyl moiety containing one or more unsaturations from 10 to 50 carbon atoms each, a single asymmetric branched alkyl chain containing one or more unsaturations ranging from 10 to 50 carbons each, a multiple asymmetric branched alkyl chain containing one or more unsaturations ranging from 10 to 50 carbons each, a mixed alkyl chain from 5 to 24 carbon atoms, or an alkenyl chain containing one or more unsaturations from 5 to 24 carbon atoms; $R_2$ is a negatively charged or neutral moiety linking $R_1$ and $R_3$ including a negatively charged phosphate ester, a neutral phosphonate, a carbamate, an amide, one or more neutral or negatively charged amino acids, an ether, a ketone, an ester, an alkyl chain from one to 10 carbons, or a disulfide linked moiety; and $R_3$ is a negatively charged or neutral moiety having two or more hydroxyls, carbonates, ethers, or carboxylates; or two or more alkyl esters from 1 to 6 carbons; or two or more alkyl esters from 2 to 6 carbons. Exemplary $R_3$ groups of the immune response reducing lipids of the invention include small polyhydroxylated moieties, e.g., citrate, isocitrate, aconitate, hydroxycitrate, methylisocitrate, homocitrate, 2-(2,2-dihydroxyethyl)-2-hydroxy-butanedioic acid, 3-ethyl-3-hydroxy-pentanedioic acid, 3-(dihydroxymethyl)-3-hydroxy-pentanedioic acid, 2-hydroxy-2-(ethoxycarbonylmethyl)butanedioic acid, 2-hydroxy-2-(methoxycarbonylmethyl)butanedioic acid, malate, fumarate, tartarate, ethyl citrate, butyl citrate, methyl citrate, 2,3,4-trihydroxy-pentanedioic acid, arabic acid, 2,5-diketogluconate, 5-ketogluconate, oxalomalic acid, fructuronic acid, L,S-citramalic acid, 3-ethylmalate, 3-propylmalate, a moiety shown in FIG. 8, a methoxy-, ethoxy- or propoxy-derivatives of a moiety shown in FIG. 8, or equivalents thereof.

Figure 9:
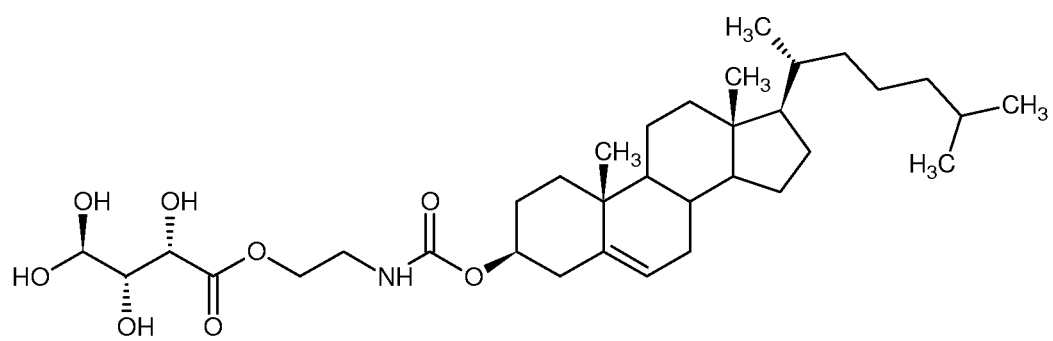

In one embodiment, the compound is (2S,3S)-2-(((3S,10R, 13R,17R)-10,13-dimethyl-17-((R)-6-methylheptan-2-yl)-2, 3,4,7,8,9,10,11,12,13,14,15,16,17-tetradecahydro-1H-cyclopenta[a]phenanthren-3-yloxy)carbonylamino)ethyl 2,3,4, 4-tetrahydroxybutanoate, DPC-1 shown in FIG. 9, or

Figure 10:
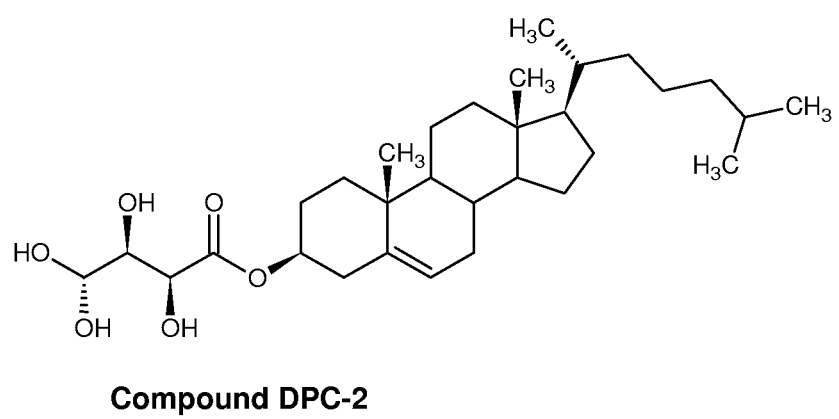
Figure 11:
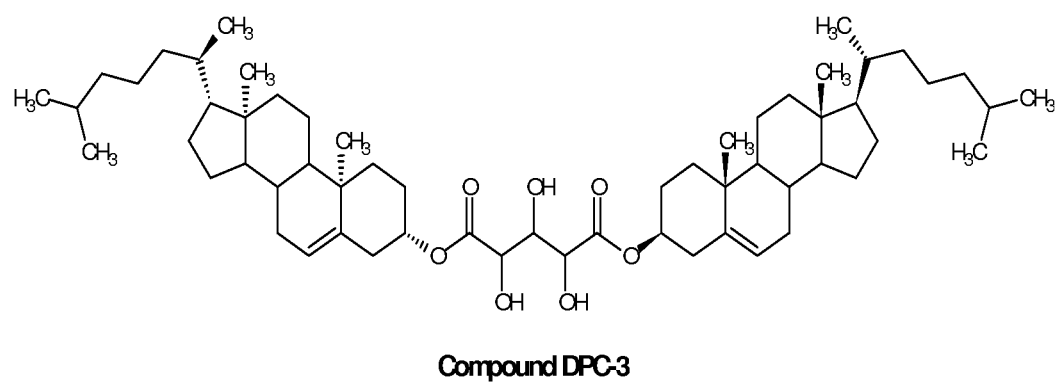

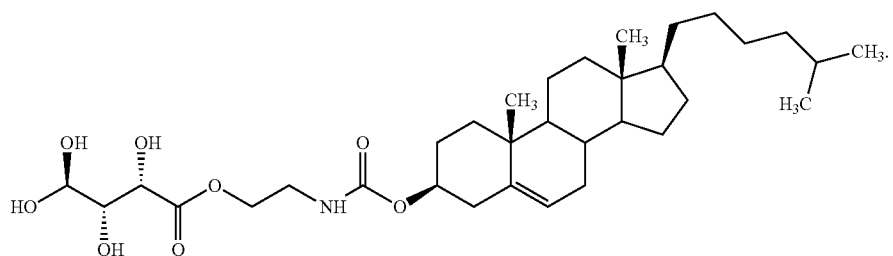
In one embodiment, the compound is (2S,3S)-((3 S,10R, 13R,17R)-10,13-dimethyl-17-((R)-6-methylheptan-2-yl)-2, 3,4,7,8,9,10,11,12,13,14,15,16,17-tetradecahydro-1H-cyclopenta[a]phenanthren-3-yl) 2,3,4,4-tetrahydroxybutanoate, DPC-2 shown in FIG. 10, or
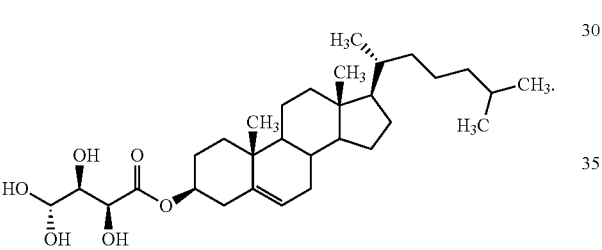
In one embodiment, the compound is bis((3S,10R,13R, 17R)-10,13-dimethyl-17-((R)-6-methylheptan-2-yl)-2,3,4, 7,8,9,10,11,12,13,14,15,16,17-tetradecahydro-1H-cyclopenta[a]phenanthren-3-yl) 2,3,4-trihydroxypentanedioate, DPC-3 shown in FIG. 11, or
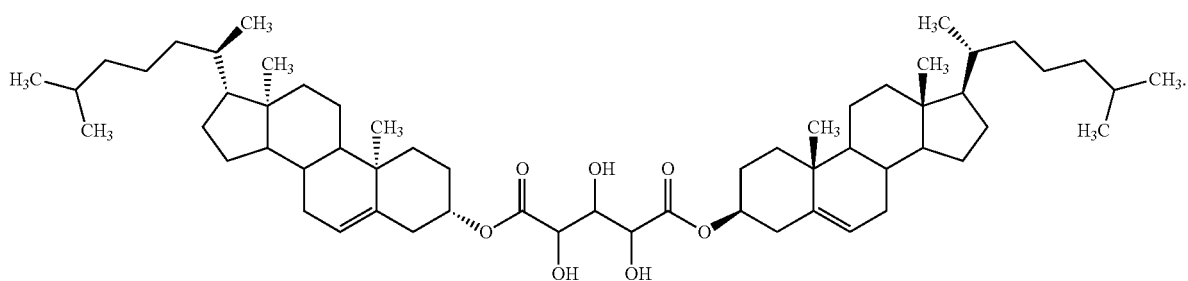 [SMILES: CC(C)CCC[C@@H](C)[C@H]1CCC2C3CC=C4C[C@@H](OC(=O)C(O)C(O)C(O)C(=O)O[C@H]5CC[C@@]6(C)C(=CCC7C6CC[C@@]6(C)C7CC[C@@H]6[C@H](C)CCCC(C)C)C5)CC[C@]4(C)C3CC[C@@]21C]

Figure 12:
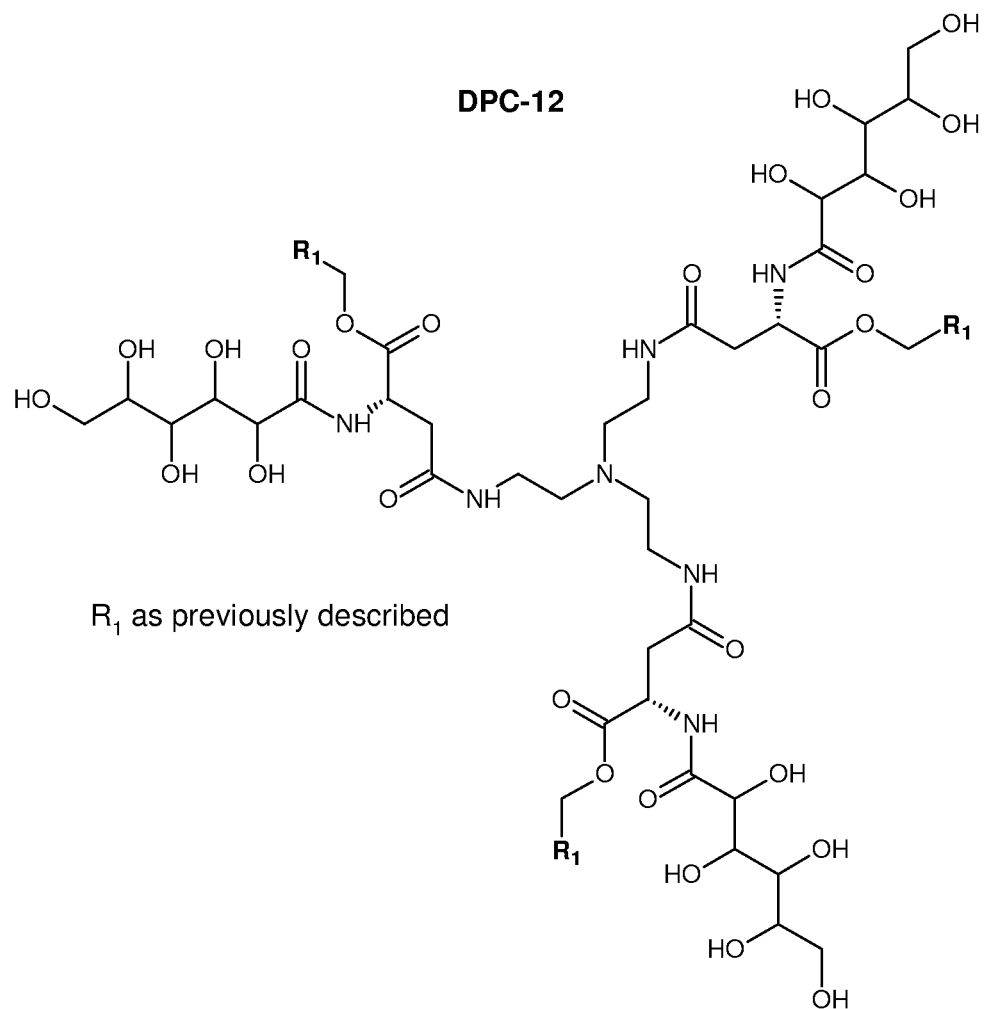
Figure 13:
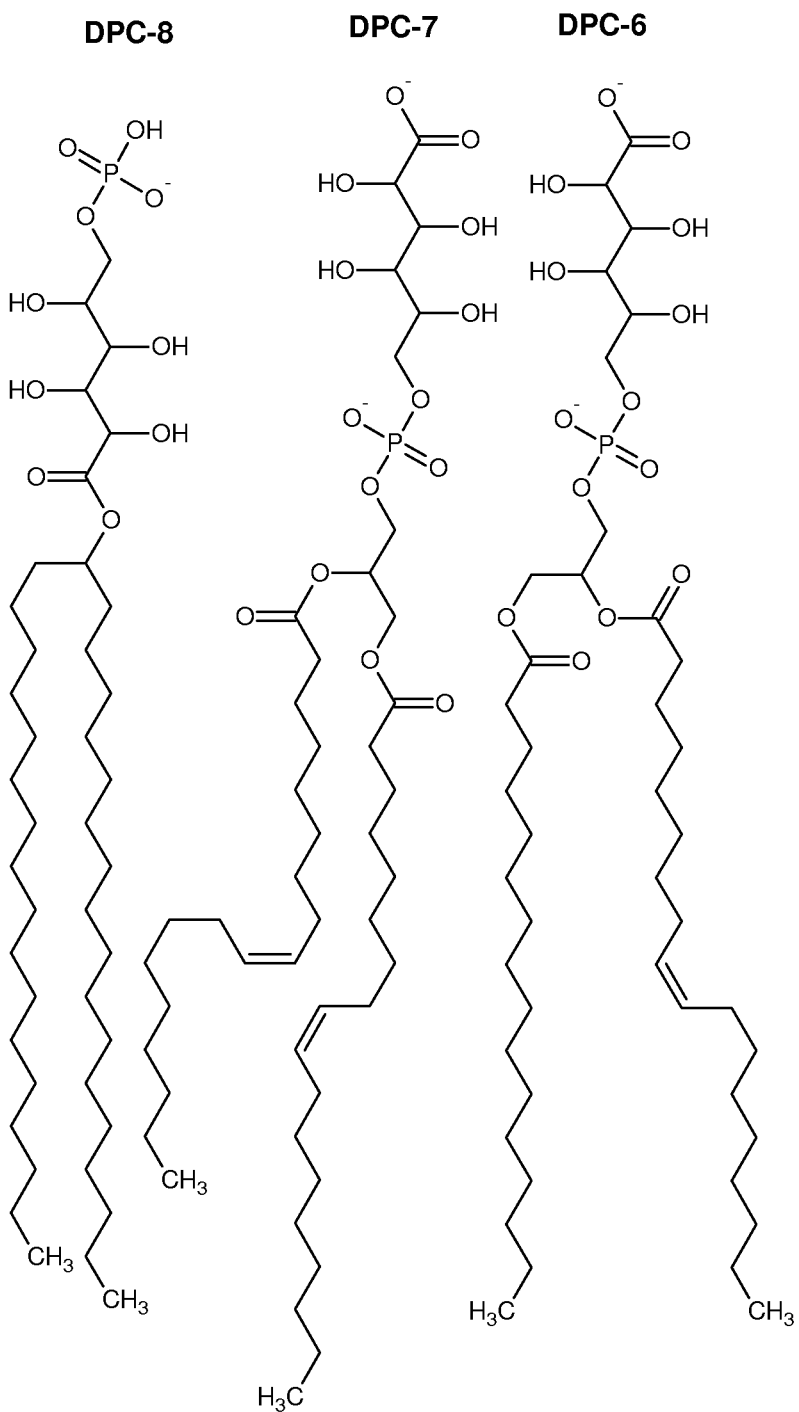

In one embodiment, the compound is DPC-12 shown in FIG. 12, or a compound of formula (II):
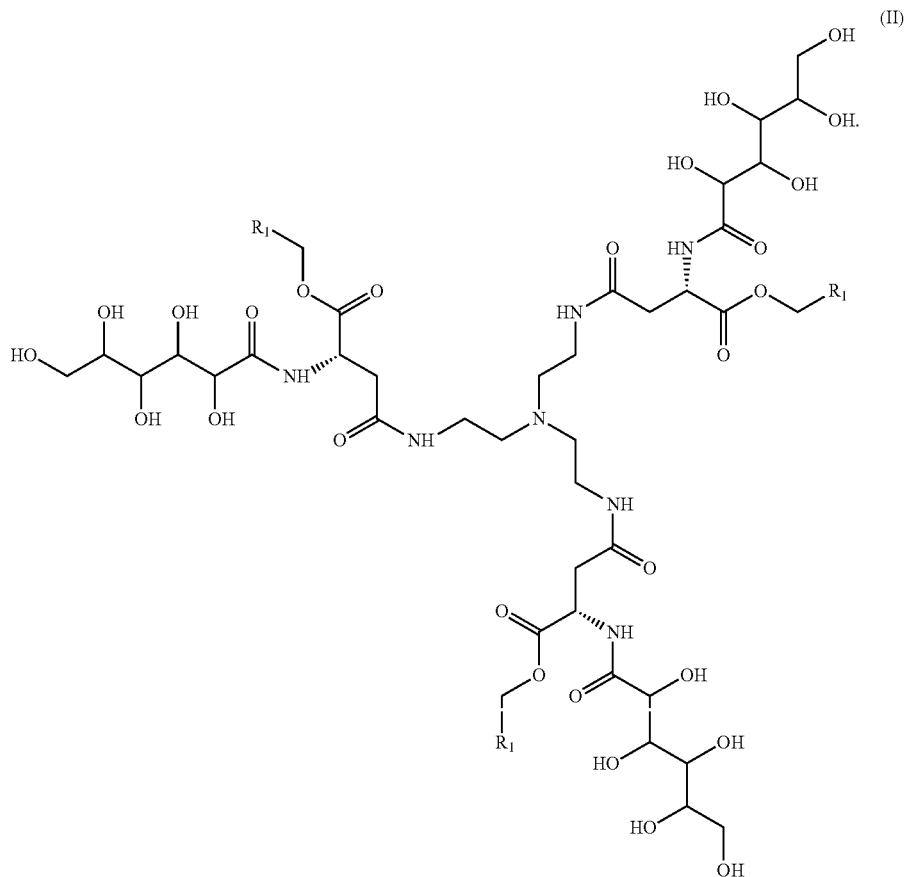
In one embodiment, the compound is (2,4-dihydroxy-6-oxo-6-(pentatriacontan-18-yloxy)hexyloxy)(hydroxy)(oxo) phosphonium, DPC-8 shown in FIG. 13, or
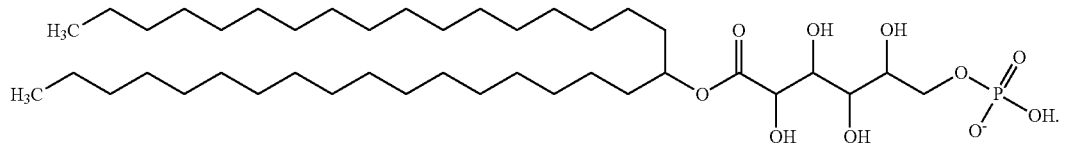 [SMILES: CCCCCCCCCCCCCCCCCC(CCCCCCCCCCCCCCCCC)OC(=O)C(O)C(O)C(O)C(O)COP(=O)([O-])O]
In one embodiment, the compound is 2,3-bis(oleoyloxy) propyl 2,3,4,5-tetrahydroxy-6-oxidohexyl phosphate, DPC-7 shown in FIG. 13, or
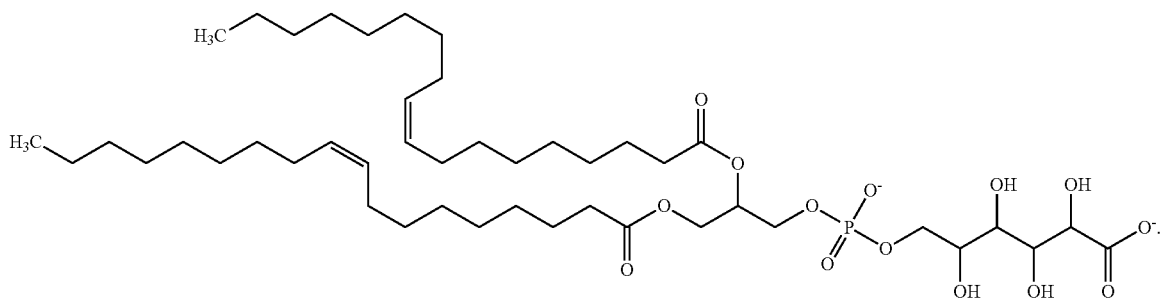

In one embodiment, the compound is (Z)-2-(oleoyloxy)-3-(palmitoyloxy)propyl 2,3,4,5-tetrahydroxy-6-oxidohexyl phosphate, DPC-6 shown in FIG. 13, or

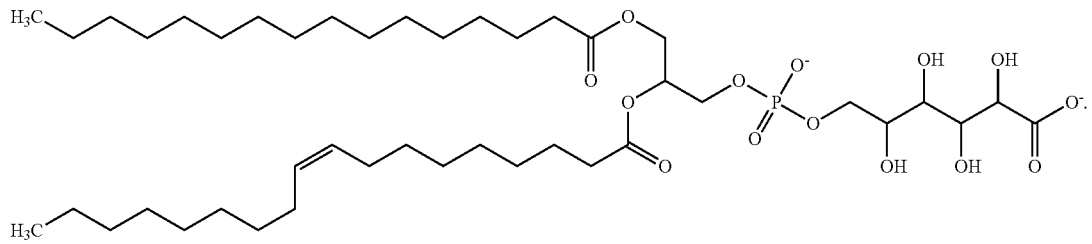

Figure 14:
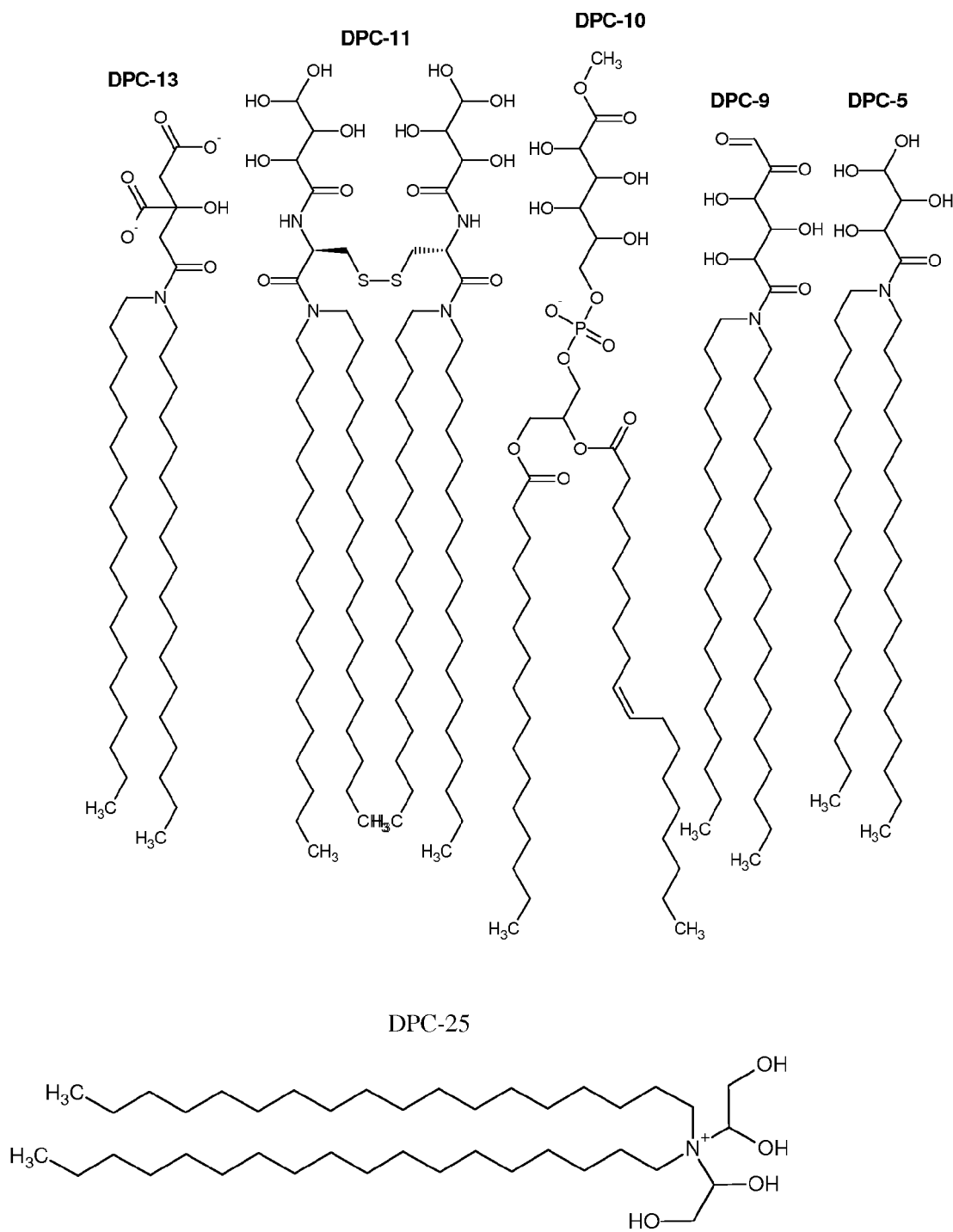

In one embodiment, the compound is 2-(2-(dioctadecylamino)-2-oxoethyl)-2-hydroxysuccinate, DPC-13 shown in FIG. 14, or

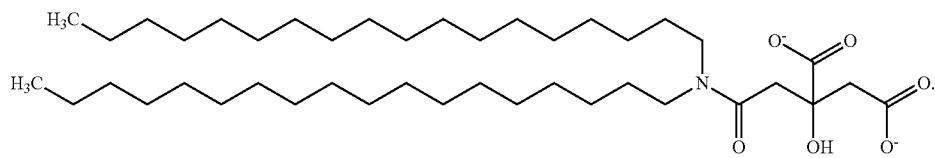 [SMILES: CCCCCCCCCCCCCCCCCCN(CCCCCCCCCCCCCCCCCC)C(=O)CC(O)(CC(=O)[O-])C(=O)[O-]]

In one embodiment, the compound is N,N'-(2R,2'R)-3,3'-disulfanediylbis(1-(dioctadecylamino)-1-oxopropane-3,2-diyl)bis(2,3,4,4-tetrahydroxybutanamide), DPC-11 shown in FIG. 14 or

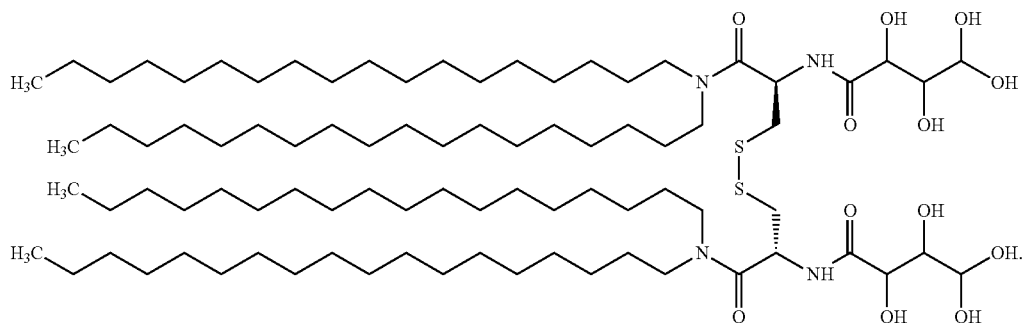 [SMILES: CCCCCCCCCCCCCCCCCCN(CCCCCCCCCCCCCCCCCC)C(=O)[C@H](CSSC[C@H](NC(=O)C(O)C(O)C(O)O)C(=O)N(CCCCCCCCCCCCCCCCCC)CCCCCCCCCCCCCCCCCC)NC(=O)C(O)C(O)C(O)O]

In one embodiment, the compound is (Z)-2-(oleoyloxy)-3-(palmitoyloxy)propyl 2,3,4,5-tetrahydroxy-6-methoxy-6-oxohexyl phosphate, DPC-10 shown in FIG. 14, or

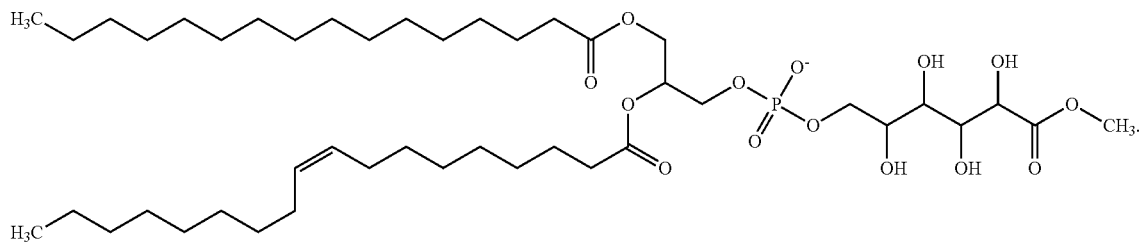 [SMILES: CCCCCCCC/C=C\CCCCCCCC(=O)OC(COC(=O)CCCCCCCCCCCCCCC)COP(=O)([O-])OCC(O)C(O)C(O)C(O)C(=O)OC]

In one embodiment, the compound is 2,3,4-trihydroxy-N,N-dioctadecyl-5,6-dioxohexanamide, DPC-9 shown in FIG. 14, or

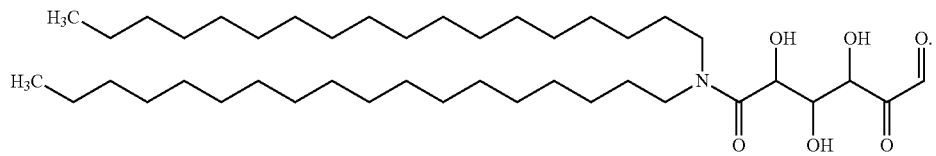 [SMILES: CCCCCCCCCCCCCCCCCCN(CCCCCCCCCCCCCCCCCC)C(=O)C(O)C(O)C(O)C(=O)C=O]

In one embodiment, the compound is 2,3,4,4-tetrahydroxy-N,N-dioctadecylbutanamide, DPC-5 shown in FIG. 14, or

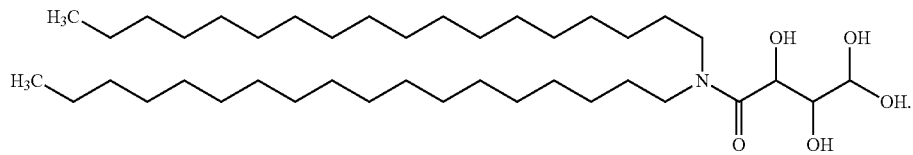 [SMILES: CCCCCCCCCCCCCCCCCCN(CCCCCCCCCCCCCCCCCC)C(=O)C(O)C(O)C(O)O]

In a related embodiment, the compound is DPC-25 shown in FIG. 14, or

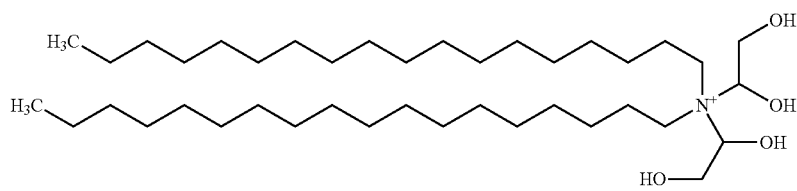 [SMILES: CCCCCCCCCCCCCCCCCC[N+](CCCCCCCCCCCCCCCCCC)(C(O)CO)C(O)CO]

In one embodiment, the compound is 6-(((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)oxidophosphoryloxy)-2,3,4,5-tetrahydroxyhexanoate, DPC-4 shown in FIG. 7, or

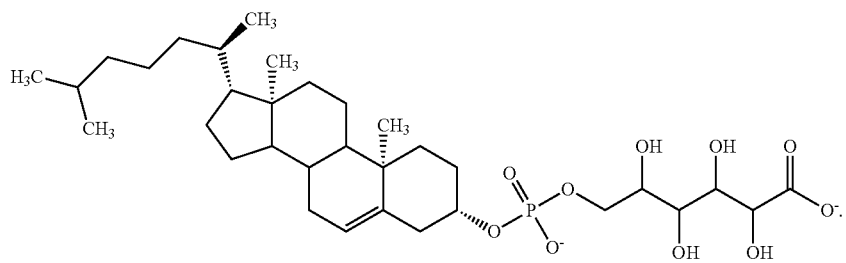

Figure 6:
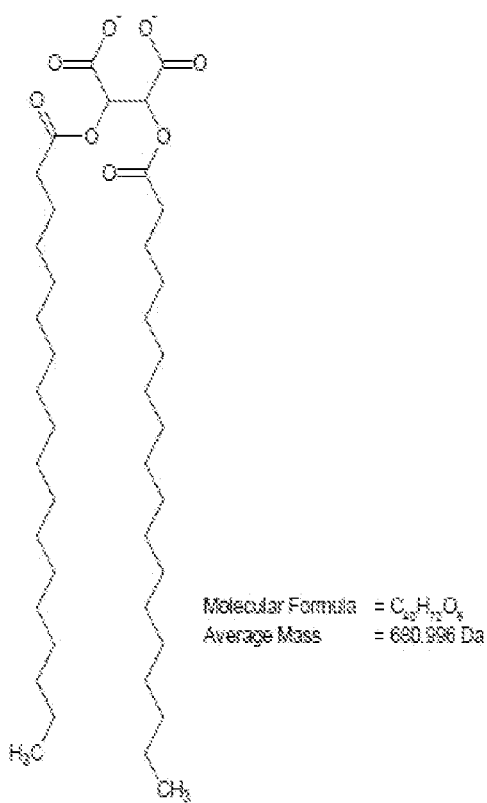
Figure 8:
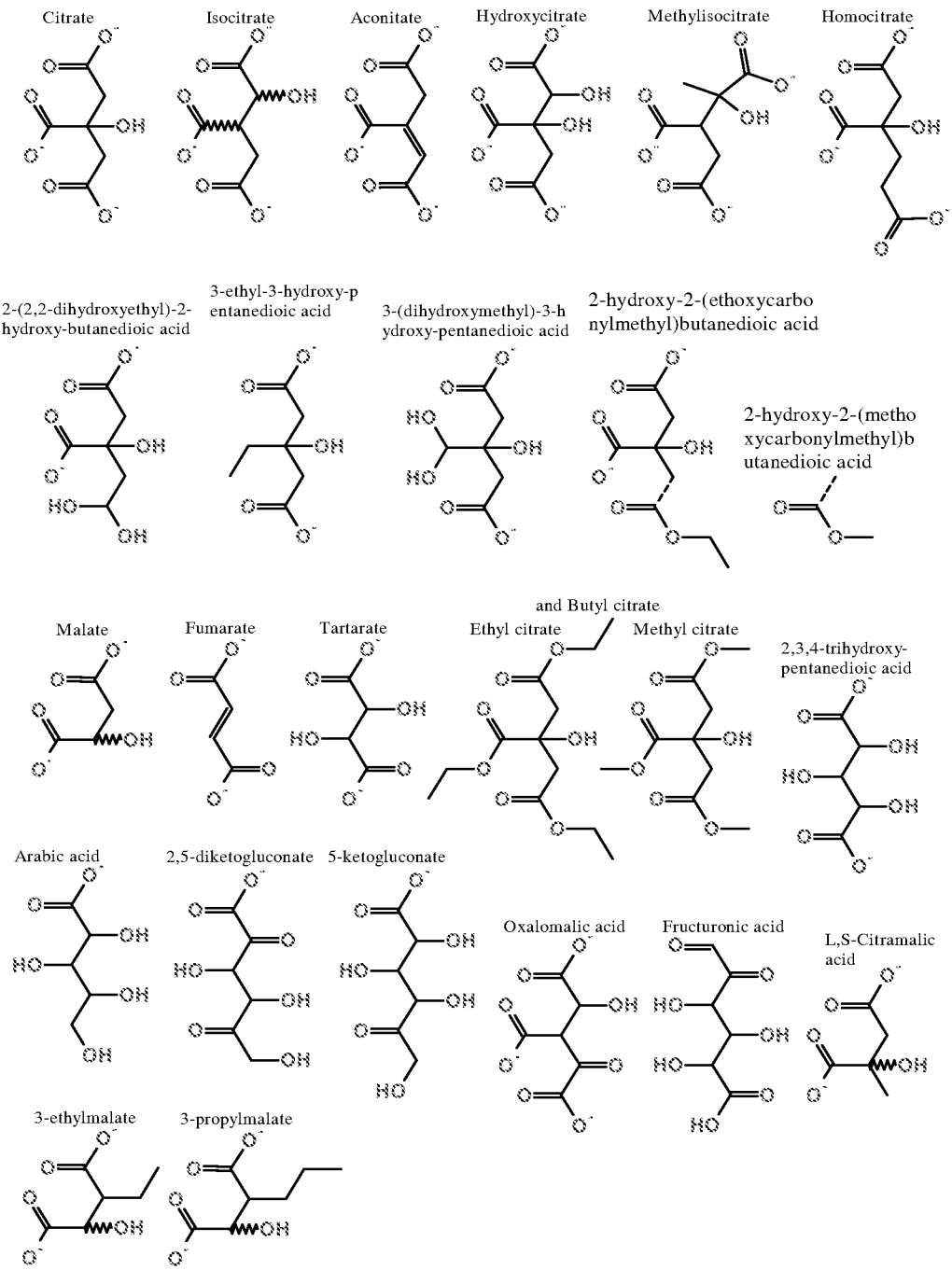

In one embodiment, the compound is 2,3-bis(stearoyloxy)succinate, DPC-036 shown in FIG. 6, or

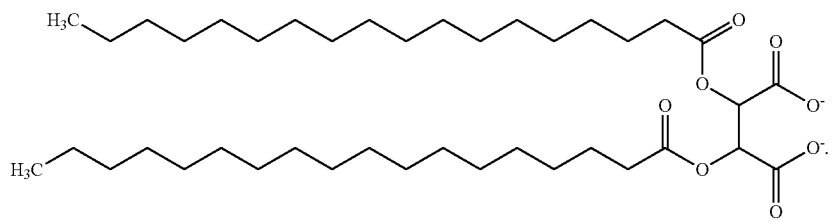

Formulations of Immunogenic or Immunostimulatory Cargoes

In one aspect, the present invention provides formulations containing immunogenic or immunostimulatory cargoes, e.g., nucleic acid cargoes (e.g., dsRNAs such as DsiRNAs) such as those described herein. In certain embodiments, the formulation is a lipid-based carrier system such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. Nucleic acid-lipid particles and their method of preparation are disclosed in, e.g., U.S. Pat. Nos. 5,753,613; 5,785,992; 5,705,385; 5,976,567; 5,981,501; 6,110,745; and 6,320,017; and PCT Publication No. WO 96/40964, which are all herein incorporated by reference.

In addition to the immune response reducing lipids recited above, the formulations of the instant invention can also include one or more of the following:

Non-Cationic Lipids

Non-cationic lipids used in the formulations of the present invention can be any of a variety of neutral uncharged, zwitterionic, or anionic lipids capable of producing a stable complex. Such non-cationic lipids can be neutral or negatively charged. Examples of non-cationic lipids include, without limitation, phospholipid-related materials such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipahnitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), and stearoyloleoyl-phosphatidylethanolamine (SOPE). Non-cationic lipids or sterols such as cholesterol may also be present. Additional nonphosphorous containing lipids include, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, diacylphosphatidylcholine, diacylphosphatidylethanolamine, and the like. Other lipids such as lysophosphatidylcholine and lysophosphatidylethanolamine may be present. Non-cationic lipids also include polyethylene glycol (PEG)-based polymers such as PEG 2000, PEG 5000, and polyethylene glycol conjugated to phospholipids or to ceramides (referred to as PEG-Cer), as described in U.S. patent application Ser. No. 08/316,429.

In certain embodiments, the non-cationic lipids are diacylphosphatidylcholine (e.g., distearoylphosphatidylcholine, dioleoylphosphatidylcholine, dipalmitoylphosphatidylcholine, and dilinoleoylphosphatidylcholine), diacylphosphatidylethanolamine (e.g., dioleoylphosphatidylethanolamine and palmitoyloleoyl-phosphatidylethanolamine), ceramide, or sphingomyelin. In particular embodiments, the acyl groups in these lipids are acyl groups derived from fatty acids having $C_{10}$-$C_{24}$ carbon chains. Optionally, the acyl groups are lauroyl, myristoyl, palmitoyl, stearoyl, or oleoyl. In certain embodiments, the non-cationic lipid may comprise from about 5 mol % to about 90 mol % or about 15 mol % to about 75 mol % or about 20 mol % to about 50 mol % or about 40 mol % of the total lipid present in the formulation. The non-cationic lipid typically comprises from about 10 mol % to about 85 mol %, from about 20 mol % to about 80 mol %, or about 20 mol % of the total lipid present in the formulation.

Cationic Lipids

A cationic lipid of a formulation of the instant invention may be, e.g., N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxypropylamine (DODMA), 1,2-DiLinoleyloxy-N,N-dimethylaminopropane (DLinDMA), 1,2-Dilinolenyloxy-N,N-dimethylaminopropane (DLendMA), DSDMA, DOSPA, DOGS, DC-Chol, DMRIE or mixtures thereof.

A number of these lipids and related analogs have been described in U.S. Patent Publication No. 20060083780; U.S. Pat. Nos. 5,208,036; 5,264,618; 5,279,833; 5,283,185; 5,753,613; and 5,785,992; and PCT Publication No. WO 96/10390. Additionally, a number of commercial preparations of cationic lipids are available and can be used in the present invention. These include, for example, LIPOFECTIN® (commercially available cationic liposomes comprising DOTMA and DOPE, from GEBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

In certain embodiments, the cationic lipid may comprise from about 5 mol % to about 90 mol %, about 10 mol % to about 60 mol %, or about 40 mol % of the total lipid present in the formulation. The cationic lipid typically comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % of the total lipid present in the formulation. It will be readily apparent to one of skill in the art that depending on the intended use of the formulations, the proportions of the components can be varied and the delivery efficiency of a particular formulation can be measured using, e.g., an endosomal release parameter (ERP) assay. For example, for systemic delivery, the cationic lipid may comprise from about 5 mol % to about 15 mol % of the total lipid present in the particle, and for local or regional delivery, the cationic lipid may comprise from about 30 mol % to about 50 mol %, or about 40 mol % of the total lipid present in the formulation.

The formulations of the instant invention may further comprise cholesterol. If present, the cholesterol typically comprises from about 0 mol % to about 10 mol %, from about 2 mol % to about 10 mol %, from about 10 mol % to about 60 mol %, from about 12 mol % to about 58 mol %, from about 20 mol % to about 55 mol %, from about 30 mol % to about 50 mol %, or about 48 mol % of the total lipid present in the formulation.

Conjugated lipids may also be included in the formulations of the invention, including a polyethyleneglycol (PEG)-lipid conjugate, a polyamide (ATTA)-lipid conjugate, a cationic-polymer-lipid conjugate (CPL), an aliphatic poly($\alpha$-hydroxy acids)-lipid conjugate, such as poly(D-, L-, or D, L-lactic acid; PLA)-lipid and poly(glycolic acid; PGA)-lipid and a copolymer-lipid (PLGA-lipid) conjugate thereof, or other art-recognized non-PEG hydrophilic polymer, or mixtures thereof including any of the preceding conjugates. In certain embodiments, a nucleic acid-lipid formulation of the invention comprises either a PEG-lipid conjugate or an ATTA-lipid conjugate. Optionally, a PEG-lipid conjugate or ATTA-lipid conjugate is used together with a CPL. A conjugated lipid of a formulation of the invention may comprise a PEG-lipid including, e.g., a PEG-diacylglycerol (DAG), a PEG dialkyloxypropyl (DAA), a PEG-phospholipid, a PEG-ceramide (Cer), or mixtures thereof. A PEG-DAA conjugate may be a PEG-dilauryloxypropyl (C12), a PEG-dimyristyloxypropyl (C14), a PEG-dipalmityloxypropyl (C16), or a PEG-distearyloxypropyl (C18). Optionally, a conjugated lipid is a CPL that has the formula: A-W—Y, wherein A is a lipid moiety, W is a hydrophilic polymer, and Y is a polycationic moiety. W may be a polymer selected from the group consisting of PEG, polyamide, polylactic acid, polyglycolic acid, polylactic acid/polyglycolic acid copolymers, or combinations thereof, the polymer having a molecular weight of from about 250 to about 7000 daltons. In some embodiments, Y has at least 4 positive charges at a selected pH. In some embodiments, Y may be lysine, arginine, asparagine, glutamine, derivatives thereof, or combinations thereof. In certain embodiments, a conjugated lipid is present in a formulation of the instant invention from 0 mol % to about 20 mol % or about 2 mol % of the total lipid present in the formulation.

Stabilizing Components

In addition to cationic and non-cationic lipids, a formulation of the present invention can comprise a stabilizing component (SC) such as an ATTA-lipid or a PEG-lipid such as PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides, or a mixture thereof (see, e.g., U.S. Pat. No. 5,885,613). In certain embodiments, the SC is a conjugated lipid that prevents the aggregation of formulation particles. Suitable conjugated lipids include, but are not limited to, PEG-lipid conjugates, ATTA-lipid conjugates, cationic-polymer-lipid conjugates (CPLs), and mixtures thereof. In additional embodiments, formulation particles comprise either a PEG-lipid conjugate or an ATTA-lipid conjugate together with a CPL.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-CH$_2$COOH) is particularly useful for preparing PEG-lipid conjugates including, e.g., PEG-DAA conjugates.

In certain embodiments, a PEG used in a formulation of the invention has an average molecular weight of from about 550 daltons to about 10,000 daltons, optionally from about 750 daltons to about 5,000 daltons, optionally from about 1,000 daltons to about 5,000 daltons, optionally from about 1,500 daltons to about 3,000 daltons, and optionally about 2,000 daltons or about 750 daltons. The PEG can be optionally substituted by an alkyl, alkoxy, acyl, or aryl group. The PEG can be conjugated directly to the lipid or may be linked to the lipid via a linker moiety. A linker moiety suitable for coupling the PEG to a lipid can be used including, e.g., non-ester containing linker moieties and ester-containing linker moieties. In certain embodiments, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). Optionally, a carbamate linker is used to couple the PEG to the lipid.

In other embodiments, an ester containing linker moiety can be used to couple PEG to a lipid. Exemplary ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form a stabilizing component. Such phosphatidylethanolamines are commercially available, or can be isolated or synthesized using conventional techniques known to those of skilled in the art. Exemplary phosphatidylethanolamines contain saturated or unsaturated fatty acids with carbon chain lengths in the range of $C_{10}$ to $C_{20}$. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

In addition to the foregoing components, formulation particles of the present invention can further comprise cationic poly(ethylene glycol) (PEG) lipids or CPLs that have been designed for insertion into lipid bilayers to impart a positive charge (see, e.g., Chen et al., *Bioconj. Chem.*, 11:433-437 (2000)). Exemplary SPLPs and SPLP-CPLs that can be used in the formulations of the instant invention, and methods of making and using SPLPs and SPLP-CPLs, are disclosed, e.g., in U.S. Pat. No. 6,852,334 and PCT Publication No. WO 00/62813. Cationic polymer lipids (CPLs) which may also be used in the formulations of the instant invention in the present invention have the following architectural features: (1) a lipid anchor, such as a hydrophobic lipid, for incorporating the CPLs into the lipid bilayer; (2) a hydrophilic spacer, such as a polyethylene glycol, for linking the lipid anchor to a cationic head group; and (3) a polycationic moiety, such as a naturally occurring amino acid, to produce a protonizable cationic head group.

In certain instances, the formulations of the invention comprise a ligand, such as a targeting ligand. In certain instances, the ligand of the formulation has a positive charge. Exemplary ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

The stabilizing component (e.g., PEG-lipid) can comprise from about 0 mol % to about 20 mol %, from about 0.5 mol % to about 20 mol %, from about 1.5 mol % to about 18 mol %, from about 4 mol % to about 15 mol %, from about 5 mol % to about 12 mol %, or about 2 mol % of the total lipid present in the formulation. One of ordinary skill in the art will appreciate that the concentration of a stabilizing component can be varied depending on the stabilizing component employed and the rate at which the formulation (e.g., a formulation particle) is to become fusogenic.

By controlling the composition and concentration of a stabilizing component, one can control the rate at which the stabilizing component exchanges out of a lipid formulation (where the formulation forms a particle, a formulation particle) and, in turn, the rate at which the formulation becomes fusogenic. For instance, when a polyethyleneglycol-phosphatidylethanolamine conjugate or a polyethyleneglycol-ceramide conjugate is used as a stabilizing component, the rate at which a formulation becomes fusogenic can be varied, for example, by varying the concentration of the stabilizing component, by varying the molecular weight of the polyethyleneglycol, or by varying the chain length and degree of saturation of the acyl chain groups on the phosphatidylethanolamine or the ceramide. In addition, other variables including, for example, pH, temperature, ionic strength, etc. can be used to vary and/or control the rate at which a lipid formulation becomes fusogenic. Other methods which can be used to control the rate at which a formulation becomes fusogenic will become apparent to those of skill in the art upon reading this disclosure.

Other Carrier Systems

Non-limiting examples of additional lipid-based carrier systems suitable for use in the present invention include lipoplexes (see, e.g., U.S. Patent Publication No. 20030203865; and Zhang et al., *J. Control Release*, 100:165-180 (2004)), pH-sensitive lipoplexes (see, e.g., U.S. Patent Publication No. 2002/0192275), reversibly masked lipoplexes (see, e.g., U.S. Patent Publication Nos. 2003/0180950), cationic lipid-based compositions (see, e.g., U.S. Pat. No. 6,756,054; and U.S. Patent Publication No. 2005/0234232), cationic liposomes (see, e.g., U.S. Patent Publication Nos. 2003/0229040, 2002/0160038, and 2002/0012998; U.S. Pat. No. 5,908,635; and PCT Publication No. WO 01/72283), anionic liposomes (see, e.g., U.S. Patent Publication No. 2003/0026831), pH-sensitive liposomes (see, e.g., U.S. Patent Publication No. 2002/0192274; and AU 2003/210303), antibody-coated liposomes (see, e.g., U.S. Patent Publication No. 2003/0108597; and PCT Publication No. WO 00/50008), cell-type specific liposomes (see, e.g., U.S. Patent Publication No. 2003/0198664), liposomes containing nucleic acid and peptides (see, e.g., U.S. Pat. No. 6,207,456), liposomes containing lipids derivatized with releasable hydrophilic polymers (see, e.g., U.S. Patent Publication No. 2003/0031704), lipid-entrapped nucleic acid (see, e.g., PCT Publication Nos. WO 03/057190 and WO 03/059322), lipid-encapsulated nucleic acid (see, e.g., U.S. Patent Publication No. 2003/0129221; and U.S. Pat. No. 5,756,122), other liposomal compositions (see, e.g., U.S. Patent Publication Nos. 2003/0035829 and 2003/0072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 2005/0037086).

Examples of polymer-based carrier systems suitable for use in the present invention include, but are not limited to, cationic polymer-nucleic acid complexes (i.e., polyplexes). To form a polyplex, cargo (e.g., a nucleic acid such as a DsiRNA) is typically complexed with a cationic polymer having a linear, branched, star, or dendritic polymeric structure that condenses the cargo into positively charged particles capable of interacting with anionic proteoglycans at the cell surface and entering cells by endocytosis. In some embodiments, the polyplex comprises nucleic acid (e.g., DsiRNA) complexed with a cationic polymer such as polyethylenimine (PEI) (see, e.g., U.S. Pat. No. 6,013,240; commercially available from Qbiogene, Inc. (Carlsbad, Calif.) as In vivo jet-PEI®, a linear form of PEI), polypropylenimine (PPI), polyvinylpyrrolidone (PVP), poly-L-lysine (PLL), diethylaminoethyl (DEAE)-dextran, poly(β-amino ester) (PAE) polymers (see, e.g., Lynn et al., *J. Am. Chem. Soc.*, 123:8155-8156 (2001)), chitosan, polyamidoamine (PAMAM) dendrimers (see, e.g., Kukowska-Latallo et al., *Proc. Natl. Acad. Sci. USA*, 93:4897-4902 (1996)), porphyrin (see, e.g., U.S. Pat. No. 6,620,805), polyvinylether (see, e.g., U.S. Patent Publication No. 20040156909), polycyclic amidinium (see, e.g., U.S. Patent Publication No. 20030220289), other polymers comprising primary amine, imine, guanidine, and/or imidazole groups (see, e.g., U.S. Pat. No. 6,013,240; PCT Publication No. WO/9602655; PCT Publication No. WO95/21931; Zhang et al., *J. Control Release*, 100:165-180 (2004); and Tiera et al., *Curr. Gene Ther.*, 6:59-71 (2006)), and a mixture thereof. In other embodiments, the polyplex comprises cationic polymer-nucleic acid complexes as described in U.S. Patent Publication Nos. 2006/0211643, 2005/0222064, 2003/0125281, and 2003/0185890, and PCT Publication No. WO 03/066069; biodegradable poly(β-amino ester) polymer-nucleic acid complexes as described in U.S. Patent Publication No. 2004/0071654; microparticles containing polymeric matrices as described in U.S. Patent Publication No. 2004/0142475; other microparticle compositions as described in U.S. Patent Publication No. 2003/0157030; condensed nucleic acid complexes as described in U.S. Patent Publication No. 2005/0123600; and nanocapsule and microcapsule compositions as described in AU 2002358514 and PCT Publication No. WO 02/096551.

In certain instances, the cargo (e.g., a nucleic acid such as a DsiRNA) may be complexed with cyclodextrin or a polymer thereof. Non-limiting examples of cyclodextrin-based carrier systems include the cyclodextrin-modified polymer-nucleic acid complexes described in U.S. Patent Publication No. 2004/0087024; the linear cyclodextrin copolymer-nucleic acid complexes described in U.S. Pat. Nos. 6,509,323, 6,884,789, and 7,091,192; and the cyclodextrin polymer-complexing agent-nucleic acid complexes described in U.S. Pat. No. 7,018,609. In certain other instances, the cargo (e.g., a nucleic acid such as a DsiRNA) may be complexed with a peptide or polypeptide. An example of a protein-based carrier system includes, but is not limited to, the cationic oligopeptide-nucleic acid complex described in PCT Publication No. WO95/21931.

Preparation of the Immune Response Reducing Lipids of the Invention

The present invention contemplates any suitable source and/or any known or attainable process available to one of ordinary skill in the art to obtain and/or prepare any of the lipids of the invention, e.g., the immune response reducing lipids of the invention, including any non-cationic or cationic lipid described here. In certain embodiments, the lipids (or the starting materials used in the synthesis of the lipids) of the invention can be obtained from commercial sources (e.g., Sigma-Aldrich Co.). In other embodiments, the lipids of the invention can be obtained from natural sources, such as, but not limited to microorganisms, animals, plants, or other biological systems. In still other embodiments, the lipids of the invention can be prepared using enzymatic processes well known to those of ordinary skill in the art. In certain other embodiments, the lipids of the invention, e.g., those non-cationic lipids of FIGS. 9-14, can be prepared using the synthetic schemes described herein which can involve the assembly of the final lipid molecule having distinguishable moieties, e.g., a lipophilic moiety, a linker moiety, and a head group polar moiety as shown in FIG. 7, through the enzymatic and/or chemical assemblage of appropriate starting components. Generally, enzymatic and/or chemical synthesis techniques necessary to prepare and/or obtain the various lipids of the invention will be well-known to those of ordinary skill in the art and thus, the description herein concerning the preparation of certain exemplary lipids is not intended to limit the invention in any way.

It will be appreciated by those of ordinary skill in the art that the general chemistry, synthesis, manufacture and sources of lipids is well known and published information and guidance regarding such is readily available in the art and which may be relied upon in the preparation of the lipids of the invention. For information and guidance as to the synthesis (e.g., enzymatic and/or chemical synthesis), manufacture, properties, and characteristics of lipids, the skilled artisan can refer to any suitable treatise, book or journal article or the like that pertains to such information, including, but not limited to: *Lipid Synthesis And Manufacture* (Chemistry And Technology Of Oils And Fats), Academic Press, Eds. Sheffield, 1998; *Fatty Acid And Lipid Chemistry*, Aspen Publishers, Eds. F. D. Gunstone, Frank Gunstone, 1996; *Modifying Lipids For Use In Food*, CRC Press, Eds. F. Gunstone, F. Gunstone, Frank 17. Gunstone, 2006; *Lipid Technologies And Applications*, CRC Press, Eds. Frank D. Gunstone, Gunstone D. Gunstone, Frank D. Gunstone, 1997; *The Chemistry Of Oils & Fats Sources Composition Properties & Uses*, Blackwell Science Ltd., Ed. Frank D Gunstone, 2005; and *Lipid Analysis Of Oils And Fats*. Springer Netherlands, Eds. R. J. Hamilton, M.d. Hamilton, Richard Hamilton, 1997, the contents of each of which are incorporated by reference.

As noted, in certain embodiments, the lipids of the invention, or starting materials that can be used to prepare the lipids of the invention, can be obtained from natural sources, such as, but not limited to microorganisms, animals, plants, or other biological systems. For example, certain lipids of the invention comprise fatty acid moieties. Methods for preparing and/or isolating fatty acids from biological sources for use in the lipids of the invention can be found in U.S. Pat. No. 7,579,174 (Enhanced production of lipids containing polyenoic fatty acid by very high density cultures of eukaryotic microbes in fermentors), U.S. Pat. No. 6,607,900 (Enhanced production of lipids containing polyenoic fatty acid by very high density cultures of eukaryotic microbes in fermentors), U.S. Pat. No. 6,582,941 (Microorganisms capable of producing highly unsaturated fatty acids and process for producing highly unsaturated fatty acids by using the microorganisms), U.S. Pat. No. 6,451,567 (Fermentation process for producing long chain omega-3 fatty acids with euryhaline microorganisms), U.S. Pat. No. 6,255,505 (Microbial polyunsaturated fatty acid containing oil from pasteurised biomass), and U.S. Pat. No. 6,140,486 (Production of polyunsaturated fatty acids by expression of polyketide-like synthesis genes in plants), each of which are incorporated herein by reference.

In other embodiments, the lipids of the invention comprise sterol moieties (e.g., cholesterol). Methods for preparing and/or isolating such sterols from biological sources for use in the lipids of the invention can be found in U.S. Pat. Nos. 2,729,655, 3,153,055, 3,335,154, 3,840,570, 4,148,810, 4,374,776, 4,451,564, 6,660,491, and 5,219,733, each of which are incorporated herein by reference. Sterols which may be used for the purposes of the invention may include those obtained from natural products such as, for example, soya, rapeseed, sunflower, coconut, palm kernel and palm oil. Preferred sterols are sigmasterol, campesterol, sitosterol, brassicasterols, stigmasterol, D5 avenasterol, D7 avenasterol, ergosterol, citrostadienol, cholesterol, lanosterols, spongosterols, fungi sterols, stellasterols, zymosterols and mixtures thereof and, phytosterols based on ergosterols, avenasterols (D5 and D7 avenasterol), campesterols, stigmasterols, sitosterols, brassicasterols, citrosdandiols, sigmastandiols and mixtures thereof. Any other phytosterols known to the expert may also be used. Their composition is described in "Sterinzusammensetzung und Steringehalt in 41 verschiedenen pflanzlichen und tierischen Fetten", E. Homberg; B. Bielefeld; Fat Sci. Technol, Vol. 91, No. 1, 1989, which is incorporated herein by reference.

Accordingly, it will be appreciated that the components of formula (I) $R_1$—$R_2$—$R_3$ (I) can be readily obtained, e.g., via synthesis using well-known chemistries or obtained from natural sources, such as, from plants or microorganisms, or synthesized enzymatically, or even obtained commercially.

Thus, one of ordinary skill in the art can readily obtain any of the lipophilic moieties of $R_1$ of formular (I), including a single sterol, a dimeric sterol, a multimeric sterol, a single alkyl chain from 5 to 24 carbon atoms, a multiple alkyl chain from 5 to 24 carbon atoms each, a single symmetric branched alkyl moiety from 10 to 50 carbon atoms each, a multiple symmetric branched alkyl moiety from 10 to 50 carbon atoms each, a single asymmetric branched alkyl chain ranging from 10 to 50 carbons each, a multiple asymmetric branched alkyl chain ranging from 10 to 50 carbons each, a single alkenyl chain containing one or more unsaturations from 5 to 24 carbon atoms, a multiple alkyl chain containing one or more unsaturations from 5 to 24 carbon atoms each, a single symmetric branched alkyl moiety containing one or more unsaturations from 10 to 50 carbon atoms each, a multiple symmetric branched alkyl moiety containing one or more unsaturations from 10 to 50 carbon atoms each, a single asymmetric branched alkyl chain containing one or more unsaturations ranging from 10 to 50 carbons each, a multiple asymmetric branched alkyl chain containing one or more unsaturations ranging from 10 to 50 carbons each, a mixed alkyl chain from 5 to 24 carbon atoms, and an alkenyl chain containing one or more unsaturations from 5 to 24 carbon atoms;

Additionally, one of ordinary skill in the art can readily obtain any of the negatively charged or neutral moieties linking $R_1$ and $R_3$ selected a phosphate ester, a neutral phosphonate, a carbamate, an amide, one or more neutral or negatively charged amino acids, an ether, a ketone, an ester, an alkyl chain from one to 10 carbons, and a disulfide linked moiety. Similarly, the $R_3$ moieties, including a negatively charged or neutral moiety comprising two or more hydroxyls, carbonates, ethers, or carboxylates; or two or more alkyl esters from 1 to 6 carbons; or two or more alkyl esters from 2 to 6 carbons can also be readily obtained.

The present invention contemplates any suitable chemical or enzymatic method or the like for preparing the lipids of the invention, including those lipids of FIGS. 9-14. The lipids of FIGS. 9-14 can be prepared by combining starting materials for $R_1$, $R_2$, and $R_3$ using any suitable chemical reaction scheme, such as those exemplified below.

Exemplary Synthetic Scheme for the Compound of FIG. 9:

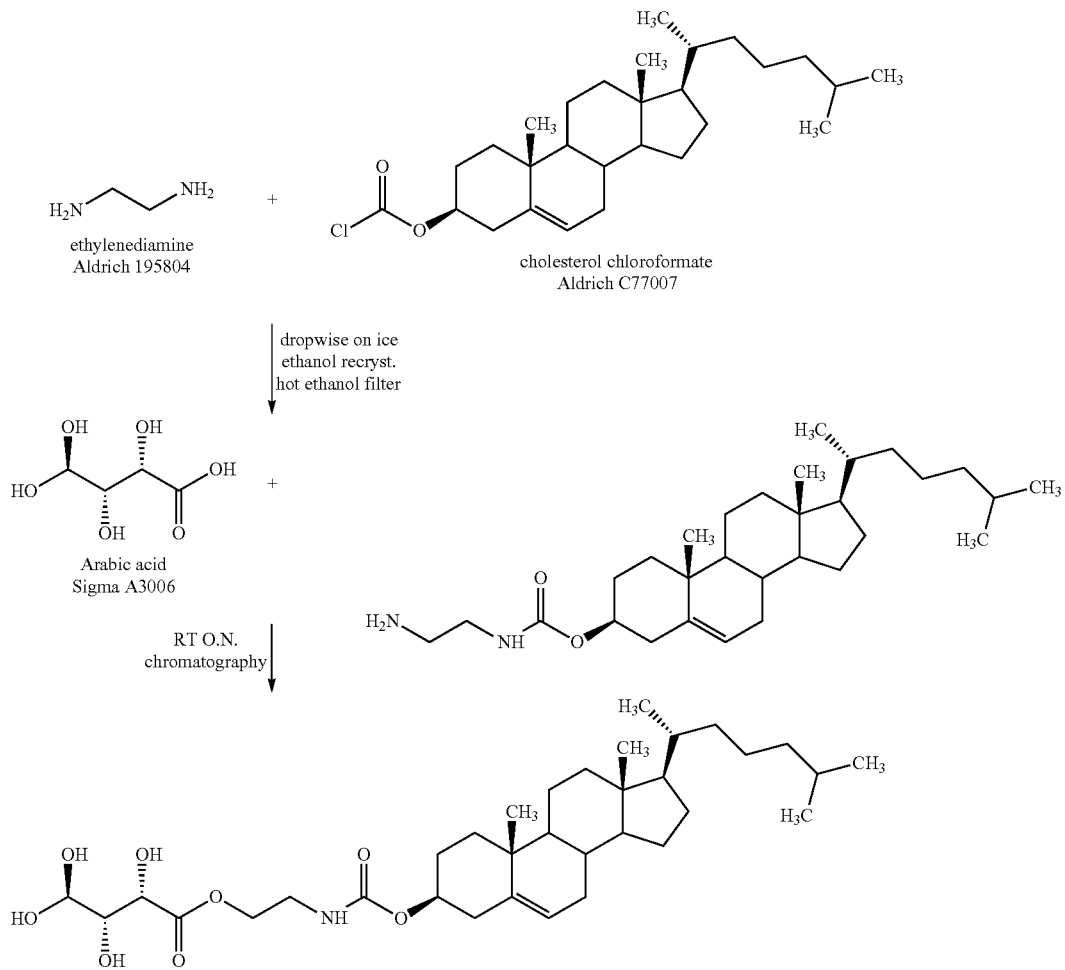

Exemplary Synthetic Scheme for the Compound of FIG. 10:

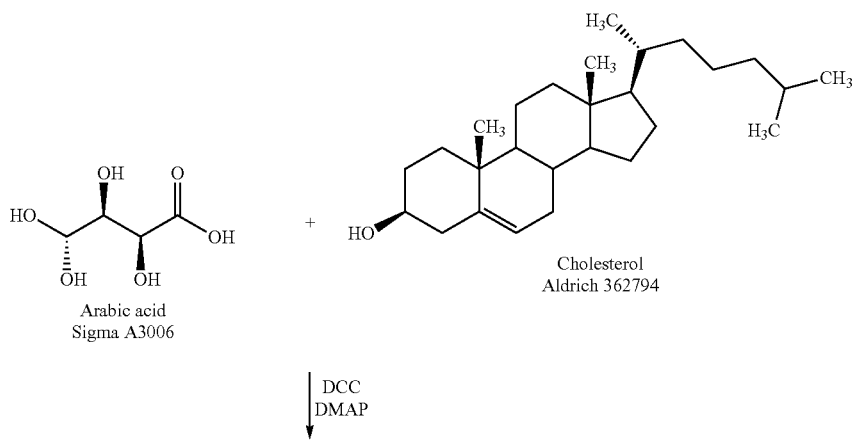

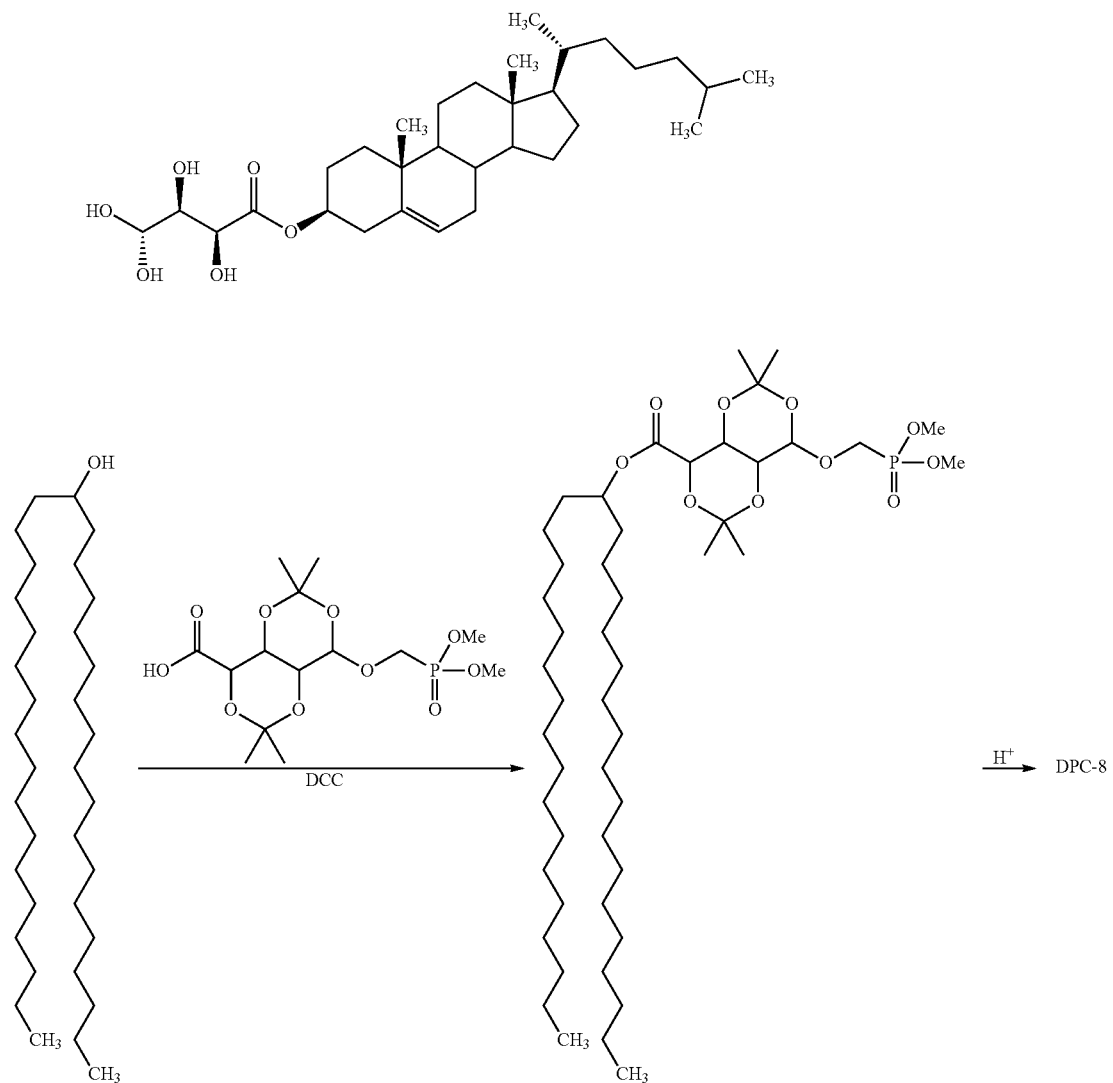
Exemplary Synthetic Scheme for the Compound of FIG. 11:
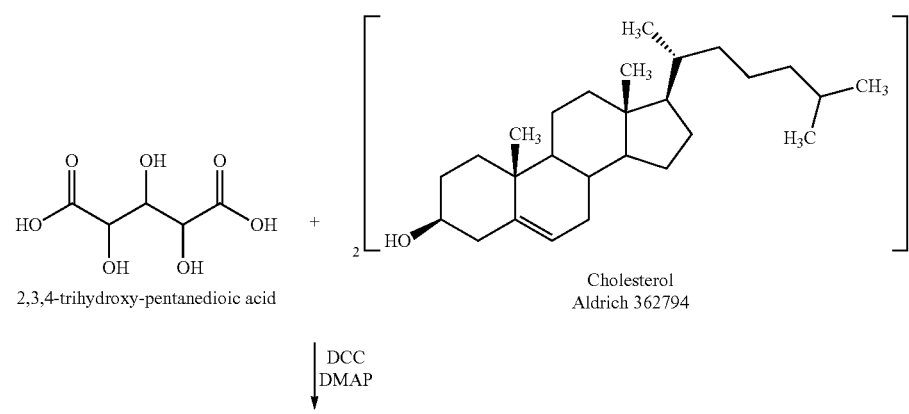
2,3,4-trihydroxy-pentanedioic acid
Cholesterol
Aldrich 362794
DCC
DMAP

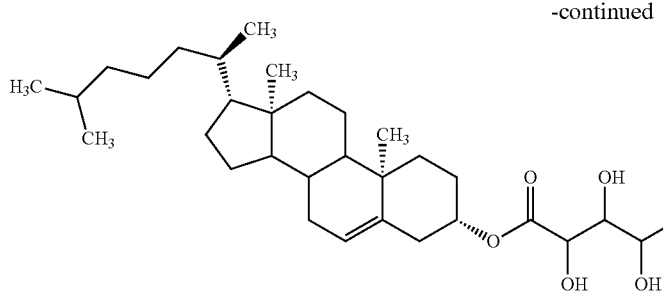

Preparation of Cargo-Lipid Formulation Particles

Certain formulations of the present invention, e.g., in which an immunogenic or immunostimulatory cargo (e.g., a DsiRNA) is encapsulated in a lipid bilayer and is protected from degradation, can be formed by a method known in the art including, but not limited to, a continuous mixing method, a direct dilution process, a detergent dialysis method, or a modification of a reverse-phase method which utilizes organic solvents to provide a single phase during mixing of the components.

In certain embodiments, the immune silencing lipids and any non-cationic and/or cationic lipids of the formulations of the invention are lipids as described above, or combinations thereof.

In particular embodiments, the organic solvents are methanol, chloroform, methylene chloride, ethanol, diethyl ether, propanol, isopropanol, or combinations thereof.

In specific embodiments, the present invention provides for cargo-lipid formulations produced via a continuous mixing method, e.g., a process that includes providing an aqueous solution comprising a cargo such as a DsiRNA in a first reservoir, providing an organic lipid solution in a second reservoir, and mixing the aqueous solution with the organic lipid solution such that the organic lipid solution mixes with the aqueous solution so as to substantially instantaneously produce a liposome encapsulating the cargo (e.g., DsiRNA). This process and the apparatus for carrying this process are described in detail in U.S. Patent Publication No. 2004/0142025.

The action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a cargo with the organic lipid solution, the organic lipid solution undergoes a continuous stepwise dilution in the presence of the buffer solution (i.e., aqueous solution) to produce a cargo-lipid formulation particle.

In certain embodiments, the serum-stable cargo-lipid formulation particles formed using the continuous mixing method can have a size of from about 30 nm to about 150 nm, from about 50 nm to about 130 nm, from about 60 nm to about 110 nm, or from about 70 nm to about 90 nm. The formulation particles thus formed do not aggregate and are optionally sized to achieve a uniform particle size.

In yet another embodiment, the present invention provides for cargo-lipid formulation particles produced via a direct dilution process in which a third reservoir containing dilution buffer is fluidly coupled to a second mixing region. In this embodiment, the liposome solution formed in a first mixing region is immediately and directly mixed with dilution buffer in the second mixing region. In certain aspects, the second mixing region includes a T-connector arranged so that the liposome solution and the dilution buffer flows meet as opposing 180° flows; however, connectors providing shallower angles can be used, e.g., from about 27° to about 180°. A pump mechanism delivers a controllable flow of buffer to the second mixing region. In one aspect, the flow rate of dilution buffer provided to the second mixing region is controlled to be substantially equal to the flow rate of liposome solution introduced thereto from the first mixing region. This embodiment advantageously allows for more control of the flow of dilution buffer mixing with the liposome solution in the second mixing region, and therefore also the concentration of liposome solution in buffer throughout the second mixing process. Such control of the dilution buffer flow rate advantageously allows for small particle size formation at reduced concentrations.

These processes and the apparatuses for carrying out these direct dilution processes is described in detail in U.S. patent application Ser. No. 11/495,150. The serum-stable cargo-lipid particles formed using the direct dilution process can have a size of from about 30 nm to about 150 nm, from about 50 nm to about 130 nm, from about 60 nm to about 110 nm, or from about 70 nm to about 90 nm. The particles thus formed do not aggregate and are optionally sized to achieve a uniform particle size. In some embodiments, the particles are formed using detergent dialysis. Without intending to be bound by any particular mechanism of formation, a cargo such as a DsiRNA is contacted with a detergent solution of cationic lipids to form a coated cargo complex. These coated cargoes can aggregate and precipitate. However, the presence of a detergent can reduce this aggregation and allow the coated cargoes to react with excess lipids (e.g., non-cationic lipids) to form particles in which the cargo is encapsulated in a lipid bilayer. Thus, serum-stable cargo-lipid particles can be prepared as follows:

(a) combining a cargo with cationic lipids in a detergent solution to form a coated cargo-lipid complex;
(b) contacting non-cationic lipids (including, e.g., immune response silencing lipids as described herein) with the coated cargo-lipid complex to form a detergent solution comprising a cargo-lipid complex and non-cationic lipids; and
(c) dialyzing the detergent solution of step (b) to provide a solution of serum-stable cargo-lipid particles, wherein the cargo is encapsulated in a lipid bilayer and the particles are serum-stable and have a size of from about 50 to about 150 nm.

An initial solution of coated cargo-lipid complexes is formed by combining the cargo with the cationic lipids in a detergent solution. In these embodiments, the detergent solution is optionally an aqueous solution of a neutral detergent having a critical micelle concentration of 15-300 mM, optionally 20-50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3-08; Zwittergent® 3-10; Triton X-405; hexyl-, heptyl-, octyl- and nonyl-β-D-glucopyranoside; and heptylthioglucopyranoside. In certain embodiments, the concentration of detergent in the detergent solution can be about 100 mM to about 2 M, optionally from about 200 mM to about 1.5 M.

In certain embodiments, cationic lipids, non-cationic lipids (e.g., immune response silencing lipids as described herein) and cargoes may be combined to produce a charge ratio (+/−) of about 1:1 to about 20:1, in a ratio of about 1:1 to about 12:1, or in a ratio of about 2:1 to about 6:1. Additionally, in certain embodiments, the overall concentration of cargo in solution can be from about 25 µg/ml to about 1 mg/ml, from about 25 µg/ml to about 200 µg/ml, or from about 50 µg/ml to about 100 µg/ml. The combination of cargoes and cationic lipids in detergent solution is kept, optionally, at room temperature, for a period of time which is sufficient for the coated complexes to form. Alternatively, the cargoes and cationic lipids can be combined in the detergent solution and warmed to temperatures of up to about 37° C., about 50° C., about 60° C., or about 70° C. For cargoes which are particularly sensitive to temperature, the coated complexes can be formed at lower temperatures, typically down to about 4° C. In some embodiments, the cargo to lipid ratios (mass/mass ratios) in a formed cargo-lipid particle will range from about 0.01 to about 0.2, from about 0.02 to about 0.1, from about 0.03 to about 0.1, or from about 0.01 to about 0.08. The ratio of the starting materials can also fall within this range. In other embodiments, the cargo-lipid particle preparation uses about 400 µg cargo per 10 mg total lipid or a cargo to lipid mass ratio of about 0.01 to about 0.08 and, optionally, about 0.04, which corresponds to 1.25 mg of total lipid per 50 µg of cargo. In certain embodiments, the particle has a cargo:lipid mass ratio of about 0.08.

A detergent solution of a coated cargo-lipid complex can then be contacted with non-cationic lipids to provide a detergent solution of cargo-lipid complexes and non-cationic lipids. Non-cationic lipids useful in this step include, diacylphosphatidylcholine, diacylphosphatidylethanolamine, ceramide, sphingomyelin, cephalin, cardiolipin, and cerebrosides. In certain embodiments, the non-cationic lipids are diacylphosphatidylcholine, diacylphosphatidylethanolamine, ceramide, or sphingomyelin. Acyl groups in these lipids are optionally acyl groups derived from fatty acids having $C_{10}$-$C_{24}$ carbon chains. In certain embodiments, the acyl groups are lauroyl, myristoyl, palmitoyl, stearoyl, or oleoyl. Optionally, the non-cationic lipids are DSPC, DOPE, POPC, egg phosphatidylcholine (EPC), cholesterol, a non-cationic immune response reducing lipid as described herein, or a mixture thereof. In certain embodiments, the cargo-lipid formulation particles are fusogenic particles with enhanced properties in vivo and the non-cationic lipid is DSPC or DOPE. In addition, the cargo-lipid formulation particles of the present invention may further comprise cholesterol. In other embodiments, the non-cationic lipids can further comprise polyethylene glycol-based polymers such as PEG 2,000, PEG 5,000, and PEG conjugated to a diacylglycerol, a ceramide, or a phospholipid, as described in, e.g., U.S. Pat. No. 5,820,873 and U.S. Patent Publication No. 2003/0077829. In further embodiments, the non-cationic lipids can further comprise polyethylene glycol-based polymers such as PEG 2,000, PEG 5,000, and PEG conjugated to a dialkyloxypropyl.

The amount of non-cationic lipid which is used in the present methods can be from about 2 to about 20 mg of total lipids to 50 µg of cargo. Optionally, the amount of total lipid is from about 5 to about 10 mg per 50 µs of cargo.

After formation of a detergent solution of cargo-lipid complexes and non-cationic lipids, the detergent can be removed, e.g., by dialysis. Detergent removal can result in the formation of a lipid-bilayer which surrounds the cargo providing serum-stable cargo-lipid formulation particles which have a size of from about 30 nm to about 150 nm, from about 50 nm to about 130 nm, from about 60 nm to about 110 nm, or from about 70 nm to about 90 nm. The formulation particles thus formed do not aggregate and are optionally sized to achieve a uniform particle size.

Serum-stable cargo-lipid formulation particles can be sized by any of the methods available for sizing liposomes. The sizing may be conducted in order to achieve a desired size range and relatively narrow distribution of particle sizes.

Several techniques are available for sizing the formulation particles to a desired size. One sizing method, used for liposomes and equally applicable to the present particles, is described in U.S. Pat. No. 4,737,323. Sonicating a formulation particle suspension either by bath or probe sonication cam produce a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the formulation particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The formulation particles may be extruded through successively smaller-pore membranes, to achieve a gradual reduction in size.

In another group of embodiments, serum-stable cargo-lipid particles can be prepared as follows:
  (a) preparing a mixture comprising cationic lipids and non-cationic lipids in an organic solvent;
  (b) contacting an aqueous solution of cargo with the mixture in step (a) to provide a clear single phase; and
  (c) removing the organic solvent to provide a suspension of cargo-lipid particles, wherein the cargo is encapsulated in a lipid bilayer and the particles are stable in serum and have a size of from about 50 to about 150 nm.

The cargoes (e.g., DsiRNA), cationic lipids, and non-cationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of cargo and lipids. Suitable solvents include, but are not limited to, chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol.

Combinations of two or more solvents may also be used. Contacting the cargo with the organic solution of cationic and non-cationic lipids is accomplished by mixing together a first solution of cargo, which is typically an aqueous solution, and a second organic solution of the lipids. One of skill in the art will understand that this mixing can take place by any number of methods, for example, by mechanical means such as by using vortex mixers.

After the cargo has been contacted with the organic solution of lipids, the organic solvent is removed, thus forming an aqueous suspension of serum-stable cargo-lipid particles. The methods used to remove the organic solvent will typically involve evaporation at reduced pressures or blowing a stream of inert gas (e.g., nitrogen or argon) across the mixture.

Serum-stable cargo-lipid particles thus formed will typically be sized from about 30 nm to about 150 nm, from about 50 nm to about 130 nm, from about 60 nm to about 110 nm, or from about 70 nm to about 90 nm. To achieve further size reduction or homogeneity of size in the particles, sizing can be conducted as described above.

In other embodiments, the methods will further comprise adding non-lipid polycations which are useful to effect delivery to cells using the present compositions. Examples of suitable non-lipid polycations include, but are not limited to, hexadimethrine bromide (sold under the brand name POLYBRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine, and polyethyleneimine.

In certain embodiments, the formation of the cargo-lipid particles can be carried out either in a mono-phase system (e.g., a Bligh and Dyer monophase or similar mixture of aqueous and organic solvents) or in a two-phase system with suitable mixing.

When formation of the complexes is carried out in a mono-phase system, the cationic lipids and cargoes are each dissolved in a volume of the mono-phase mixture. Combination of the two solutions provides a single mixture in which the complexes form. Alternatively, the complexes can form in two-phase mixtures in which the cationic lipids bind to the cargo (which is present in the aqueous phase), and "pull" it into the organic phase.

In another embodiment, serum-stable cargo-lipid particles can be prepared as follows:
  (a) contacting cargoes with a solution comprising non-cationic lipids (e.g., immune response reducing lipids as described herein) and a detergent to form a cargo-lipid mixture;
  (b) contacting cationic lipids with the cargo-lipid mixture to neutralize a portion of the negative charge of the cargoes/lipids and form a charge-neutralized mixture of cargoes and lipids; and
  (c) removing the detergent from the charge-neutralized mixture to provide the cargo-lipid particles in which the cargoes are protected from degradation.

In one group of embodiments, the solution of non-cationic lipids and detergent is an aqueous solution. Contacting the cargoes with the solution of non-cationic lipids and detergent can be accomplished by mixing together a first solution of cargoes and a second solution of the lipids and detergent. One of skill in the art will understand that this mixing can take place by any number of methods, for example, by mechanical means such as by using vortex mixers. Optionally, the cargo solution is also a detergent solution. The amount of non-cationic lipid which is used in the present method can be determined based on the amount of cationic lipid used, and is typically of from about 0.2 to about 5 times the amount of cationic lipid, optionally from about 0.5 to about 2 times the amount of cationic lipid used.

In some embodiments, the cargoes are precondensed as described in, e.g., U.S. patent application Ser. No. 09/744,103.

A cargo-lipid mixture thus formed can be contacted with cationic lipids to neutralize a portion of the negative charge which is associated with the cargoes or lipids (or other polyanionic materials) present. The amount of cationic lipids used will often be sufficient to neutralize at least 50% of the negative charge of the cargo/lipids. Optionally, the negative charge will be at least 70% neutralized, or at least 90% neutralized. Cationic lipids which are useful in the present formulations, include, for example, DLinDMA and DLenDMA. These lipids and related analogs are described in U.S. Patent Publication No. 2006/0083780.

Contacting cationic lipids with a cargo-lipid formulation mixture can be accomplished by any of a number of techniques, optionally by mixing together a solution of the cationic lipid and a solution containing the cargo-lipid mixture. Upon mixing the two solutions (or contacting in any other manner), a portion of the negative charge associated with the cargo or, e.g., immune response reducing lipid, is neutralized. Nevertheless, the cargo can remain in an uncondensed state and acquire hydrophilic characteristics.

After cationic lipids have been contacted with the cargo-lipid mixture, the detergent (or combination of detergent and organic solvent) is removed, thus forming the cargo-lipid formulation particles. The methods used to remove the detergent will typically involve dialysis. When organic solvents are present, removal is typically accomplished by evaporation at reduced pressures or by blowing a stream of inert gas (e.g., nitrogen or argon) across the mixture.

The formulation particles thus formed can be sized from about 30 nm to several microns, about 50 nm to about 150 nm, from about 60 nm to about 130 nm, from about 70 nm to about 110 nm, or from about 70 nm to about 90 nm. To achieve further size reduction or homogeneity of size in the formulation particles, the cargo-lipid formulation particles can be sonicated, filtered, or subjected to other sizing techniques which are used in liposomal formulations and are known to those of skill in the art.

In other embodiments, the methods of making formulation particles of the invention can further comprise adding non-lipid polycations which are useful to effect lipofection of cells. Examples of non-lipid polycations include, hexadimethrine bromide (sold under the brandname POLYBRENE®, from Aldrich Chemical Co., Milwaukee, Wis., USA) or other salts of hexadimethrine. Other polycations include, for example, salts of poly-L-ornithine, poly-L-arginine, poly-L-lysine, poly-D-lysine, polyallylamine, and polyethyleneimine. Addition of these salts is optionally after initial formulation particles have been formed.

In one embodiment, the cargo is a DsiRNA as described herein; an immune response reducing lipid as described herein is added (e.g., as a non-cationic lipid, where appropriate); optionally, a cationic lipid of the formulation is DLindMA, DLenDMA, DODAC, DDAB, DOTMA, DOSPA, DMRIE, DOGS, or combinations thereof, and an optional non-cationic lipid is ESM, DOPE, PEG-DAG, DSPC, DPPC, DPPE, DMPE, monomethyl-phosphatidylethanolamine, dimethyl-phosphatidylethanolamine, DSPE, DEPE, SOPE, POPE, cholesterol, or combinations thereof (e.g., DSPC and PEG-DAA); and the organic solvent is methanol, chloroform, methylene chloride, ethanol, diethyl ether or combinations thereof.

In one embodiment, the cargo-lipid formulation particles prepared according to the above-described methods are either net charge neutral or carry an overall charge which provides the particles with greater gene lipofection activity (while any immune responses caused by such formulation particles are reduced or prevented by immune response reducing lipids as described herein). Optionally, the cargo component of the particles is a nucleic acid (e.g., a DsiRNA) which interferes with the production of an undesired protein.

In certain embodiments, the ability of a formulation of the invention to reduce or prevent an immune response in a subject is evaluated in the context of administering such a formulation to a population of subjects, as compared to the outcome of administration of an appropriate control formulation to a corresponding population of subjects. Regarding the immune response reducing formulations of the present invention, the probability that an immune response will be elicited by the immunogenic or immunostimulatory agent of the formulation in a subject may be decreased such that the probability is no greater than about 1%. In accordance with the formulations of the present invention the probability that an immune response will be elicited by the immunogenic or immunostimulatory agent of the formulation in a subject may be decreased such that the probability is no greater than about 5%. In accordance with the formulations of the present invention the probability that an immune response will be elicited by the immunogenic or immunostimulatory agent of the formulation in a subject may be decreased such that the probability is no greater than about 10%. In accordance with the formulations of the present invention the probability that an immune response will be elicited by the immunogenic or immunostimulatory agent of the formulation in a subject may be decreased such that the probability is no greater than about 20%. In accordance with the formulations of the present invention the probability that an immune response will be elicited by the immunogenic or immunostimulatory agent of the formulation in a subject may be decreased such that the probability is no greater than about 30%. In accordance with the formulations of the present invention the probability that an immune response will be elicited by the immunogenic or immunostimulatory agent of the formulation in a subject may be decreased such that the probability is no greater than about 40%. In accordance with the formulations of the present invention the probability that an immune response will be elicited by the immunogenic or immunostimulatory agent of the formulation in a subject may be decreased such that the probability is no greater than about 50%. In accordance with the formulations of the present invention the probability that an immune response will be elicited by the immunogenic or immunostimulatory agent of the formulation in a subject may be decreased such that the probability is no greater than about 60%. In accordance with the formulations of the present invention the probability that an immune response will be elicited by the immunogenic or immunostimulatory agent of the formulation in a subject may be decreased such that the probability is no greater than about 70%. In accordance with the formulations of the present invention the probability that an immune response will be elicited by the immunogenic or immunostimulatory agent of the formulation in a subject may be decreased such that the probability is no greater than about 80%. In accordance with the formulations of the present invention the probability that an immune response will be elicited by the immunogenic or immunostimulatory agent of the formulation in a subject may be decreased such that the probability is no greater than about 90%.

In certain embodiments, the formulation cargo (e.g., a DsiRNA of the formulation) is not substantially degraded after exposure of the formulation to a nuclease at 37° C. (or, in the case of a peptide or protein cargo, after exposure of the formulation to a peptidase at 37° C.) for at least 20, 30, 45, or 60 minutes; or after incubation of the particle in serum at 37° C. for at least 30, 45, or 60 minutes.

Formulation Cargoes

The instant invention is broadly applicable to formulations containing any of a number of cargoes/payloads—indeed, any cargo/payload capable of use in a lipidic formulation can be used as a cargo of a formulation of the instant invention. Exemplary cargoes include nucleic acid cargoes (e.g., siRNA, DsiRNA, antisense oligonucleotide) and non-nucleic acid cargoes, including proteins, small molecules, active drugs, peptide hormones, steroid hormones, and cytotoxic agents such as camptothecin, SN-38, homo-campotothecin (BN80915), paclitaxel, doxorubicin, and methotrexate.

Administration of Cargo-Lipid Formulations

Serum-stable cargo (e.g., nucleic acid)-lipid formulation particles of the present invention can be used to introduce cargoes into cells. Accordingly, the present invention also provides methods for introducing one or more cargoes into cells. The methods are carried out in vitro or in vivo by first forming the formulation particles in a manner as described above and then contacting the particles with the cells for a period of time sufficient for delivery of the one or more cargoes to occur.

Cargo-lipid formulation particles of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the cargo portion of the particle can take place via any one of these pathways. In particular, when fusion takes place, the particle membrane is integrated into the cell membrane and the contents of the particle combine with the intracellular fluid.

Cargo-lipid formulation particles of the present invention can be administered either alone or in a mixture with a pharmaceutically-acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically-acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically-acceptable" refers to molecular entities and compositions that do not produce an allergic or similar untoward reaction when administered to a human.

A pharmaceutically-acceptable carrier is generally added following particle formation. Thus, after a formulation particle is formed, the particle can be diluted into pharmaceutically-acceptable carriers such as normal buffered saline. The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment.

This may be particularly desirable in patients having atherosclerosis-associated congestive heart failure or severe hypertension. Alternatively, particles composed of irritating lipids may be diluted to low concentrations to lessen inflammation at the site of administration.

In Vivo Administration

Systemic delivery for in vivo therapy, i.e., delivery of a therapeutic cargo (e.g., nucleic acid) to a distal target cell via body systems such as the circulation, has been described for nucleic acid-lipid formulation particles such as those disclosed in PCT Publication No. WO 96/40964 and U.S. Pat. Nos. 5,705,385; 5,976,567; 5,981,501; and 6,410,328. Certain formats provide a fully encapsulated cargo-lipid formulation particle that protects the cargo or combination of cargoes from nuclease degradation in serum, is nonimmunogenic, is small in size, and is suitable for repeat dosing. Additional detail regarding administration of pharmaceutical compositions of the instant invention is provided below.

In Vitro Administration

For in vitro applications, the delivery of cargoes (e.g., nucleic acids) can be to any cell grown in culture, whether of plant or animal origin, vertebrate or invertebrate, and of any tissue or type. In certain embodiments, the cells are animal cells, e.g., mammalian cells such as human cells.

Contact between the cells and a cargo-lipid formulation particle, when carried out in vitro, takes place in a biologically compatible medium. Concentrations of particles vary widely depending on the particular application, but are generally between about 1 μmol and about 10 mmol. Treatment of the cells with the cargo-lipid formulation particles is generally carried out at physiological temperatures (about 37° C.) for periods of time of from about 1 to 48 hours, e.g., from about 2 to 4 hours.

In one group of embodiments, a cargo-lipid formulation particle suspension is added to 60-80% confluent plated cells having a cell density of from about $10^3$ to about $10^5$ cells/ml, optionally about $2 \times 10^4$ cells/ml. In certain embodiments, the concentration of the suspension added to the cells can be from about 0.01 to 0.2 μg/ml, optionally about 0.1 μg/ml.

The delivery efficiency of a lipid-based carrier system can be optimized via assay. An exemplary Endosomal Release Parameter (ERP) assay is described in detail in U.S. Patent Publication No. 2003/0077829. More particularly, the purpose of such an assay is to distinguish the effect of various cationic lipids and helper lipid components of lipid-based carrier systems (e.g., SNALPs) based on their relative effect on binding/uptake or fusion with/destabilization of the endosomal membrane. This assay allows one to determine quantitatively how each component of the lipid-based carrier system affects delivery efficiency, thereby optimizing the lipid-based carrier systems. Usually, such an assay measures expression of a reporter protein (e.g., luciferase, β-galactosidase, green fluorescent protein (GFP), etc.), and in some instances, a SNALP formulation optimized for an expression plasmid will also be appropriate for encapsulating the cargoes (e.g., nucleic acids) described herein. at least 5%, 10%, 20%, 30%, 40%, 50%, 60%, 70%, 80%, 90%, 95%, or even 100%. In other instances, such an assay can be adapted to measure downregulation of transcription or translation of a target sequence in the presence or absence of the nucleic acids described herein. By comparing the assay values (e.g., ERP values) for each of the various lipid-based formulations, one can readily determine the optimized system, e.g., the lipid-based formulation that has the greatest uptake in the cell.

Cells for Delivery of Cargoes

The compositions and methods of the present invention can be used to treat a wide variety of cell types, in vivo and in vitro. Suitable cells include, e.g., hematopoietic precursor (stem) cells, fibroblasts, keratinocytes, hepatocytes, endothelial cells, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like.

In vivo delivery of cargo-lipid formulation particles of the present invention is suited for targeting cells of any cell type. The methods and compositions can be employed with cells of a wide variety of vertebrates, including mammals, such as, e.g., canines, felines, equines, bovines, ovines, caprines, rodents (e.g., mice, rats, and guinea pigs), lagomorphs, swine, and primates (e.g. monkeys, chimpanzees, and humans).

To the extent that tissue culture of cells may be required, it is well-known in the art. For example, Freshney, Culture of Animal Cells, a Manual of Basic Technique, 3rd Ed., Wiley-Liss, New York (1994), Kuchler et al, Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Detection of Lipidic Formulations

In some embodiments, the cargo-lipid formulation particles are detectable in the subject at about 8, 12, 24, 48, 60, 72, or 96 hours, or 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles; detection of the modified cargo (e.g., nucleic acid); where the cargo is a nucleic acid, detection of a nucleic acid that silences expression of a target sequence; detection of the target and/or target sequence of interest (i.e., by detecting expression or reduced expression of the target and/or sequence of interest), or a combination thereof. A cargo-lipid formulation comprising an immune response reducing lipid, when compared to a control formulation, results in at least 5%, 10%, 20%, 30%, 40%, 50%, 60%, 70%, 80%, 90%, 95%, or even 100% increase in the detection of cargo-lipid formulation particles, as measured by a detection method, e.g., fluorescent tag or PCR.

Detection of Particles

Cargo-lipid formulation particles can be detected using any methods known in the art. For example, a label can be coupled directly or indirectly to a component of the carrier system using methods well-known in the art. A wide variety of labels can be used, with the choice of label depending on sensitivity required, ease of conjugation with the carrier system component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horseradish peroxidase, alkaline phosphatase, etc.; spectral colorimetric labels such as colloidal gold or colored glass or plastic beads such as polystyrene, polypropylene, latex, etc. The label can be detected using any means known in the art.

Detection of Cargoes

Cargoes can be detected and quantified herein by any of a number of means well-known to those of skill in the art. The detection of peptide and/or protein cargoes can be achieved, e.g., by antibody-based methods, such as ELISA, immunoprecipitation and Western analysis. The detection of nucleic acids proceeds by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed for a cargo of a formulation of the invention.

For nucleic acid cargoes, the selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

Sensitivity of a hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA™) are found in Sambrook et al, In Molecular Cloning: A Laboratory Manual, Cold Spring Harbor Laboratory Press (2000); and Ausubel et al, SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), C&EN 36; The Journal Of NIH Research, 3:81 (1991); Kwoh et al., Proc. Natl. Acad. ScL USA, 86:1173 (1989); Guatelli et al., Proc. Natl. Acad. Sci. USA, 87: 1874 (1990); Lomell et al., J. Clin. Chem., 35: 1826 (1989); Landegren et al, Science, 241:1077 (1988); Van Brunt, Biotechnology, 8:291 (1990); Wu and Wallace, Gene, 4:560 (1989); Barringer et al, Gene, 89: 117 (1990); and Sooknanan and Malek, Biotechnology, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Nucleic acids for use as probes, e.g., in in vitro amplification methods, for use as gene probes, or as inhibitor components are typically synthesized chemically according to the solid phase phosphoramidite triester method described by Beaucage et al, Tetrahedron Letts., 22: 1859 1862 (1981), e.g., using an automated synthesizer, as described in Needham VanDevanter et al, Nucleic Acids Res., 12:6159 (1984). Purification of polynucleotides, where necessary, is typically performed by either native acrylamide gel electrophoresis or by anion exchange HPLC as described in Pearson et al, J. Chrom., 255: 137 149 (1983). The sequence of the synthetic polynucleotides can be verified using the chemical degradation method of Maxam and Gilbert (1980) in Grossman and Moldave (eds.) Academic Press, New York, Methods in Enzymology, 65:499.

An alternative means for determining the level of transcription of a nucleic acid/gene (e.g., target gene) is in situ hybridization. In situ hybridization assays are well-known and are generally described in Angerer et al., *Methods Enzymol,* 152: 649. In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are optionally labeled with radioisotopes or fluorescent reporters.

Detection of Immunogenic and/or Immunostimulatory Effects of a Cargo-Lipid Formulation Assessment of the immunogenic and/or immunostimulatory effects of a cargo-lipid formulation can be performed via any art-recognized method. For example, for an immunogenic or immunostimulatory cargo or other immunogenic or immunostimulatory component of a formulation of the invention, detection of an immune response may be performed at the molecular level in a cell, tissue or organism/subject, e.g., via detection of TLR levels and/or levels of downstream signaling targets/cytokines such as interferon (e.g., interferon alpha), detection of antibodies directed against formulation components, e.g., via ELISA or other assay, etc. A cargo-lipid formulation comprising an immune response reducing lipid, when compared to a control formulation, results in at least 5%, 10%, 20%, 30%, 40%, 50%, 60%, 70%, 80%, 90%, 95%, or even 100% decrease in immunogenic and/or immunostimulatory effects, as measured by ELISA or other assay for immunogenic and/or immunostimulatory effects.

Phenotypes associated with an immune response can also be assessed to determine the extent to which an immune response occurs in a cell, tissue or organism/subject—for example, fatigue, flu-like symptoms (e.g., fever, chills, sweats), diarrhea, reduced bone marrow function, infection, rash, hypotension, arrhythmia, elevated liver enzymes, complement activation, splenomegaly, enlarged lymph nodes, erythema, fainting, anemia and/or bleeding problems (e.g., prolonged coagulation) might be assessed as a means for determining whether and/or the extent to which an administered formulation of the invention is causing an immune response in a subject. The range and forms of measurement that can be implemented to assess immune response of a cell, tissue or subject to a formulation of the instant invention will be clear to one of skill in the art.

Delivery of Formulations and Conjugation of Cargoes

In certain embodiments, the present invention relates to a method for treating a subject having or at risk of developing a disease or disorder. In such embodiments, a formulation of the invention can act as a novel therapeutic agent for controlling the disease or disorder. Where the formulation comprises a DsiRNA cargo, the method comprises administering a pharmaceutical composition of the invention to the patient (e.g., human), such that the expression, level and/or activity of a target RNA is reduced. The expression, level and/or activity of a polypeptide encoded by the target RNA might also be reduced by a DsiRNA of such formulations of the instant invention.

In the treatment of a disease or disorder, a formulation can be brought into contact with the cells or tissue exhibiting or associated with a disease or disorder. For example, a formulation comprising a DsiRNA substantially identical to all or part of a target RNA sequence, may be brought into contact with or introduced into a diseased, disease-associated or infected cell, either in vivo or in vitro. Similarly, a DsiRNA cargo substantially identical to all or part of a target RNA sequence may administered directly to a subject having or at risk of developing a disease or disorder.

Therapeutic use of formulations of the instant invention can involve use of formulations comprising multiple different cargoes. For example, two or more, three or more, four or more, five or more, etc. of the presently described cargoes (e.g., DsiRNAs) can be combined to produce a formulation that, e.g., targets multiple different regions of one or more target RNA(s). For DsiRNA formulations, a DsiRNA cargo may also be constructed such that either strand of the DsiRNA independently targets two or more regions of a target RNA. Use of multifunctional DsiRNA molecules that target more then one region of a target nucleic acid molecule is expected to provide potent inhibition of RNA levels and expression. For example, a single multifunctional DsiRNA cargo can target both conserved and variable regions of a target nucleic acid molecule, thereby allowing down regulation or inhibition of, e.g., different strain variants of a virus, or splice variants encoded by a single target gene.

For certain formulations of the invention, a cargo can be conjugated (e.g., for a DsiRNA cargo, at its 5' or 3' terminus of its sense or antisense strand) or otherwise formulated with another moiety (e.g. for a nucleic acid cargo, a non-nucleic acid moiety such as a peptide can also be formulated), e.g., an organic compound (e.g., a dye, cholesterol, or the like). Modifying cargoes in this way may improve cellular uptake or enhance cellular targeting activities of the cargo and/or derivatives thereof, as compared to a corresponding unconjugated cargo, are useful for tracing cargoes and/or their derivatives in the organism/cell, and/or can improve the stability of a cargo and/or its derivative, as compared to a corresponding unconjugated cargo.

A cargo-lipid formulation comprising an immune response reducing lipid, when compared to a control formulation, results in at least 5%, 10%, 20%, 30%, 40%, 50%, 60%, 70%, 80%, 90%, 95%, or even 100% increase in the detection of cargo in cargo-lipid formulation particles, as measured by a detection method, e.g., fluorescent tag or PCR.

Exemplary Structures of dsRNA Cargoes

In certain aspects, the present invention provides formulations for RNA interference (RNAi) that include a DsiRNA cargo.

Double-stranded RNA (dsRNA) agents possessing strand lengths of 25 to 35 nucleotides have been described as effective inhibitors of target gene expression in mammalian cells (Rossi et al., U.S. Patent Publication Nos. 2005/0244858 and 2005/0277610). dsRNA agents of such length are believed to be processed by the Dicer enzyme of the RNA interference (RNAi) pathway, leading such agents to be termed "Dicer substrate siRNA" ("DsiRNA") agents. Certain modified structures of DsiRNA agents were previously described (Rossi et al., U.S. Patent Publication No. 2007/0265220). Additional DsiRNA structures and specific compositions suitable for use in the formulations of the instant invention are described in U.S. patent application Ser. Nos. 12/642,371; 12/586,283; 61/257,810; 61/257,820; 12/586,281; 61/183,815; 61/183,818; 61/183,815; 61/184,735; 61/285,925; 61/151,841; 61/361,759; 61,361,776; 61/435,304; 12/824,011; PCT/US2010/60102; PCT/US2010/037263; and PCT/US2010/037265.

In one such embodiment, the DsiRNA comprises:

```
5'-pXXXXXXXXXXXXXXXXXXXXXXXXX-3'
3'-YXXXXXXXXXXXXXXXXXXXXXXXXXp-5'
``` wherein "X"=RNA, "p"=a phosphate group and "Y" is an overhang domain comprised of 1-4 RNA monomers that are optionally 2'-O-methyl RNA monomers.

In one embodiment, a DsiRNA cargo of a formulation of the invention comprises:

```
5'-pXXXXXXXXXXXXXXXXXXXXXXXDD-3'
3'-YXXXXXXXXXXXXXXXXXXXXXXXXXp-5'
``` wherein "X"=RNA, "p"=a phosphate group, "Y" is an overhang domain comprised of 1-4 RNA monomers that are optionally 2'-O-methyl RNA monomers, and "D"=DNA. In one embodiment, the top strand is the sense strand, and the bottom strand is the antisense strand. Alternatively, the bottom strand is the sense strand and the top strand is the antisense strand.

In an additional embodiment, the DsiRNA comprises:

```
5'-pXXXXXXXXXXXXXXXXXXXXXXXXX-3'
3'-YXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers.

In a related embodiment, the DsiRNA comprises:

```
5'-pXXXXXXXXXXXXXXXXXXXXXXXDD-3'
3'-YXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand.

In another embodiment, the DsiRNA comprises:

```
5'-pXXXXXXXXXXXXXXXXXXXXXXXXX-3'
3'-YXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers.

In a related embodiment, the DsiRNA comprises:

```
5'-pXXXXXXXXXXXXXXXXXXXXXXXDD-3'
3'-YXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand.

In another embodiment, the DsiRNA comprises:

```
5'-pXXXXXXXXXXXXXXXXXXXXXXXXX-3'
3'-YXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers.

In a related embodiment, the DsiRNA comprises:

```
5'-pXXXXXXXXXXXXXXXXXXXXXXXDD-3'
3'-YXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand.

In further embodiments, the DsiRNA comprises:

```
5'-pXXXXXXXXXXXXXXXXXXXXXXXXX-3'
3'-YXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

```
5'-pXXXXXXXXXXXXXXXXXXXXXXXDD-3'
3'-YXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

```
5'-pXXXXXXXXXXXXXXXXXXXXXXXXX-3'
3'-XXXXXXXXXXXXXXXXXXXXXXXXXXp-5'
``` wherein "X"=RNA, "p"=a phosphate group and "X"=2'-O-methyl RNA. In a further related embodiment, the DsiRNA comprises:

```
5'-pXXXXXXXXXXXXXXXXXXXXXXXDD-3'
3'-XXXXXXXXXXXXXXXXXXXXXXXXXXp-5'
``` wherein "X"=RNA, "p"=a phosphate group, "X"=2'-O-methyl RNA, and "D"=DNA. The top strand is the sense strand, and the bottom strand is the antisense strand.

In additional embodiments, the DsiRNA comprises:

```
5'-pXXXXXXXXXXXXXXXXXXXXXXXXX-3'
3'-YXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

```
5'-pXXXXXXXXXXXXXXXXXXXXXXXDD-3'
3'-YXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. The top strand is the sense strand, and the bottom strand is the antisense strand. In another related embodiment, the DsiRNA comprises:

```
5'-pXXXXXXXXXXXXXXXXXXXXXXXXX- 3'
3'-XXXXXXXXXXXXXXXXXXXXXXXXXXp-5'
``` wherein "X"=RNA, "p"=a phosphate group and "X"=2'-O-methyl RNA. The top strand is the sense strand, and the bottom strand is the antisense strand. In a further related embodiment, the DsiRNA comprises:

```
5'-pXXXXXXXXXXXXXXXXXXXXXXXDD-3'
3'-XXXXXXXXXXXXXXXXXXXXXXXXXXp-5'
``` wherein "X"=RNA, "p"=a phosphate group, "X"=2'-O-methyl RNA, and "D"=DNA. The top strand is the sense strand, and the bottom strand is the antisense strand.

In other embodiments, the DsiRNA comprises:

```
5'-pXXXXXXXXXXXXXXXXXXXXXXXXX-3'
3'-YXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-pXXXXXXXXXXXXXXXXXXXXXXXDD-3'
3'-YXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

```
5'-pXXXXXXXXXXXXXXXXXXXXXXXXX-   3'

3'-XXXXXXXXXXXXXXXXXXXXXXXXXXXp-5'
``` wherein "X"=RNA, "p"=a phosphate group and "X"=2'-O-methyl RNA. The top strand is the sense strand, and the bottom strand is the antisense strand. In another related embodiment, the DsiRNA comprises:

```
5'-pXXXXXXXXXXXXXXXXXXXXXXXDD-3'

3'-XXXXXXXXXXXXXXXXXXXXXXXXXXXp-5'
``` wherein "X"=RNA, "p"=a phosphate group, "X"=2'-O-methyl RNA, and "D"=DNA. The top strand is the sense strand, and the bottom strand is the antisense strand.

In further embodiments, the DsiRNA comprises:

```
5'-pXXXXXXXXXXXXXXXXXXXXXXXXX-3'

3'-YXXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-pXXXXXXXXXXXXXXXXXXXXXXXDD-3'

3'-YXXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

```
5'-pXXXXXXXXXXXXXXXXXXXXXXXXX-3'

3'-XXXXXXXXXXXXXXXXXXXXXXXXXXXp-5'
``` wherein "X"=RNA, "p"=a phosphate group and "X"=2'-O-methyl RNA. The top strand is the sense strand, and the bottom strand is the antisense strand. In a further related embodiment, the DsiRNA comprises:

```
5'-pXXXXXXXXXXXXXXXXXXXXXXXDD-3'

3'-XXXXXXXXXXXXXXXXXXXXXXXXXXXp-5'
``` wherein "X"=RNA, "p"=a phosphate group, "X"=2'-O-methyl RNA, and "D"=DNA. The top strand is the sense strand, and the bottom strand is the antisense strand.

In additional embodiments, the DsiRNA comprises:

```
5'-pXXXXXXXXXXXXXXXXXXXXXXXXX-3'

3'-YXXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-pXXXXXXXXXXXXXXXXXXXXXXXDD-3'

3'-YXXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-pXXXXXXXXXXXXXXXXXXXXXXXXX-3'

3'-XXXXXXXXXXXXXXXXXXXXXXXXXXXp-5'
``` wherein "X"=RNA, "p"=a phosphate group and "X"=2'-O-methyl RNA. The top strand is the sense strand, and the bottom strand is the antisense strand. In a further related embodiment, the DsiRNA comprises:

```
5'-pXXXXXXXXXXXXXXXXXXXXXXXDD-3'

3'-XXXXXXXXXXXXXXXXXXXXXXXXXXXp-5'
``` wherein "X"=RNA, "p"=a phosphate group, "X"=2'-O-methyl RNA, and "D"=DNA. The top strand is the sense strand, and the bottom strand is the antisense strand.

In other embodiments, the DsiRNA comprises:

```
5'-pXXXXXXXXXXXXXXXXXXXXXXXXX-3'

3'-YXXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-pXXXXXXXXXXXXXXXXXXXXXXXDD-3'

3'-YXXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-pXXXXXXXXXXXXXXXXXXXXXXXXX-3'

3'-XXXXXXXXXXXXXXXXXXXXXXXXXXXp-5'
``` wherein "X"=RNA, "p"=a phosphate group and "X"=2'-O-methyl RNA. The top strand is the sense strand, and the bottom strand is the antisense strand. In a further related embodiment, the DsiRNA comprises:

```
5'-pXXXXXXXXXXXXXXXXXXXXXXXDD-3'
3'-XXXXXXXXXXXXXXXXXXXXXXXXXXXp-5'
``` wherein "X"=RNA, "p"=a phosphate group, "X"=2'-O-methyl RNA, and "D"=DNA. The top strand is the sense strand, and the bottom strand is the antisense strand.

In additional embodiments, the DsiRNA comprises:

```
5'-pXXXXXXXXXXXXXXXXXXXXXXXX-3'
3'-YXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-pXXXXXXXXXXXXXXXXXXXXXXXDD-3'
3'-YXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-pXXXXXXXXXXXXXXXXXXXXXXXX-3'
3'-XXXXXXXXXXXXXXXXXXXXXXXXXp-5'
``` wherein "X"=RNA, "p"=a phosphate group and "X"=2'-O-methyl RNA. The top strand is the sense strand, and the bottom strand is the antisense strand. In a further related embodiment, the DsiRNA comprises:

```
5'-pXXXXXXXXXXXXXXXXXXXXXXXDD-3'
3'-XXXXXXXXXXXXXXXXXXXXXXXXXXXp-5'
``` wherein "X"=RNA, "p"=a phosphate group, "X"=2'-O-methyl RNA, and "D"=DNA. The top strand is the sense strand, and the bottom strand is the antisense strand.

In further embodiments, the DsiRNA comprises:

```
5'-pXXXXXXXXXXXXXXXXXXXXXXXX-3'
3'-YXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-pXXXXXXXXXXXXXXXXXXXXXXXDD-3'
3'-YXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-pXXXXXXXXXXXXXXXXXXXXXXXX-3'
3'-XXXXXXXXXXXXXXXXXXXXXXXXXp-5'
``` wherein "X"=RNA, "p"=a phosphate group and "X"=2'-O-methyl RNA. The top strand is the sense strand, and the bottom strand is the antisense strand. In a further related embodiment, the DsiRNA comprises:

```
5'-pXXXXXXXXXXXXXXXXXXXXXXXDD-3'
3'-XXXXXXXXXXXXXXXXXXXXXXXXXXXp-5'
``` wherein "X"=RNA, "p"=a phosphate group, "X"=2'-O-methyl RNA, and "D"=DNA. The top strand is the sense strand, and the bottom strand is the antisense strand.

In additional embodiments, the DsiRNA comprises:

```
5'-pXXXXXXXXXXXXXXXXXXXXXXXX-3'
3'-YXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-pXXXXXXXXXXXXXXXXXXXXXXXDD-3'
3'-YXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-pXXXXXXXXXXXXXXXXXXXXXXXX-3'
3'-XXXXXXXXXXXXXXXXXXXXXXXXXp-5'
``` wherein "X"=RNA, "p"=a phosphate group and "X"=2'-O-methyl RNA. The top strand is the sense strand, and the bottom strand is the antisense strand. In a further related embodiment, the DsiRNA comprises:

```
5'-pXXXXXXXXXXXXXXXXXXXXXXXDD-3'
3'-XXXXXXXXXXXXXXXXXXXXXXXXXXXp-5'
``` wherein "X"=RNA, "p"=a phosphate group, "X̱"=2'-O-methyl RNA, and "D"=DNA. The top strand is the sense strand, and the bottom strand is the antisense strand.

In other embodiments, the DsiRNA comprises:

```
5'-pXXXXXXXXXXXXXXXXXXXXXXXXX-3'
3'-YXX̱X̱X̱XXXXXXXXXXXX̱X̱XXXXXXXXXXp-5'
``` wherein "X"=RNA, "p"=a phosphate group, "X̱"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-pXXXXXXXXXXXXXXXXXXXXXXXDD-3'
3'-YXX̱X̱X̱XXXXXXXXXXXX̱X̱XXXXXXXXXXp-5'
``` wherein "X"=RNA, "p"=a phosphate group, "X̱"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-pXXXXXXXXXXXXXXXXXXXXXXXXX-3'
3'-X̱XXX̱X̱X̱XXXXXXXXXXXX̱X̱XXXXXXXXXXp-5'
``` wherein "X"=RNA, "p"=a phosphate group and "X̱"=2'-O-methyl RNA. The top strand is the sense strand, and the bottom strand is the antisense strand. In a further related embodiment, the DsiRNA comprises:

```
5'-pXXXXXXXXXXXXXXXXXXXXXXXDD-3'
3'-X̱XXX̱X̱X̱XXXXXXXXXXXX̱X̱XXXXXXXXXXp-5'
``` wherein "X"=RNA, "p"=a phosphate group, "X̱"=2'-O-methyl RNA, and "D"=DNA. The top strand is the sense strand, and the bottom strand is the antisense strand.

In further embodiments, the DsiRNA comprises:

```
5'-pXXXXXXXXXXXXXXXXXXXXXXXXX-3'
3'-YXXXXXXXXXXXXXXX̱X̱XXXXXXXXXXp-5'
``` wherein "X"=RNA, "p"=a phosphate group, "X̱"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-pXXXXXXXXXXXXXXXXXXXXXXXDD-3'
3'-YXXXXXXXXXXXXXXX̱X̱XXXXXXXXXXp-5'
``` wherein "X"=RNA, "p"=a phosphate group, "X̱"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-pXXXXXXXXXXXXXXXXXXXXXXXXX-3'
3'-X̱XXXXXXXXXXXXXXX̱X̱XXXXXXXXXXp-5'
``` wherein "X"=RNA, "p"=a phosphate group and "X̱"=2'-O-methyl RNA. The top strand is the sense strand, and the bottom strand is the antisense strand. In a further related embodiment, the DsiRNA comprises:

```
5'-pXXXXXXXXXXXXXXXXXXXXXXXDD-3'
3'-X̱XXXXXXXXXXXXXXX̱X̱XXXXXXXXXXp-5'
``` wherein "X"=RNA, "p"=a phosphate group, "X̱"=2'-O-methyl RNA, and "D"=DNA. The top strand is the sense strand, and the bottom strand is the antisense strand.

In additional embodiments, the DsiRNA comprises:

```
5'-pXXXXXXXXXXXXXXXXXXXXXXXXX-3'
3'-YX̱XXXXXXXXXXXXXX̱X̱XXXXXXXXXXp-5'
``` wherein "X"=RNA, "p"=a phosphate group, "X̱"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-pXXXXXXXXXXXXXXXXXXXXXXXDD-3'
3'-YX̱XXXXXXXXXXXXXX̱X̱XXXXXXXXXXp-5'
``` wherein "X"=RNA, "p"=a phosphate group, "X̱"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-pXXXXXXXXXXXXXXXXXXXXXXXXX-3'
3'-X̱XXX̱XXXXXXXXXXXX̱X̱XXXXXXXXXXp-5'
``` wherein "X"=RNA, "p"=a phosphate group and "X̱"=2'-O-methyl RNA. The top strand is the sense strand, and the bottom strand is the antisense strand. In a further related embodiment, the DsiRNA comprises:

```
5'-pXXXXXXXXXXXXXXXXXXXXXXXDD-3'
3'-X̱XXX̱XXXXXXXXXXXX̱X̱XXXXXXXXXXp-5'
``` wherein "X"=RNA, "p"=a phosphate group, "X̱"=2'-O-methyl RNA, and "D"=DNA. The top strand is the sense strand, and the bottom strand is the antisense strand.

In further embodiments, the DsiRNA comprises:

```
5'-pXXXXXXXXXXXXXXXXXXXXXXXXX-3'
3'-YXX̱XXXXXXXXXXXX̱X̱XXXXXXXXXXXp-5'
``` wherein "X"=RNA, "p"=a phosphate group, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-pXXXXXXXXXXXXXXXXXXXXXXXDD-3'

3'-YX̲XX̲XXXXXXXXXXX̲XX̲XXXXXXXXX̲X̲p-5' wherein "X"=RNA, "p"=a phosphate group, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-pXXXXXXXXXXXXXXXXXXXXXXXXX-3'

3'-X̲XXX̲XXXXXXXXXXX̲XXXXXXXXXXX̲X̲p-5' wherein "X"=RNA, "p"=a phosphate group and "X̲"=2'-O-methyl RNA. The top strand is the sense strand, and the bottom strand is the antisense strand. In a further related embodiment, the DsiRNA comprises:

5'-pXXXXXXXXXXXXXXXXXXXXXXXDD-3'

3'-X̲XXX̲XXXXXXXXXXX̲XXXXXXXXXX̲X̲p-5' wherein "X"=RNA, "p"=a phosphate group, "X̲"=2'-O-methyl RNA, and "D"=DNA. The top strand is the sense strand, and the bottom strand is the antisense strand.

In other embodiments, the DsiRNA comprises:

5'-pXXXXXXXXXXXXXXXXXXXXXXXXX-3'

3'-YX̲XXXXXXXXXXX̲XX̲XXXXXXXXXXX̲X̲p-5' wherein "X"=RNA, "p"=a phosphate group, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In another related embodiment, the DsiRNA comprises:

5'-pXXXXXXXXXXXXXXXXXXXXXXXDD-3'

3'-YX̲XXXXXXXXXXX̲XXXXXXXXXX̲X̲X̲p-5' wherein "X"=RNA, "p"=a phosphate group, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-pXXXXXXXXXXXXXXXXXXXXXXXXX-3'

3'-X̲XXX̲XXXXXXXXXXX̲XXXXXXXXXX̲X̲X̲p-5' wherein "X"=RNA, "p"=a phosphate group and "X̲"=2'-O-methyl RNA. The top strand is the sense strand, and the bottom strand is the antisense strand. In a further related embodiment, the DsiRNA comprises:

5'-pXXXXXXXXXXXXXXXXXXXXXXXDD-3'

3'-XXXXXXXXXXXXXXX̲XXXXXXXXXXXX̲p-5' wherein "X"=RNA, "p"=a phosphate group, "X̲"=2'-O-methyl RNA, and "D"=DNA. The top strand is the sense strand, and the bottom strand is the antisense strand.

In further embodiments, the DsiRNA comprises:

5'-pXXXXXXXXXXXXXXXXXXXXXXXXX-3'

3'-YX̲XX̲XXXXXXXXXXX̲XXXXXXXXXXX̲X̲p-5' wherein "X"=RNA, "p"=a phosphate group, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-pXXXXXXXXXXXXXXXXXXXXXXXDD-3'

3'-YX̲XX̲XXXXXXXXXX̲XXXXXXXXXX̲X̲p-5' wherein "X"=RNA, "p"=a phosphate group, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-pXXXXXXXXXXXXXXXXXXXXXXXXX-3'

3'-X̲XXX̲XXXXXXXXXXX̲XXXXXXXXXXXX̲p-5' wherein "X"=RNA, "p"=a phosphate group and "X̲"=2'-O-methyl RNA. The top strand is the sense strand, and the bottom strand is the antisense strand. In a further related embodiment, the DsiRNA comprises:

5'-pXXXXXXXXXXXXXXXXXXXXXXXDD-3'

3'-X̲XXX̲XXXX̲XXXXXXX̲XXXXXXXXXX̲X̲p-5' wherein "X"=RNA, "p"=a phosphate group, "X̲"=2'-O-methyl RNA, and "D"=DNA. The top strand is the sense strand, and the bottom strand is the antisense strand.

In additional embodiments, the DsiRNA comprises:

5'-pXXXXXXXXXXXXXXXXXXXXXXXXX-3'

3'-YXXXXXXXXXXXXXX̲XXXXXXXXXXX̲X̲p-5' wherein "X"=RNA, "p"=a phosphate group, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-pXXXXXXXXXXXXXXXXXXXXXXXXXDD-3'
3'-YXXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-pXXXXXXXXXXXXXXXXXXXXXXXXX- 3'
3'-XXXXXXXXXXXXXXXXXXXXXXXXXXXp-5'
``` wherein "X"=RNA, "p"=a phosphate group and "X"=2'-O-methyl RNA. The top strand is the sense strand, and the bottom strand is the antisense strand. In a further related embodiment, the DsiRNA comprises:

```
5'-pXXXXXXXXXXXXXXXXXXXXXXXXXDD-3'
3'-XXXXXXXXXXXXXXXXXXXXXXXXXXXp-5'
``` wherein "X"=RNA, "p"=a phosphate group, "X"=2'-O-methyl RNA, and "D"=DNA. The top strand is the sense strand, and the bottom strand is the antisense strand.

In further embodiments, the DsiRNA comprises:

```
5'-pXXXXXXXXXXXXXXXXXXXXXXXXX-3'
3'-YXXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-pXXXXXXXXXXXXXXXXXXXXXXXXXDD-3'
3'-YXXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-pXXXXXXXXXXXXXXXXXXXXXXXXX-3'
3'-XXXXXXXXXXXXXXXXXXXXXXXXXXXp-5'
``` wherein "X"=RNA, "p"=a phosphate group and "X"=2'-O-methyl RNA. The top strand is the sense strand, and the bottom strand is the antisense strand. In a further related embodiment, the DsiRNA comprises:

```
5'-pXXXXXXXXXXXXXXXXXXXXXXXXXDD-3'
3'-XXXXXXXXXXXXXXXXXXXXXXXXXXXp-5'
``` wherein "X"=RNA, "p"=a phosphate group, "X"=2'-O-methyl RNA, and "D"=DNA. The top strand is the sense strand, and the bottom strand is the antisense strand.

In additional embodiments, the DsiRNA comprises:

```
5'-pXXXXXXXXXXXXXXXXXXXXXXXXX-3'
3'-YXXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-pXXXXXXXXXXXXXXXXXXXXXXXXXDD-3'
3'-YXXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-pXXXXXXXXXXXXXXXXXXXXXXXXX- 3'
3'-XXXXXXXXXXXXXXXXXXXXXXXXXXXp-5'
``` wherein "X"=RNA, "p"=a phosphate group and "X"=2'-O-methyl RNA. The top strand is the sense strand, and the bottom strand is the antisense strand. In a further related embodiment, the DsiRNA comprises:

```
5'-pXXXXXXXXXXXXXXXXXXXXXXXXXDD-3'
3'-XXXXXXXXXXXXXXXXXXXXXXXXXXXp-5'
``` wherein "X"=RNA, "p"=a phosphate group, "X"=2'-O-methyl RNA, and "D"=DNA. The top strand is the sense strand, and the bottom strand is the antisense strand.

In further embodiments, the DsiRNA comprises:

```
5'-pXXXXXXXXXXXXXXXXXXXXXXXXX-3'
3'-YXXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-pXXXXXXXXXXXXXXXXXXXXXXXXXDD-3'
3'-YXXXXXXXXXXXXXXXXXXXXXXXXXXXp-5'
``` wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

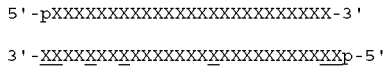

wherein "X"=RNA, "p"=a phosphate group and "X"=2'-O-methyl RNA. The top strand is the sense strand, and the bottom strand is the antisense strand. In a further related embodiment, the DsiRNA comprises:

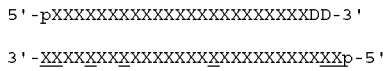

wherein "X"=RNA, "p"=a phosphate group, "X"=2'-O-methyl RNA, and "D"=DNA. The top strand is the sense strand, and the bottom strand is the antisense strand.

In additional embodiments, the DsiRNA comprises:

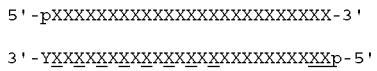

wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

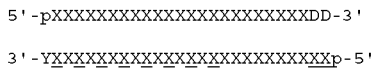

wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

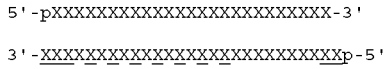

wherein "X"=RNA, "p"=a phosphate group and "X"=2'-O-methyl RNA. The top strand is the sense strand, and the bottom strand is the antisense strand. In a further related embodiment, the DsiRNA comprises:

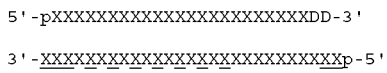

wherein "X"=RNA, "p"=a phosphate group, "X"=2'-O-methyl RNA, and "D"=DNA. The top strand is the sense strand, and the bottom strand is the antisense strand.

In further embodiments, the DsiRNA comprises:

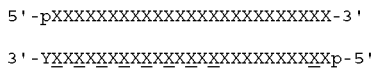

wherein "X"=RNA, "p"=a phosphate group, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

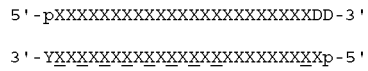

wherein "X"=RNA, "p"=a phosphate group, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

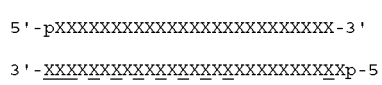

wherein "X"=RNA, "p"=a phosphate group and "X"=2'-O-methyl RNA. The top strand is the sense strand, and the bottom strand is the antisense strand. In a further related embodiment, the DsiRNA comprises:

wherein "X"=RNA, "p"=a phosphate group, "X"=2'-O-methyl RNA, and "D"=DNA. The top strand is the sense strand, and the bottom strand is the antisense strand.

The above modification patterns can also be incorporated into, e.g., the extended DsiRNA structures and mismatch and/or frayed DsiRNA structures described below.

In another embodiment, the DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary 27mer DsiRNA agent with two terminal mismatched residues is shown:

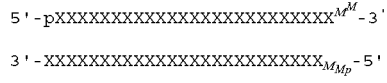

wherein "X"=RNA, "p"=a phosphate group, "M"=Nucleic acid residues (RNA, DNA or non-natural or modified nucleic acids) that do not base pair (hydrogen bond) with corresponding "M" residues of otherwise complementary strand when strands are annealed. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand is the sense strand, and the bottom strand is the antisense strand. Alternatively, the bottom strand is the sense strand and the top strand is the antisense strand.

In certain, the present invention provides formulations for RNA interference (RNAi) where a dsNA cargo possesses one or more base paired deoxyribonucleotides within a region of a double stranded nucleic acid (dsNA) that is positioned 3' of a projected sense strand Dicer cleavage site and correspondingly 5' of a projected antisense strand Dicer cleavage site. Such formulations of the invention comprise a dsNA which is a precursor molecule, i.e., the dsNA of a formulation of the present invention is processed in vivo to produce an active small interfering nucleic acid (siRNA). The dsNA is processed by Dicer to an active siRNA which is incorporated into RISC.

In certain embodiments, DsiRNA agents of the formulations of the invention can have any of the following exemplary structures:

In one embodiment, the DsiRNA comprises:

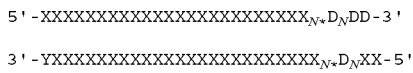

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-15 or, optionally, 1-8. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In a related embodiment, the DsiRNA comprises:

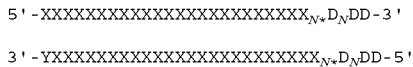

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-15 or, optionally, 1-8. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In an additional embodiment, the DsiRNA comprises:

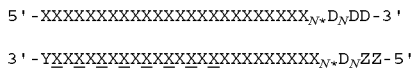

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-15 or, optionally, 1-8. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

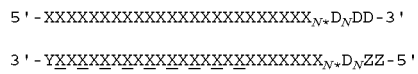

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-15 or, optionally, 1-8. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

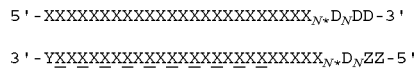

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-15 or, optionally, 1-8. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DsiRNA comprises:

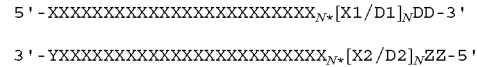

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-15 or, optionally, 1-8, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In any of the above-depicted structures, the 5' end of either the sense strand or antisense strand optionally comprises a phosphate group.

In another embodiment, a DNA:DNA-extended DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary DNA:DNA-extended DsiRNA agent with two terminal mismatched residues is shown:

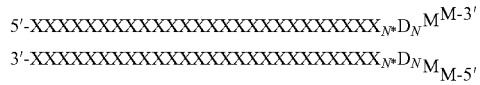

wherein "X"=RNA, "M"=Nucleic acid residues (RNA, DNA or non-natural or modified nucleic acids) that do not base pair (hydrogen bond) with corresponding "M" residues of otherwise complementary strand when strands are annealed, "D"=DNA and "N"=1 to 50 or more, but is optionally 1-15 or, optionally, 1-8. "N*"=0 to 15 or more, but is optionally 0, 1, 2, 3, 4, 5 or 6. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand (first strand) is the sense strand, and the bottom strand (second strand) is the antisense strand. Alternatively, the bottom strand is the sense strand and the top strand is the antisense strand. Modification and DNA:DNA extension patterns paralleling those shown above for asymmetric/overhang agents can also be incorporated into such "blunt/frayed" agents.

In one embodiment, a length-extended DsiRNA agent is provided that comprises deoxyribonucleotides positioned at sites modeled to function via specific direction of Dicer cleavage, yet which does not require the presence of a base-paired deoxyribonucleotide in the dsNA structure. An exemplary structure for such a molecule is shown:

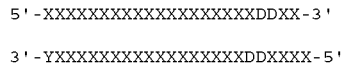

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "D"=DNA. In one embodiment, the top strand is the sense strand, and the bottom strand is the antisense strand. Alternatively, the bottom strand is the sense strand and the top strand is the antisense strand. The above structure is modeled to force Dicer to cleave a minimum of a 21mer duplex as its primary post-processing form. In embodiments where the bottom strand of the above structure is the antisense strand, the positioning of two deoxyribonucleotide residues at the ultimate and penultimate residues of the 5' end of the antisense strand is likely to reduce off-target effects (as prior studies have shown a 2'-O-methyl modification of at least the penultimate position from the 5' terminus of the antisense strand to reduce off-target effects; see, e.g., US 2007/0223427).

In one embodiment, the DsiRNA comprises:

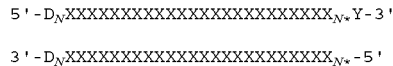

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-15 or, optionally, 1-8. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In a related embodiment, the DsiRNA comprises:

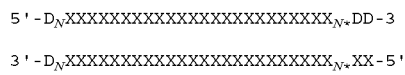

wherein "X"=RNA, optionally a 2'-O-methyl RNA monomers "D"=DNA, "N"=1 to 50 or more, but is optionally 1-15 or, optionally, 1-8. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In an additional embodiment, the DsiRNA comprises:

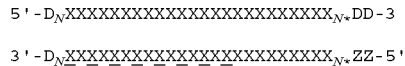

wherein "X"=RNA, optionally a 2'-O-methyl RNA monomers "D"=DNA, "N"=1 to 50 or more, but is optionally 1-15 or, optionally, 1-8. "N*"=0 to 15 or more, but is optionally 0, 1, 2, 3, 4, 5 or 6. "Z"=DNA or RNA. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

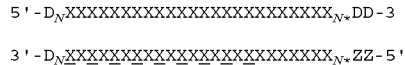

wherein "X"=RNA, optionally a 2'-O-methyl RNA monomers "D"=DNA, "N"=1 to 50 or more, but is optionally 1-15 or, optionally, 1-8. "N*"=0 to 15 or more, but is optionally 0, 1, 2, 3, 4, 5 or 6. "Z"=DNA or RNA. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

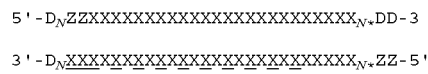

wherein "X"=RNA, "X"=2'-O-methyl RNA, "D"=DNA, "Z"=DNA or RNA, and "N"=1 to 50 or more, but is optionally 1-15 or, optionally, 1-8. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

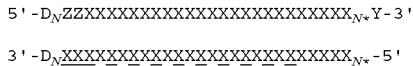

wherein "X"=RNA, "X"=2'-O-methyl RNA, "D"=DNA, "Z"=DNA or RNA, and "N"=1 to 50 or more, but is optionally 1-15 or, optionally, 1-8. "N*"=0 to 15 or more, but is optionally 0, 1, 2, 3, 4, 5 or 6. "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DsiRNA comprises:

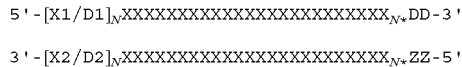

wherein "X"=RNA, "D"=DNA, "Z"=DNA or RNA, and "N"=1 to 50 or more, but is optionally 1-15 or, optionally, 1-8, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In a related embodiment, the DsiRNA comprises:

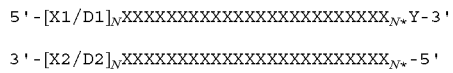

wherein "X"=RNA, "D"=DNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "N"=1 to 50 or more, but is optionally 1-15 or, optionally, 1-8, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In any of the above-depicted structures, the 5' end of either the sense strand or antisense strand optionally comprises a phosphate group.

In another embodiment, a DNA:DNA-extended DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary DNA:DNA-extended DsiRNA agent with two terminal mismatched residues is shown:

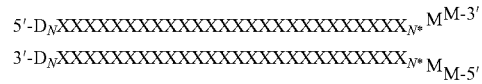

wherein "X"=RNA, "M"=Nucleic acid residues (RNA, DNA or non-natural or modified nucleic acids) that do not base pair (hydrogen bond) with corresponding "M" residues of otherwise complementary strand when strands are annealed, "D"=DNA and "N"=1 to 50 or more, but is optionally 1-15 or, optionally, 1-8. "N*"=0 to 15 or more, but is optionally 0, 1, 2, 3, 4, 5 or 6. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand (first strand) is the sense strand, and the bottom strand (second strand) is the antisense strand. Alternatively, the bottom strand is the sense strand and the top strand is the antisense strand. Modification and DNA:DNA extension patterns paralleling those shown above for asymmetric/overhang agents can also be incorporated into such "blunt/frayed" agents.

In another embodiment, a length-extended DsiRNA agent is provided that comprises deoxyribonucleotides positioned at sites modeled to function via specific direction of Dicer cleavage, yet which does not require the presence of a base-paired deoxyribonucleotide in the dsNA structure. Exemplary structures for such a molecule are shown:

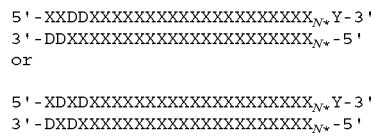

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "D"=DNA. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand. The above structures are modeled to force Dicer to cleave a minimum of a 21mer duplex as its primary post-processing form.

In any of the above embodiments where the bottom strand of the above structure is the antisense strand, the positioning of two deoxyribonucleotide residues at the ultimate and penultimate residues of the 5' end of the antisense strand is likely to reduce off-target effects (as prior studies have shown a 2'-O-methyl modification of at least the penultimate position from the 5' terminus of the antisense strand to reduce off-target effects; see, e.g., US 2007/0223427).

DsiRNAs of the formulations of the invention can carry a broad range of modification patterns (e.g., 2'-O-methyl RNA patterns, e.g., within extended DsiRNA agents). Certain modification patterns of the second strand of DsiRNAs of the formulations of the invention are presented below.

DsiRNA Cargo Design/Synthesis

It was previously shown that longer dsRNA species of from 25 to about 30 nucleotides (DsiRNAs) yield unexpectedly effective RNA inhibitory results in terms of potency and duration of action, as compared to 19-23mer siRNA agents. Without wishing to be bound by the underlying theory of the dsRNA processing mechanism, it is thought that the longer dsRNA species serve as a substrate for the Dicer enzyme in the cytoplasm of a cell. In addition to cleaving dsNA such as the DsiRNA cargoes of the invention into shorter segments, Dicer is thought to facilitate the incorporation of a single-stranded cleavage product derived from the cleaved dsNA into the RISC complex that is responsible for the destruction of the cytoplasmic RNA of or derived from the target gene. Prior studies (Rossi et al., U.S. Patent Application No. 2007/0265220) have shown that the cleavability of a dsRNA species (specifically, a DsiRNA agent) by Dicer corresponds with increased potency and duration of action of the dsRNA species. The instant invention, at least in part, provides for design of RNA inhibitory agents that direct the site of Dicer cleavage, such that certain species of Dicer cleavage products are thereby generated.

In DsiRNA processing, Dicer enzyme binds to a DsiRNA agent, resulting in cleavage of the DsiRNA at a position 19-23 nucleotides removed from a Dicer PAZ domain-associated 3' overhang sequence of the antisense strand of the DsiRNA agent. This Dicer cleavage event results in excision of those duplexed nucleic acids previously located at the 3' end of the passenger (sense) strand and 5' end of the guide (antisense) strand. (Cleavage of a DsiRNA typically yields a 19mer duplex with 2-base overhangs at each end.) This Dicer cleavage event can generate a 21-23 nucleotide guide (antisense) strand capable of directing sequence-specific inhibition of target mRNA as a RISC component.

The first and second oligonucleotides of the DsiRNA cargoes of the instant invention are not required to be completely complementary. For example, the 3'-terminus of the sense strand can contain one or more mismatches. Optionally, about two mismatches are incorporated at the 3' terminus of the sense strand. A DsiRNA cargo of the invention can also be a double stranded RNA molecule containing two RNA oligonucleotides, each of which is an identical number of nucleotides in the range of 27-35 nucleotides in length and, when annealed to each other, have blunt ends and a two nucleotide mismatch on the 3'-terminus of the sense strand (the 5'-terminus of the antisense strand). The use of mismatches or decreased thermodynamic stability (specifically at the 3'-sense/5'-antisense position) has been proposed to facilitate or favor entry of the antisense strand into RISC (Schwarz et al., 2003; Khvorova et al., 2003), presumably by affecting some rate-limiting unwinding steps that occur with entry of the siRNA into RISC. Thus, terminal base composition has been included in design algorithms for selecting active 21mer siRNA duplexes (Ui-Tei et al., 2004; Reynolds et al., 2004). With Dicer cleavage of the dsRNA region of certain DsiRNA cargoes, a small end-terminal sequence which contains mismatches will either be left unpaired with the antisense strand (become part of a 3'-overhang) or be cleaved entirely off the final 21-mer siRNA. Such specific forms of "mismatches", therefore, do not persist as mismatches in the final RNA component of RISC. The finding that base mismatches or destabilization of segments at the 3'-end of the sense strand of Dicer substrate improved the potency of synthetic duplexes in RNAi, presumably by facilitating processing by Dicer, was a surprising finding of past works describing the design and use of 25-30mer dsRNAs (also termed "DsiRNAs" herein; Rossi et al., U.S. Patent Application Nos. 2005/0277610, 2005/0244858 and 2007/0265220). It was also surprising to find that DsiRNAs having base-paired deoxyribonucleotides at either passenger (sense) or guide (antisense) strand positions that are predicted to be 3' of the most 3' Dicer cleavage site of the respective passenger or guide strand are at least equally effective as RNA-RNA duplex-extended DsiRNA cargoes. Such agents may also harbor mismatches, with such mismatches being formed by the antisense strand either in reference to (actual or projected hybridization with) the sequence of the sense strand of the DsiRNA cargo, or in reference to the target RNA sequence. Exemplary mismatched or wobble base pairs of cargoes possessing mismatches are G:A, C:A, C:U, G:G, A:A, C:C, U:U, I:A, I:U and I:C. Base pair strength of such cargoes can also be lessened via modification of the nucleotides of such cargoes, including, e.g., 2-amino- or 2,6-diamino modifications of guanine and adenine nucleotides.

Modification of DsiRNA Cargoes

In certain aspects, the instant invention provides formulations comprising a dsRNA cargo. One major factor that inhibits the effect of double stranded RNAs ("dsRNAs") is the degradation of dsRNAs (e.g., siRNAs and DsiRNAs) by nucleases. A 3'-exonuclease is the primary nuclease activity present in serum and modification of the 3'-ends of antisense DNA oligonucleotides is crucial to prevent degradation (Eder et al., 1991). An RNase-T family nuclease has been identified called ERI-1 which has 3' to 5' exonuclease activity that is involved in regulation and degradation of siRNAs (Kennedy et al., 2004; Hong et al., 2005). This gene is also known as Thex1 (NM_02067) in mice or THEX1 (NM_153332) in humans and is involved in degradation of histone mRNA; it also mediates degradation of 3'-overhangs in siRNAs, but does not degrade duplex RNA (Yang et al., 2006). It is therefore reasonable to expect that 3'-end-stabilization of dsRNAs, including, e.g., DsiRNAs of certain formulations of the instant invention, will improve stability.

XRN1 (NM_019001) is a 5' to 3' exonuclease that resides in P-bodies and has been implicated in degradation of mRNA targeted by miRNA (Rehwinkel et al., 2005) and may also be responsible for completing degradation initiated by internal cleavage as directed by a siRNA. XRN2 (NM_012255) is a distinct 5' to 3' exonuclease that is involved in nuclear RNA processing. Although not currently implicated in degradation or processing of siRNAs and miRNAs, these both are known nucleases that can degrade RNAs and may also be important to consider.

RNase A is a major endonuclease activity in mammals that degrades RNAs. It is specific for ssRNA and cleaves at the 3'-end of pyrimidine bases. siRNA degradation products consistent with RNase A cleavage can be detected by mass spectrometry after incubation in serum (Turner et al., 2007). The 3'-overhangs enhance the susceptibility of siRNAs to RNase degradation. Depletion of RNase A from serum reduces degradation of siRNAs; this degradation does show some sequence preference and is worse for sequences having poly A/U sequence on the ends (Haupenthal et al., 2006). This suggests the possibility that lower stability regions of the duplex may "breathe" and offer transient single-stranded species available for degradation by RNase A. RNase A inhibitors can be added to serum and improve siRNA longevity and potency (Haupenthal et al., 2007).

In 21mers, phosphorothioate or boranophosphate modifications directly stabilize the internucleoside phosphate linkage. Boranophosphate modified RNAs are highly nuclease resistant, potent as silencing agents, and are relatively non-toxic. Boranophosphate modified RNAs cannot be manufactured using standard chemical synthesis methods and instead are made by in vitro transcription (IVT) (Hall et al., 2004 and Hall et al., 2006). Phosphorothioate (PS) modifications can be readily placed in an RNA duplex at any desired position and can be made using standard chemical synthesis methods, though the ability to use such modifications within an RNA duplex that retains RNA silencing activity can be limited. Inclusion of a multiple PS-modified deoxyribonucleotide residues in a tandem series configuration that base paired with a cognate tandem series of PS-modified deoxyribonucleotide residues abolished RNA silencing activity of an agent that was otherwise active with only unmodified deoxyribonucleotides present at these residues. Because PS moieties are likely to require greater spacing when included within an RNA duplex-containing agent in order to retain RNA inhibitory activity, extended DsiRNAs can provide a means of including more PS modifications (either PS-DNA or PS-RNA) within a single DsiRNA cargo than would otherwise be available were no such extension used. It is noted, however, that the PS modification shows dose-dependent toxicity, so most investigators have recommended limited incorporation in siRNAs, historically favoring the 3'-ends where protection from nucleases is most important (Harborth et al., 2003; Chiu and Rana, 2003; Braasch et al., 2003; Amarzguioui et al., 2003). More extensive PS modification can be compatible with potent RNAi activity; however, use of sugar modifications (such as 2'-O-methyl RNA) may be superior (Choung et al., 2006).

A variety of substitutions can be placed at the 2'-position of the ribose which generally increases duplex stability ($T_m$) and can greatly improve nuclease resistance. 2'-O-methyl RNA is a naturally occurring modification found in mammalian ribosomal RNAs and transfer RNAs. 2'-O-methyl modification in siRNAs is known, but the precise position of modified bases within the duplex is important to retain potency and complete substitution of 2'-O-methyl RNA for RNA will inactivate the siRNA. For example, a pattern that employs alternating 2'-O-methyl bases can have potency equivalent to unmodified RNA and is quite stable in serum (Choung et al., 2006; Czauderna et al., 2003).

The 2'-fluoro (2'-F) modification is also compatible with dsRNA (e.g., siRNA and DsiRNA) function; it is most commonly placed at pyrimidine sites (due to reagent cost and availability) and can be combined with 2'-O-methyl modification at purine positions; 2'-F purines are available and can also be used. Heavily modified duplexes of this kind can be potent triggers of RNAi in vitro (Allerson et al., 2005; Prakash et al., 2005; Kraynack and Baker, 2006) and can improve performance and extend duration of action when used in vivo (Morrissey et al., 2005a; Morrissey et al., 2005b). A highly potent, nuclease stable, blunt 19mer duplex containing alternative 2'-F and 2'-O-Me bases is taught by Allerson. In this design, alternating 2'-O-Me residues are positioned in an identical pattern to that employed by Czauderna, however the remaining RNA residues are converted to 2'-F modified bases. A highly potent, nuclease resistant siRNA employed by Morrissey employed a highly potent, nuclease resistant siRNA in vivo. In addition to 2'-O-Me RNA and 2'-F RNA, this duplex includes DNA, RNA, inverted abasic residues, and a 3'-terminal PS internucleoside linkage. While extensive modification has certain benefits, more limited modification of the duplex can also improve in vivo performance and is both simpler and less costly to manufacture. Soutschek et al. (2004) employed a duplex in vivo and was mostly RNA with two 2'-O-Me RNA bases and limited 3'-terminal PS internucleoside linkages.

Locked nucleic acids (LNAs) are a different class of 2'-modification that can be used to stabilize dsRNA (e.g., siRNA and DsiRNA). Patterns of LNA incorporation that retain potency are more restricted than 2'-O-methyl or 2'-F bases, so limited modification is preferred (Braasch et al., 2003; Grunweller et al., 2003; Elmen et al., 2005). Even with limited incorporation, the use of LNA modifications can improve dsRNA performance in vivo and may also alter or improve off target effect profiles (Mook et al., 2007).

Synthetic nucleic acids introduced into cells or live animals can be recognized as "foreign" and trigger an immune response. Immune stimulation constitutes a major class of off-target effects which can dramatically change experimental results and even lead to cell death. The innate immune system includes a collection of receptor molecules that specifically interact with DNA and RNA that mediate these responses, some of which are located in the cytoplasm and some of which reside in endosomes (Marques and Williams, 2005; Schlee et al., 2006). Delivery of siRNAs by cationic lipids or liposomes exposes the siRNA to both cytoplasmic and endosomal compartments, maximizing the risk for triggering a type 1 interferon (IFN) response both in vitro and in vivo (Morrissey et al., 2005b; Sioud and Sorensen, 2003; Sioud, 2005; Ma et al., 2005). RNAs transcribed within the cell are less immunogenic (Robbins et al., 2006) and synthetic RNAs that are immunogenic when delivered using lipid-based methods can evade immune stimulation when introduced unto cells by mechanical means, even in vivo (Heidel et al., 2004). However, lipid based delivery methods are convenient, effective, and widely used. A general strategy to prevent immune responses, such as the one described herein, is needed, especially for in vivo application where all cell types are present and the risk of generating an immune response is highest. Use of chemically modified RNAs may also aid in solving such immune response problems.

Although certain sequence motifs are clearly more immunogenic than others, it appears that the receptors of the innate immune system in general distinguish the presence or absence of certain base modifications which are more commonly found in mammalian RNAs than in prokaryotic RNAs. For example, pseudouridine, N6-methyl-A, and 2'-O-methyl modified bases are recognized as "self" and inclusion of these residues in a synthetic RNA can help evade immune detection (Kariko et al., 2005). Extensive 2'-modification of a sequence that is strongly immunostimulatory as unmodified RNA can block an immune response when administered to mice intravenously (Morrissey et al., 2005b). However, extensive modification is not needed to escape immune detection and substitution of as few as two 2'-O-methyl bases in a single strand of a siRNA duplex can be sufficient to block a type 1 IFN response both in vitro and in vivo; modified U and G bases are most effective (Judge et al., 2006). As an added benefit, selective incorporation of 2'-O-methyl bases can reduce the magnitude of off-target effects (Jackson et al., 2006). Use of 2'-O-methyl bases should therefore be considered for all dsRNAs intended for in vivo applications as a means of blocking immune responses and has the added benefit of improving nuclease stability and reducing the likelihood of off-target effects.

Although cell death can result from immune stimulation, assessing cell viability is not an adequate method to monitor induction of IFN responses. IFN responses can be present without cell death, and cell death can result from target knockdown in the absence of IFN triggering (for example, if the targeted gene is essential for cell viability). Relevant cytokines can be directly measured in culture medium and a variety of commercial kits exist which make performing such assays routine. While a large number of different immune effector molecules can be measured, testing levels of IFN-α, TNF-α, and IL-6 at 30 minutes to one hour and/or 4 and 24 hours post-transfection can suffice for screening purposes. It is important to include a "transfection reagent only control" as cationic lipids can trigger immune responses in certain cells in the absence of any nucleic acid cargo. Including controls for IFN pathway induction should be considered for cell culture work. It is essential to test for immune stimulation whenever administering nucleic acids in vivo, where the risk of triggering IFN responses is highest.

Modifications can be included in the DsiRNA cargoes of certain formulations of the present invention so long as the modification does not prevent the DsiRNA cargo from serving as a substrate for Dicer. It was previously found that base paired deoxyribonucleotides can be attached to DsiRNA molecules, resulting in enhanced RNAi efficacy and duration, provided that such extension is performed in a region of the extended molecule that does not interfere with Dicer processing (e.g., 3' of the Dicer cleavage site of the sense strand/5' of the Dicer cleavage site of the antisense strand). In one embodiment, one or more modifications are made that enhance Dicer processing of the DsiRNA cargo. In a second embodiment, one or more modifications are made that result in more effective RNAi generation. In a third embodiment, one or more modifications are made that support a greater RNAi effect. In a fourth embodiment, one or more modifications are made that result in greater potency per each DsiRNA cargo molecule to be delivered to the cell. Modifications can be incorporated in the 3'-terminal region, the 5'-terminal region, in both the 3'-terminal and 5'-terminal region or in some instances in various positions within the sequence. With the restrictions noted above in mind, any number and combination of modifications can be incorporated into the DsiRNA cargo. Where multiple modifications are present, they may be the same or different. Modifications to bases, sugar moieties, the phosphate backbone, and their combinations are contemplated. Either 5'-terminus can be phosphorylated.

Examples of modifications contemplated for the phosphate backbone include phosphonates, including methylphosphonate, phosphorothioate, and phosphotriester modifications such as alkylphosphotriesters, and the like. Examples of modifications contemplated for the sugar moiety include 2'-alkyl pyrimidine, such as 2'-O-methyl, 2'-fluoro, amino, and deoxy modifications and the like (see, e.g., Amarzguioui et al., 2003). Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like. Locked nucleic acids, or LNA's, could also be incorporated. Many other modifications are known and can be used so long as the above criteria are satisfied. Examples of modifications are also disclosed in U.S. Pat. Nos. 5,684,143, 5,858,988 and 6,291,438 and in U.S. published patent application No. 2004/0203145 A1. Other modifications are disclosed in Herdewijn (2000), Eckstein (2000), Rusckowski et al. (2000), Stein et al. (2001); Vorobjev et al. (2001).

One or more modifications contemplated can be incorporated into either strand. The placement of the modifications in the DsiRNA cargo can greatly affect the characteristics of the DsiRNA cargo, including conferring greater potency and stability, reducing toxicity, enhancing Dicer processing, and minimizing an immune response. In one embodiment, the antisense strand or the sense strand or both strands have one or more 2'-O-methyl modified nucleotides. In another embodiment, the antisense strand contains 2'-O-methyl modified nucleotides. In another embodiment, the antisense stand contains a 3' overhang that is comprised of 2'-O-methyl modified nucleotides. The antisense strand could also include additional 2'-O-methyl modified nucleotides.

In certain embodiments of the formulations of the present invention, a DsiRNA cargo has one or more properties which enhance its processing by Dicer. According to these embodiments, the DsiRNA has a length sufficient such that it is processed by Dicer to produce an active siRNA and at least one of the following properties: (i) the DsiRNA is asymmetric, e.g., has a 3' overhang on the antisense strand and (ii) the DsiRNA has a modified 3' end on the sense strand to direct orientation of Dicer binding and processing of the dsRNA region to an active siRNA. In certain such embodiments, the presence of one or more base paired deoxyribonucleotides in a region of the sense strand that is 3' to the projected site of Dicer enzyme cleavage and corresponding region of the antisense strand that is 5' of the projected site of Dicer enzyme cleavage can also serve to orient such a molecule for appropriate directionality of Dicer enzyme cleavage.

The length of a dsDNA region (or length of the region comprising DNA:DNA base pairs) of an "extended" DsiRNA can be 1-50 base pairs, optionally 2-30 base pairs, optionally 2-20 base pairs, and optionally 2-15 base pairs. Thus, a DNA:DNA-extended DsiRNA of certain formulations of the instant invention may possess a dsDNA region that is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more (e.g., 51, 52, 53, 54, 55, 56, 57, 58, 59, 60 or more) base pairs in length. In some embodiments, the longest strand in the dsNA comprises 29-43 nucleotides. In one embodiment, a DsiRNA cargo is asymmetric such that the 3' end of the sense strand and 5' end of the antisense strand form a blunt end, and the 3' end of the antisense strand overhangs the 5' end of the sense strand. In certain embodiments, the 3' overhang of the antisense strand is 1-10 nucleotides, and optionally is 1-4 nucleotides, for example 2 nucleotides. Both the sense and the antisense strand may also have a 5' phosphate. In certain embodiments, the sense strand of a DsiRNA of a formulation of the invention that comprises base paired deoxyribonucleotide residues has a total length of between 26 nucleotides and 39 or more nucleotides (e.g., the sense strand possesses a length of 26, 27, 28, 29, 30, 31, 32, 33, 34, 35, 36, 37, 38, 39, 40, 41, 42, 43, 44, 45, 46, 47, 48, 49, 50 or more (e.g., 51, 52, 53, 54, 55, 56, 57, 58, 59, 60 or more) nucleotides). In certain embodiments, the length of the sense strand is between 26 nucleotides and 39 nucleotides, optionally between 27 and 35 nucleotides, or, optionally, between 27 and 33 nucleotides in length. In related embodiments, the antisense strand has a length of between 27 and 43 or more nucleotides (e.g., the sense strand possesses a length of 26, 27, 28, 29, 30, 31, 32, 33, 34, 35, 36, 37, 38, 39, 40, 41, 42, 43, 44, 45, 46, 47, 48, 49, 50 or more (e.g., 51, 52, 53, 54, 55, 56, 57, 58, 59, 60 or more) nucleotides). In certain such embodiments, the antisense strand has a length of between 27 and 43 nucleotides in length, or between 27 and 39 nucleotides in length, or between 27 and 35 nucleotides in length, or between 28 and 37 nucleotides in length, or, optionally, between 29 and 35 nucleotides in length.

In certain embodiments, the sense strand of a DsiRNA cargo is modified for Dicer processing by suitable modifiers located at the 3' end of the sense strand, i.e., the DsiRNA cargo is designed to direct orientation of Dicer binding and processing via sense strand modification. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxyribonucleotides are used as the modifiers. When nucleotide modifiers are utilized, 1-3 nucleotide modifiers, or 2 nucleotide modifiers are substituted for the ribonucleotides on the 3' end of the sense strand. When sterically hindered molecules are utilized, they are attached to the ribonucleotide at the 3' end of the antisense strand. Thus, the length of the strand does not change with the incorporation of the modifiers. For example, a DsiRNA cargo can be substituted with two DNA bases to direct the orientation of Dicer processing of the antisense strand. Optionally, two terminal DNA bases are substituted for two ribonucleotides on the 3'-end of the sense strand forming a blunt end of the duplex on the 3' end of the sense strand and the 5' end of the antisense strand, and a two-nucleotide RNA overhang is located on the 3'-end of the antisense strand. This is an asymmetric composition with DNA on the blunt end and RNA bases on the overhanging end. Optionally, the modified nucleotides (e.g., deoxyribonucleotides) of the penultimate and ultimate positions of the 3' terminus of the sense strand base pair with corresponding modified nucleotides (e.g., deoxyribonucleotides) of the antisense strand (optionally, the penultimate and ultimate residues of the 5' end of the antisense strand in those DsiRNA cargoes of the instant invention possessing a blunt end at the 3' terminus of the sense strand/5' terminus of the antisense strand).

The sense and antisense strands of a DsiRNA cargo of the instant invention anneal under biological conditions, such as the conditions found in the cytoplasm of a cell. In addition, a region of one of the sequences, particularly of the antisense strand, of the DsiRNA cargo has a sequence length of at least 19 nucleotides, wherein these nucleotides are in the 21-nucleotide region adjacent to the 3' end of the antisense strand and are sufficiently complementary to a nucleotide sequence of the RNA produced from the target gene to anneal with and/or decrease levels of such a target RNA.

The first and second oligonucleotides of a DsiRNA cargo of the instant invention are not required to be completely complementary. They only need to be substantially complementary to anneal under biological conditions and to provide a substrate for Dicer that produces a siRNA sufficiently complementary to the target sequence. Locked nucleic acids, or LNA's, are well known to a skilled artisan (Elman et al., 2005; Kurreck et al., 2002; Crinelli et al., 2002; Braasch and Corey, 2001; Bondensgaard et al., 2000; Wahlestedt et al., 2000). In one embodiment, an LNA is incorporated at the 5' terminus of the sense strand. In another embodiment, an LNA is incorporated at the 5' terminus of the sense strand in duplexes designed to include a 3' overhang on the antisense strand.

Certain DsiRNA cargoes containing two separate oligonucleotides can be linked by a third structure. The third structure will not block Dicer activity on the DsiRNA and will not interfere with the directed destruction of the RNA transcribed from the target gene. In one embodiment, the third structure may be a chemical linking group. Many suitable chemical linking groups are known in the art and can be used. Alternatively, the third structure may be an oligonucleotide that links the two oligonucleotides of the DsiRNA cargo in a manner such that a hairpin structure is produced upon annealing of the two oligonucleotides making up the dsNA composition. The hairpin structure will not block Dicer activity on the DsiRNA cargo and will not interfere with the directed destruction of the target RNA.

In certain embodiments, the DsiRNA cargo of the invention has several properties which enhance its processing by Dicer. According to such embodiments, the DsiRNA cargo has a length sufficient such that it is processed by Dicer to produce an siRNA and at least one of the following properties: (i) the DsiRNA cargo is asymmetric, e.g., has a 3' overhang on the sense strand and (ii) the DsiRNA cargo has a modified 3' end on the antisense strand to direct orientation of Dicer binding and processing of the dsRNA region to an active siRNA. According to these embodiments, the longest strand in the DsiRNA cargo comprises 25-43 nucleotides. In one embodiment, the sense strand comprises 25-39 nucleotides and the antisense strand comprises 26-43 nucleotides. The resulting dsNA can have an overhang on the 3' end of the sense strand. The overhang is 1-4 nucleotides, such as 2 nucleotides. The antisense or sense strand may also have a 5' phosphate.

In certain embodiments, the sense strand of a DsiRNA cargo is modified for Dicer processing by suitable modifiers located at the 3' end of the sense strand, i.e., the DsiRNA cargo is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxyribonucleotides are used as the modifiers. When nucleotide modifiers are utilized, 1-3 nucleotide modifiers, or 2 nucleotide modifiers are substituted for the ribonucleotides on the 3' end of the sense strand. When sterically hindered molecules are utilized, they are attached to the ribonucleotide at the 3' end of the antisense strand. Thus, the length of the strand does not change with the incorporation of the modifiers.

In certain other embodiments, the antisense strand of a DsiRNA cargo is modified for Dicer processing by suitable modifiers located at the 3' end of the antisense strand, i.e., the DsiRNA is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxyribonucleotides are used as the modifiers. When nucleotide modifiers are utilized, 1-3 nucleotide modifiers, or 2 nucleotide modifiers are substituted for the ribonucleotides on the 3' end of the antisense strand. When sterically hindered molecules are utilized, they are attached to the ribonucleotide at the 3' end of the antisense strand. Thus, the length of the strand does not change with the incorporation of the modifiers. In certain nucleic acid formulations, two DNA bases in the dsNA are substituted to direct the orientation of Dicer processing. Optionally, two terminal DNA bases are located on the 3' end of the antisense strand in place of two ribonucleotides forming a blunt end of the duplex on the 5' end of the sense strand and the 3' end of the antisense strand, and a two-nucleotide RNA overhang is located on the 3'-end of the sense strand. This is also an asymmetric composition with DNA on the blunt end and RNA bases on the overhanging end.

The sense and antisense strands anneal under biological conditions, such as the conditions found in the cytoplasm of a cell. In addition, a region of one of the sequences, particularly of the antisense strand, of the dsNA cargo has a sequence length of at least 19 nucleotides, wherein these nucleotides are adjacent to the 3' end of antisense strand and are sufficiently complementary to a nucleotide sequence of the target RNA to direct RNA interference.

US 2007/0265220 discloses that 27mer DsiRNAs show improved stability in serum over comparable 21mer siRNA compositions, even absent chemical modification. Modifications of DsiRNA cargoes, such as inclusion of 2'-O-methyl RNA in the antisense strand, in patterns such as detailed in US 2007/0265220, when coupled with addition of a 5' Phosphate, can improve stability of DsiRNA cargoes. Addition of 5'-phosphate to all strands in synthetic RNA duplexes may be an inexpensive and physiological method to confer some limited degree of nuclease stability.

The chemical modification patterns of the DsiRNA cargoes of the invention are designed to enhance the efficacy of such cargoes. Accordingly, such modifications are designed to avoid reducing potency of DsiRNA cargoes; to avoid interfering with Dicer processing of DsiRNA cargoes; to improve stability in biological fluids (reduce nuclease sensitivity) of DsiRNA cargoes; or to block or evade detection by the innate immune system. Such modifications are also designed to avoid being toxic and to avoid increasing the cost or impact the ease of manufacturing the instant DsiRNA cargoes of the invention.

Pharmaceutical Compositions

In certain embodiments, the present invention provides for a pharmaceutical composition comprising an immune response reducing formulation of the present invention. An immune response reducing formulation can be suitably formulated and introduced into the environment of the cell by any means that allows for a sufficient portion of the immune response reducing formulation to enter the cell to deliver a cargo/payload (e.g., for DsiRNA cargoes, to induce gene silencing, if it is to occur). Many formulations are known in the art and can be used so long as the immune response reducing formulation gains entry to the target cells so that it can act. See, e.g., U.S. published patent application Nos. 2004/0203145 A1 and 2005/0054598 A1. For example, the immune response reducing formulation of the instant invention can be further formulated in buffer solutions such as phosphate buffered saline solutions and capsids. Cationic lipids, such as lipofectin (U.S. Pat. No. 5,705,188), cationic glycerol derivatives, and polycationic molecules, such as polylysine (published PCT International Application WO 97/30731), can be used within the formulations of the instant invention. Optionally, Oligofectamine, Lipofectamine (Life Technologies), NC388 (Ribozyme Pharmaceuticals, Inc., Boulder, Colo.), or FuGene 6 (Roche) may be employed, all of which can be used according to the manufacturer's instructions.

Such compositions can include the lipidic formulation and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Administration can be in any manner known in the art, e.g., by injection, oral administration, inhalation (e.g., intranasal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular cargo delivery has also been discussed in Straubringer et al., *Methods Enzymol.*, 101: 512; Mannino et al, *Biotechniques*, 6: 682; Nicolau et al., Crit. Rev. Ther. Drug Carrier Syst., 6:239 (1989); and Behr, *Ace. Chem. Res.*, 26: 274. Still other methods of administering lipid-based therapeutics are described in, for example, U.S. Pat. Nos. 3,993,754; 4,145,410; 4,235,871; 4,224,179; 4,522,803; and 4,588,578. The lipid-cargo formulation particles can be administered by direct injection at the site of disease or by injection at a site distal from the site of disease (see, e.g., Culver, HUMAN GENE THERAPY, MaryAnn Liebert, Inc., Publishers, New York. pp. 70-71). The formulations of the present invention, either alone or in combination with other suitable components, can be made into aerosols (i.e., they can be "nebulized") to be administered via inhalation (e.g., intranasally or intratracheally; see, Brigham et al., *Am. J. Sci.*, 298: 278).

Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) is also well-known in the pharmaceutical arts. Similarly, transmucosal drug delivery in the form of a polytetrafluoroethylene support matrix is described in U.S. Pat. No. 5,780,045.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, formulations can be administered, for example, by intravenous infusion, orally, topically, intraperitoneally, intravesically, or intrathecally.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, optional methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Typically, oral formulations may contain at least about 0.1% of the cargo (e.g., nucleic acid)-lipid formulation particles or more, although the percentage of the particles may, of course, be varied and may conveniently be between about 1% or 2% and about 60% or 70% or more of the weight or volume of the total formulation. For formulation particles of the invention, the amount of particles in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For administration by inhalation, the formulations are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active formulations are formulated into ointments, salves, gels, or creams as generally known in the art.

The formulations can also be prepared in the form of suppositories (e.g., with conventional suppository bases such as cocoa butter and other glycerides) or retention enemas for rectal delivery.

The formulations can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

In certain embodiments, the formulations can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In certain aspects, the formulations are prepared with carriers that will protect the formulations against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Formulations suitable for oral administration can consist of, e.g.: (a) liquid solutions, such as an effective amount of the packaged cargo (e.g., nucleic acid) suspended in diluents such as water, saline, or PEG 400; (b) capsules, sachets, or tablets, each containing a predetermined amount of the cargo, as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the cargo in a flavor, e.g., sucrose, as well as pastilles comprising the cargo in an inert base, such as gelatin and glycerin or sucrose and acacia emulsions, gels, and the like containing, in addition to the cargo, carriers known in the art.

In another example of their use, cargo-lipid formulation particles can be incorporated into a broad range of topical dosage forms. For instance, a suspension containing cargo-lipid formulation particles of the invention can be formulated and administered as a gel, oil, emulsion, topical cream, paste, ointment, lotion, foam, mousse, and the like.

When preparing pharmaceutical preparations of the cargo-lipid formulation particles of the invention, it can be preferred to use quantities of the particles which have been purified to reduce or eliminate empty particles or particles with cargo (e.g., nucleic acid) associated with the external surface.

The methods of the present invention may be practiced in a variety of hosts. Exemplary hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of cargo (e.g., nucleic acid) to lipid, the particular cargo used, the disease state being diagnosed, the age, weight, and condition of the patient, and the judgment of the clinician, but will generally be between about 0.01 and about 50 mg per kilogram of body weight, optionally between about 0.1 and about 5 mg/kg of body weight, or about $10^6$-$10^{10}$ formulation particles per administration (e.g., injection).

Toxicity and therapeutic efficacy of such formulations can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Formulations which exhibit high therapeutic indices can be preferred. While formulations that exhibit toxic side effects may be used, care should be taken to design a delivery system that targets such formulations to the site of affected tissue in order to minimize potential damage to uninfected cells and, thereby, reduce side effects.

The data obtained from the cell culture assays and animal studies can be used in formulating a range of dosage for use in humans. The dosage of such formulations optionally lies within a range of circulating concentrations that include the $ED_{50}$ with little or no toxicity. The dosage may vary within this range depending upon the dosage form employed and the route of administration utilized. For any formulation used in a method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of formulation (i.e., an effective dosage) depends on the formulation selected. For instance, if a DsiRNA formulation is selected, single dose amounts (of either the formulation as a whole or of a cargo component of such formulation) in the range of approximately 1 pg to 1000 mg may be administered; in some embodiments, 10, 30, 100, or 1000 pg, or 10, 30, 100, or 1000 ng, or 10, 30, 100, or 1000 µg, or 10, 30, 100, or 1000 mg may be administered. In some embodiments, 1-5 g of the formulations can be administered. The formulations can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, nucleic acid or antibody can include a single treatment or, optionally, can include a series of treatments.

It can be appreciated that the method of introducing formulations into the environment of the cell will depend on the type of cell and the make up of its environment. For example, when the cells are found within a liquid, one optional formulation is with a lipid formulation such as in lipofectamine and the formulations can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering peptides, proteins and nucleic acids (e.g., oligonucleotides) are known and can be used. For suitable methods of introducing dsNA (e.g., DsiRNA agents), see U.S. published patent application No. 2004/0203145 A1.

Suitable amounts of a formulation must be introduced and these amounts can be empirically determined using standard methods. Typically, effective concentrations of individual formulations, or of individual cargoes of a formulation, in the environment of a cell will be about 50 nanomolar or less, 10 nanomolar or less, or compositions in which concentrations of about 1 nanomolar or less can be used. In another embodiment, methods utilizing a concentration of about 200 picomolar or less, and even a concentration of about 50 picomolar or less, about 20 picomolar or less, about 10 picomolar or less, or about 5 picomolar or less can be used in many circumstances.

The method can be carried out by addition of the formulations to any extracellular matrix in which cells can live provided that the formulation is formulated so that a sufficient amount of the cargo can contact and/or enter a cell to exert its effect. For example, the method is amenable for use with cells present in a liquid such as a liquid culture or cell growth media, in tissue explants, or in whole organisms, including animals, such as mammals and especially humans.

For dsRNA formulations, the level or activity of a target RNA can be determined by any suitable method now known in the art or that is later developed. It can be appreciated that the method used to measure a target RNA and/or the expression of a target RNA can depend upon the nature of the target RNA. For example, if the target RNA encodes a protein, the term "expression" can refer to a protein or the RNA/transcript derived from the target RNA. In such instances, the expression of a target RNA can be determined by measuring the amount of RNA corresponding to the target RNA or by measuring the amount of that protein. Protein can be measured in protein assays such as by staining or immunoblotting or, if the protein catalyzes a reaction that can be measured, by measuring reaction rates. All such methods are known in the art and can be used. Where target RNA levels are to be measured, any art-recognized methods for detecting RNA levels can be used (e.g., RT-PCR, Northern Blotting, etc.). In targeting viral RNAs with the DsiRNA agents of the instant invention, it is also anticipated that measurement of the efficacy of a dsRNA (e.g., DsiRNA) cargo in reducing levels of a target virus in a subject, tissue, in cells, either in vitro or in vivo, or in cell extracts can also be used to determine the extent of reduction of target viral RNA level(s). Any of the above measurements can be made on cells, cell extracts, tissues, tissue extracts or any other suitable source material.

The determination of whether the expression of a target RNA has been reduced can be by any suitable method that can reliably detect changes in RNA levels. Typically, the determination is made by introducing into the environment of a cell undigested DsiRNA such that at least a portion of that DsiRNA agent enters the cytoplasm, and then measuring the level of the target RNA. The same measurement is made on identical untreated cells and the results obtained from each measurement are compared.

Formulations of the invention can be made as a pharmaceutical composition which comprises a pharmacologically effective amount of a cargo (e.g., peptide, protein, nucleic acid, etc.) and pharmaceutically acceptable carrier. A pharmacologically or therapeutically effective amount refers to that amount of a cargo effective to produce the intended pharmacological, therapeutic or preventive result. The phrases "pharmacologically effective amount" and "therapeutically effective amount" or simply "effective amount" refer to that amount of a cargo effective to produce the intended pharmacological, therapeutic or preventive result. For example, if a given clinical treatment is considered effective when there is at least a 20% reduction in a measurable parameter associated with a disease or disorder, a therapeutically effective amount of a drug for the treatment of that disease or disorder is the amount necessary to effect at least a 20% reduction in that parameter.

Suitably formulated pharmaceutical compositions of this invention can be administered by any means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

In general, a suitable dosage unit of formulation and/or the cargo of a formulation will be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Pharmaceutical composition comprising the cargo can be administered once daily. However, the therapeutic cargo may also be dosed in dosage units containing two, three, four, five, six or more sub-doses administered at appropriate intervals throughout the day. In that case, the cargo contained in each sub-dose must be correspondingly smaller in order to achieve the total daily dosage unit. The dosage unit can also be compounded for a single dose over several days, e.g., using a conventional sustained release formulation which provides sustained and consistent release of the cargo over a several day period. Sustained release formulations are well known in the art. In this embodiment, the dosage unit contains a corresponding multiple of the daily dose. Regardless of the formulation, the pharmaceutical composition must contain cargo in a quantity sufficient to exert its intended effect (e.g., for a dsRNA cargo, to inhibit expression of the target gene) in the animal or human being treated. The formulation can be compounded in such a way that the sum of the multiple units of cargo together contain a sufficient dose.

Data can be obtained from cell culture assays and animal studies to formulate a suitable dosage range for humans. The dosage of formulations of the invention lies within a range of circulating concentrations that include the $ED_{50}$ (as determined by known methods) with little or no toxicity. The dosage may vary within this range depending upon the dosage form employed and the route of administration utilized. For any formulation used in the method of the invention, the therapeutically effective dose can be estimated initially from cell culture assays. A dose may be formulated in animal models to achieve a circulating plasma concentration range of the compound that includes the $IC_{50}$ (i.e., the concentration of the test compound which achieves a half-maximal inhibition of symptoms) as determined in cell culture. Such information can be used to more accurately determine useful doses in humans. Levels of formulation and/or cargo in plasma may be measured by standard methods, for example, by high performance liquid chromatography.

The pharmaceutical compositions can be included in a kit, container, pack, or dispenser together with instructions for administration.

Methods of Treatment

The present invention provides for both prophylactic and therapeutic methods of treating a subject at risk of (or susceptible to) a disease or disorder. In certain aspects, the disease or disorder is caused, in whole or in part, by the expression of a target RNA and/or the presence of such target RNA (e.g., in the context of a viral infection, the presence of a target RNA of the viral genome, capsid, host cell component, etc.).

"Treatment", or "treating" as used herein, is defined as the application or administration of a therapeutic agent (e.g., an immune response reducing formulation) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject an immune response reducing formulation (e.g., a DsiRNA formulation). Subjects at risk for the disease can be identified by, for example, any or a combination of diagnostic or prognostic assays as described herein. Administration of a prophylactic agent can occur prior to the detection of, e.g., viral particles in a subject, or the manifestation of symptoms characteristic of the disease or disorder, such that the disease or disorder is prevented or, alternatively, delayed in its progression. An effective amount of the pharmaceutical composition for treatment is one that, when compared to a control, results in at least 5%, 10%, 25%, 50%, 70%, 80%, 90%, 95%, 99%, or 100% reduction in the symptoms or onset of symptoms.

Another aspect of the invention pertains to methods of treating subjects therapeutically, i.e., alter onset of symptoms of the disease or disorder. These methods can be performed in vitro (e.g., by culturing the cell with the immune response reducing formulation) or, alternatively, in vivo (e.g., by administering the immune response reducing formulation to a subject). An effective amount of the pharmaceutical composition for treatment is one that, when compared to a control results in a delay in the symptoms or onset of symptoms by at least 5%, 10%, 25%, 50%, 70%, 80%, 90%, 95%, 99%, or 100%.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target RNA molecules of certain immune response reducing formulations of the present invention or target RNA modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, a immune response reducing formulation as described herein can be used in an animal model to determine the efficacy, toxicity, or side effects of treatment with said immune response reducing formulation. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N. Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The present invention is described by reference to the following Examples, which are offered by way of illustration and are not intended to limit the invention in any manner. Standard techniques well known in the art or the techniques specifically described below were utilized.

Example 1

Modulation of Immune Response to Toll-Like Receptor Agonists by Immune Response Reducing Lipid-DsiRNA Formulations In Vitro This example illustrates that the immunostimulatory activity of a DsiRNA that acts as a TLR agonist can be selectively antagonized by non-cationic immune response reducing lipids of a DsiRNA-lipid formulation.

Oligonucleotide Synthesis

Individual RNA strands are synthesized and HPLC purified according to standard methods (Integrated DNA Technologies, Coralville, Iowa). All oligonucleotides are quality control released on the basis of chemical purity by HPLC analysis and full length strand purity by mass spectrometry analysis. Duplex RNA DsiRNAs are prepared before use by mixing equal quantities of each strand, briefly heating to 100° C. in RNA buffer (IDT) and then allowing the mixtures to cool to room temperature.

RNA Isolation and Analysis

Cells are washed once with 2 mL of PBS, and total RNA is extracted using RNeasy Mini Kit™ (Qiagen) and eluted in a final volume of 30 μL. 1 μg of total RNA is reverse-transcribed using Transcriptor $1^{st}$ Strand cDNA Kit™ (Roche) and random hexamers following manufacturer's instructions. One-thirtieth (0.66 μL) of the resulting cDNA is mixed with 5 μL of IQ Multiplex Powermix (Bio-Rad) together with 3.33 μL of $H_2O$ and 1 μL of a 3 μM mix containing 2 sets of primers and probes specific for human genes that are assayed (e.g., K-RAS, HPRT1, etc.).

Quantitative RT-PCR

A CFX96 Real-time System with a C1000 Thermal cycler (Bio-Rad) is used for the amplification reactions. PCR conditions are: 95° C. for 3 min; and then cycling at 95° C., 10 sec; 55° C., 1 min for 40 cycles. Each sample is tested in triplicate. Relative test mRNA levels are compared with mRNA levels obtained in control samples treated with the transfection reagent plus a control mismatch duplex, or untreated. Data is analyzed using Bio-Rad CFX Manager version 1.0 software.

A DsiRNA is identified that, when administered naked or in the context of a lipidic formulation lacking an immune response reducing lipid of the instant invention, induces an immune response in a human peripheral blood mononuclear cell (PBMC) to which the DsiRNA is administered. The DsiRNA possesses robust target gene inhibitory efficacy (e.g., in PBMC and/or cell culture transfection assays, the DsiRNA exhibits an IC50 value in the picomolar range).

The preceding target gene is selected from among art-recognized "housekeeping" genes. Housekeeping genes are selected as target genes for the double purposes of assuring that target genes possessed strong and homogenous expression in human cells and of minimizing expression level variability. For example, double stranded RNAs specific for the human target gene Hypoxanthine-Guanine Phosphoribosyl Transferase (HPRT1; GenBank Accession No. NM_000194 and GI:164518913) are tested for efficacy in human human peripheral blood mononuclear cell (PBMC) cells.

The DsiRNA is encapsulated in a lipidic carrier system formulation comprising a cationic lipide, e.g., PEG-cDMA:DLinDMA:cholesterol:DSPC in a 2:40:48:10 mol % ratio (2:40 SNALP), which is prepared, e.g., using a syringe press process. To test the immune response reducing efficacy of a co-formulated lipid of the invention, the DsiRNA is also encapsulated in a corresponding lipid carrier system formulation that comprises a non-cationic lipid which is selected from FIGS. 1-14, at concentration from 1 mol % to 50 mol % (e.g., present at 40 mol %).

Fresh human peripheral blood mononuclear cells (PBMCs) are isolated and seeded at about $3\times10^5$ cells/well in a total volume of 180 μl. (Alternatively, marrow, splenocyte or hepatocyte cells are isolated and used, or any such cells are co-cultured with hepatocytes, with such cells optionally derived from any suitable mammalian source, e.g., primate, rodent, etc.) Next, 20 μl of a lipid carrier system formulation comprising the DsiRNA and either lacking or comprising the lipid selected from FIGS. 1-14 is diluted in PBS and is added to the PBMCs. For time course experiments, PBMCs are pretreated with a control and the appropriate DsiRNA-lipid formulation is added at 0, 0.5, or 2 hours after pretreatment. The DsiRNA transfection mixtures are added to cells to give a final DsiRNA concentration of 50 pM, 200 pM, or 1 nM in a volume of 150 μl. Each DsiRNA transfection mixture is added to 3 wells for triplicate DsiRNA treatments. Cells are incubated at 37° C. for 24 hours in the continued presence of the DsiRNA lipid carrier system formulation. At t=24 hr., the cell supernatant is harvested and IFN-α and/or IL-6 levels are determined using ELISA, and the cells are lysed and RNA prepared from each well. Target RNA level or expression following treatment is evaluated by a quantitative method (e.g., RT-PCR, Northern blot) for the target gene and for a control gene (e.g., actin or 36B4, an RNA polymerase subunit) for normalization. Alternatively, the cells are lysed and total protein is prepared from each well. Target protein level or expression following treatment is evaluated by Western blot and the signal is quantified. Triplicate data is averaged and the standard deviations determined for each treatment. Normalized data are graphed and the percent reduction of target mRNA by dsRNAs of the invention in comparison to appropriate control dsRNAs (e.g., inverted control dsRNAs) is determined.

For cells administered a DsiRNA-lipid formulation comprising an immune response reducing lipid of the invention, a significantly reduced level of IFN-α and/or IL-6 is identified for formulations comprising a lipid of FIGS. 1-14, as compared to an appropriate control formulation lacking the lipid of FIGS. 1-14. Such effects are observed to be dose-dependent with respect to levels of DsiRNA-lipid formulation administered. In addition, the target gene inhibitory efficacy of the formulated DsiRNA (as determined, e.g., by quantitative RT-PCR and/or other method) is observed to be maintained in DsiRNA-lipid formulations possessing immune response reducing lipids, as compared to appropriate control DsiRNA-lipid formulations lacking immune response reducing lipids.

Example 2

Modulation of Immune Response to Toll-Like Receptor Agonists by Immune Response Reducing Lipid-DsiRNA Formulations In Vivo Mice are obtained and treated with either DsiRNA formulated into lipid particles comprising an immune response reducing lipid of any of FIGS. 1-14, or with an appropriate control DsiRNA-lipid formulation that lacks the immune response reducing lipid. For transfection in vivo, normal CD-1 mouse is used as a model. To prepare DsiRNA formulated lipid particles for transfection, 25 μg or an indicated amount of DsiRNA is diluted in 100 μl of distilled water (endotoxin screened, Gibco). The diluted DsiRNA solution is added to a polystyrene tube containing an indicated amount of liposomes in 100 μl and mixed immediately. The complexes are kept at room temperature for 30 min. before being administered to the animals via tail vein.

Administration of the control DsiRNA-lipid formulation induces significant elevation in plasma IFN-α and/or IL-6, whereas the DsiRNA-lipid formulation comprising an immune response reducing lipid exhibits a measurably reduced or ablated cytokine response, indicating that the inhibitory effects of the immune response reducing lipid evaluated in vitro still manifest in vivo.

In further in vivo experiments, PEGylated DsiRNA-lipid formulations that induce production of PEG antibodies in a subject when such formulations lack immune response reducing lipids as described herein are administered to mice, either formulated with an immune response reducing lipid of FIGS. 1-14, or with an appropriate control formulation lacking the immune response reducing lipid of FIGS. 1-14. Following administration of such formulations, anti-PEG antibody production is assessed (e.g., at 24 hours post-administration, 2 days post-administration, 4 days post-administration, 1 week post-administration, 2 weeks post-administration, 3 weeks post-administration, 4 weeks post-administration, 5 weeks post-administration, etc.). Optionally, such formulations are administered to a subject repeatedly, e.g., once a day or every other day for a series of days; once a week for two, four, six or eight weeks, etc. Decreased anti-PEG antibody production is observed in mice administered a DsiRNA-lipid formulation comprising an immune response reducing lipid of FIGS. 1-14, as compared to an appropriate control DsiRNA-lipid formulation that lacks an immune response reducing lipid of FIGS. 1-14.

The invention claimed is:

1. A formulation comprising:
   an agent that induces an immune response when administered to a mammalian subject; and
   a first lipid that reduces said immune response to said agent in a mammalian subject, as compared to an immune response to a control formulation comprising said agent but lacking said first lipid; and
   wherein said first lipid is selected from the group consisting of: DPC-036, DPC-4, DPC-1, DPC-2, DPC-3, DPC-12, DPC-8, DPC-7, DPC-6, DPC-5, DPC-9, DPC-10, DPC-11 and DPC-13.

2. The formulation of claim 1, wherein said first lipid is a non-cationic lipid.

3. The formulation of claim 1, wherein said agent is a cargo of said formulation.

4. The formulation of claim 1, wherein said agent is an excipient of said formulation.

5. The formulation of claim 4, wherein said excipient is polyethoxylated castor oil.

6. The formulation of claim 1, wherein said agent is selected from the group consisting of a nucleic acid, an active drug molecule and a vehicle component.

7. The formulation of claim 6, wherein said nucleic acid is a dsRNA.

8. The formulation of claim 1, further comprising a second lipid.

9. The formulation of claim 8, wherein said second lipid is a cationic lipid.

10. The formulation of claim 8, wherein said second lipid activates TLR4 in the absence of said first lipid.

11. The formulation of claim 8, wherein said first lipid comprises between 1 mol % and 80 mol % of the total lipid of said formulation.

12. The formulation of claim 8, wherein said first lipid comprises between 20 mol % and 50 mol % of the total lipid of said formulation.

13. The formulation of claim 1, wherein said immune response is a response selected from the group consisting of a TNF-alpha-mediated immune response and an interferon-mediated immune response.

14. The formulation of claim 13, wherein said interferon is IL-1β.

15. The formulation of claim 1, wherein said immune response in a subject is measured by a method selected from the group consisting of detecting elevated interferon levels in said subject, detecting elevated TNF-alpha levels in said subject and detecting a symptom of an immune response selected from the group consisting of fatigue, flu-like symptoms, diarrhea, reduced bone marrow function, infection, rash, hypotension, arrhythmia, elevated liver enzymes, complement activation, splenomegaly, enlarged lymph nodes, erythema, fainting, anemia and bleeding problems.

16. The formulation of claim 1, further comprising a delivery moiety.

17. The formulation of claim 16, wherein said delivery moiety induces an immune response in a mammalian subject, either alone, or when said delivery moiety is in said formulation.

18. The formulation of claim 17, wherein the immune response is an innate immune response.

19. The formulation of claim 16 wherein said delivery moiety is a selected from the group consisting of a polypeptide, a carbohydrate and a lipid.

20. The formulation of claim 16, wherein said delivery moiety is selected from the group consisting of somatostatin (sst2), bombesin/GRP, luteinizing hormone-releasing hormone (LHRH), neuropeptide Y (NPY/Y1), neurotensin (NT1), vasoactive intestinal polypeptide (VIP/VPAC1) and cholecystokinin (CCK/CCK2).

21. The formulation of claim 16, wherein an immune response is induced by administration of said formulation to a subject, and wherein said immune response induced by said formulation is less than the immune response induced by a control formulation that lacks said first lipid.

22. The formulation of claim 16, wherein said formulation induces no detectable immune response in a subject when administered to said subject.

23. The formulation of claim 1, further comprising PEG.

24. The formulation of claim 23, wherein said first lipid reduces or prevents formation of antibodies specific for PEG in said subject.

25. A formulation comprising:
   a dsRNA comprising a sequence sufficiently complementary to a target gene along at least 19 nucleotides of said dsRNA sequence length to reduce target gene expression when said dsRNA is introduced into a mammalian cell;
   a first lipid; and
   a second lipid,
   wherein said first lipid reduces or prevents an immune response to said formulation and/or to said second lipid in a mammalian subject when said formulation is administered to said mammalian subject, as compared to an appropriate control dsRNA lacking said first lipid; and
   wherein said first lipid is selected from the group consisting of: DPC-036, DPC-4, DPC-1, DPC-2, DPC-3, DPC-12, DPC-8, DPC-7, DPC-6, DPC-5, DPC-9, DPC-10, DPC-11 and DPC-13.

26. The formulation of claim 25, wherein said dsRNA is an isolated double stranded ribonucleic acid (dsRNA) comprising a first oligonucleotide strand having a 5' terminus and a 3' terminus and a second oligonucleotide strand having a 5' terminus and a 3' terminus, wherein:
   said dsRNA comprises a duplex region of at least 25 base pairs;
   said first strand has a length which is at least 25 nucleotides and said second strand has a length which is at least 26 nucleotides;

said second strand is 1-5 nucleotides longer at its 3' terminus than said 5' terminus of said first strand; and said second oligonucleotide strand is sufficiently complementary to said target gene along at least 19 nucleotides of said second oligonucleotide strand length to reduce target gene expression when said dsRNA is introduced into a mammalian cell.

27. The formulation of claim 26, wherein said first strand of said dsRNA is 25-30 nucleotides in length.

28. The formulation of claim 26, wherein said second strand of said dsRNA is two nucleotides longer at its 3' terminus than said 5' terminus of said first strand.

29. The formulation of claim 26, wherein said 3' terminus of said first strand of said dsRNA and said 5' terminus of said second strand form a blunt end.

30. The formulation of claim 26, wherein said dsRNA comprises first strand and second strand lengths selected from the group consisting of the following: 25 nucleotide first strand and second strand length selected from the group consisting of 26, 27, 28 and 29 nucleotides; 26 nucleotide first strand and second strand length selected from the group consisting of 27, 28, 29 and 30 nucleotides; 27 nucleotide first strand and second strand length selected from the group consisting of 28, 29 and 30 nucleotides; 28 nucleotide first strand and second strand length selected from the group consisting of 29 and 30 nucleotides; 29 nucleotide first strand and 30 nucleotide second strand.

31. The formulation of claim 26, wherein said first strand of said dsRNA is 25 nucleotides in length and said second strand is 27 nucleotides in length.

32. The formulation of claim 25, wherein said dsRNA is present in an amount effective to reduce target RNA levels when said formulation contacts a cell of a mammalian subject by an amount (expressed by %) selected from the group consisting of at least 10%, at least 50% and at least 80-90%.

33. The formulation of claim 32, wherein said effective amount is a dosage selected from the group consisting of 1 microgram to 5 milligrams per kilogram of said subject per day, 100 micrograms to 0.5 milligrams per kilogram, 0.001 to 0.25 milligrams per kilogram, 0.01 to 20 micrograms per kilogram, 0.01 to 10 micrograms per kilogram, 0.10 to 5 micrograms per kilogram, and 0.1 to 2.5 micrograms per kilogram.

34. A pharmaceutical composition comprising the formulation of claim 1 and a pharmaceutically acceptable carrier.

35. A kit comprising the formulation of claim 1 and instructions for its use.

36. A method for reducing expression of a target gene in a mammal comprising administering the formulation of claim 25 to a mammal in an amount sufficient to reduce expression of a target gene in the mammal.

* * * * *